US010730842B2

(12) United States Patent
Hulme et al.

(10) Patent No.: US 10,730,842 B2
(45) Date of Patent: Aug. 4, 2020

(54) SMALL MOLECULE INHIBITORS OF DYRK1A AND USES THEREOF

(71) Applicant: ARIZONA BOARD OF REGENTS ON BEHALF OF THE UNIVERSITY OF ARIZONA, Tucson, AZ (US)

(72) Inventors: Christopher Hulme, Tucson, AZ (US); Travis Dunckley, Phoenix, AZ (US); Yeng-Jeng Shaw, Tucson, AZ (US)

(73) Assignees: ARIZONA BOARD OF REGENTS ON BEHALF OF THE UNIVERSITY OF ARIZONA, Tucson, AZ (US); THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 0 days.

(21) Appl. No.: 15/756,917

(22) PCT Filed: Sep. 2, 2016

(86) PCT No.: PCT/US2016/050198
§ 371 (c)(1),
(2) Date: Mar. 1, 2018

(87) PCT Pub. No.: WO2017/040993
PCT Pub. Date: Mar. 9, 2017

(65) Prior Publication Data
US 2019/0062284 A1   Feb. 28, 2019

Related U.S. Application Data

(60) Provisional application No. 62/213,904, filed on Sep. 3, 2015.

(51) Int. Cl.
| C07D 235/06 | (2006.01) |
| A61K 31/4184 | (2006.01) |
| A61K 31/4439 | (2006.01) |
| A61K 31/4545 | (2006.01) |
| A61K 31/506 | (2006.01) |
| A61K 31/5377 | (2006.01) |
| A61K 45/06 | (2006.01) |
| C07D 401/04 | (2006.01) |
| C07D 401/14 | (2006.01) |
| C07D 403/04 | (2006.01) |
| C07D 405/04 | (2006.01) |
| C07D 405/14 | (2006.01) |
| C07D 409/04 | (2006.01) |
| C07D 471/04 | (2006.01) |

(52) U.S. Cl.
CPC ........ *C07D 235/06* (2013.01); *A61K 31/4184* (2013.01); *A61K 31/4439* (2013.01); *A61K 31/4545* (2013.01); *A61K 31/506* (2013.01); *A61K 31/5377* (2013.01); *A61K 45/06* (2013.01); *C07D 401/04* (2013.01); *C07D 401/14* (2013.01); *C07D 403/04* (2013.01); *C07D 405/04* (2013.01); *C07D 405/14* (2013.01); *C07D 409/04* (2013.01); *C07D 471/04* (2013.01)

(58) Field of Classification Search
None
See application file for complete search history.

(56) References Cited

U.S. PATENT DOCUMENTS

| 4,331,671 A | 5/1982 | Lesher |
| 6,218,388 B1 | 4/2001 | Boschelli et al. |
| 7,238,713 B2* | 7/2007 | Anderson ............ C07D 401/06 514/324 |
| 7,666,879 B2 | 2/2010 | Barda et al. |
| 2005/0026960 A1 | 2/2005 | Kephart et al. |
| 2011/0112091 A1 | 5/2011 | Brzozka et al. |
| 2015/0203472 A1* | 7/2015 | Ceccarelli ............ C07D 401/14 514/338 |

FOREIGN PATENT DOCUMENTS

| CN | 104447567 | 3/2015 |
| DE | 102014009011 | 12/2014 |
| JP | 57-136583 | 8/1982 |
| WO | 99/16755 | 4/1999 |
| WO | 2005/009997 | 2/2005 |
| WO | 2005/092866 | 10/2005 |

(Continued)

OTHER PUBLICATIONS

Palmer, B. D. et al. Structure-Activity Relationships for 1-Phenylbenzimidazoles as Selective ATP Site Inhibitors of the Platelet-Derived Growth Factor Receptor. Journal of Medicinal Chemistry, 1998, vol. 41(27), pp. 5457-5465.

Farahat, A. A. et al. Copper(I) 3-Methylsalicylate Mediates the Chan-Lam N-Arylation of Heterocycles. Synthetic Communications, 2015, vol. 45(2), pp. 245-252.

Ahn, JS, et al., Defining Cdk5 Ligand Chemical Space with Small Molecule Inhibitors of Tau Phosphorylation, Chem. Biol., 2005, 12(7), 811-823.

Ahn KJ, et al., DYRK1A Bac transgenic mice show altered synaptic plasticity with learning and memory defects, Neurobiol Dis 2006;22:463-472.

Airaksinen MM, et al., Tremorigenic Effect and Inhibition of Tryptamine and Serotonin Receptor Binding by Beta-Carbolines, Pharmacol Toxicol 1987;60:5-8.

(Continued)

*Primary Examiner* — Kortney L. Klinkel
*Assistant Examiner* — Tori Strong
(74) *Attorney, Agent, or Firm* — Casimir Jones, SC; Robert Goetz

(57) ABSTRACT

This invention is in the field of medicinal chemistry. In particular, the invention relates to a new class of small-molecules having a benzimidazole or imidazopyridine structure which function as inhibitors of DYRK1A protein, and their use as therapeutics for the treatment of Alzheimer's disease, Down syndrome, glioblastoma, autoimmune diseases, inflammatory disorders (e.g., airway inflammation), and other diseases.

10 Claims, 2 Drawing Sheets

(56) References Cited

FOREIGN PATENT DOCUMENTS

| WO | 2008/045371 | 10/2007 | | |
|---|---|---|---|---|
| WO | 2010/007317 | 1/2010 | | |
| WO | 2010/080503 | 7/2010 | | |
| WO | 2011/022439 | 2/2011 | | |
| WO | 2012/174312 | 12/2012 | | |
| WO | 2013/026806 | 2/2013 | | |
| WO | WO 2013/147711 | 10/2013 | | |
| WO | 2014/053409 | 4/2014 | | |
| WO | WO-2014053409 A1 * | 4/2014 | ........... | C07D 403/04 |
| WO | WO 2014/096388 | 6/2014 | | |
| WO | 2014/151147 | 9/2014 | | |

OTHER PUBLICATIONS

Albores R, et al., Mitochondrial respiratory inhibition by N-methylated Beta-carboline derivatives structurally resembling N-methyl-4-phenylpyridine, PNAS 1990;87:9368-9372.
Altafaj X, et al., Neurodevelopmental delay, motor abnormalities and cognitive deficits in transgenic mice . . . , Hum Mol Genet 2001;10:1915-1923.
Anderson K, et al., Pyrido[2,3-d]pyrimidines: discovery and preliminary SAR of a novel series of DYRK1B and DYRK1A inhibitors., Bioorg. Med. Chem. Lett., 2013, 23(24), 6610-6615.
Arron et al., NFAT dysregulation by increased dosage of DSCR1 and DYRK1A on chromosome 21. 2006 Nature 411, 595-600.
Bain J, et al., The specificities of protein kinase inhibitors: an update., Biochem J. 2003;371:199-204.
Bain J, et al., The selectivity of protein kinase inhibitors: A further update. Biochem J 2007;408:297-315.
Becker et al. "Activation, regulations, and inhibition of DYRK1A" FEBS Journal Dec. 3, 2011, vol. 278, p. 246-256.
Belichenko NP, et al., J Neurosci 2009;29:5938-5948.
Belinchenko PV, et al., J Comp Neurol 2004;480:281-298.
Belichenko PV, et al., J Comp Neurol 2007;504:329-345.
Branch I, et al., J Neuropathol Exp Neurol 2004;63:429-440.
Callaway JC, et al., Pharmacokinetics of Hoasca alkaloids in healthy humans. J Ethnopharmacol 1999;65:243-256.
Chabert C, et al., Behav Genet 2004;34:559-569.
Chen et al., Dosage of Dyrk1 a shifts cells within a p21-cyclin D1 signaling map to control the decision to enter the cell cycle. 2013 Mol. Cell 52, 87-100.
Cohen, P. Protein kinases—the major drug targets of the twenty-first century? Nat. Rev. Drug Discov., 2002, 1(4), 309-315.
Coombs, T. C., et al., Small-molecule pyrimidine inhibitors of the cdc2-like (Clk) and dual specificity tyrosine phosphorylation-regulated (Dyrk) kinases: Development of chemical probe ML315, Bioorg Med Chem Lett 2013, 23, 3654-3661.
De La Torre R, et al., Epigallocatechin-3-gallate, a DYRK1A inhibitor, rescues cognitive deficits in Down syndrome mouse models and in humans. Mol Nutr Food Res 2014;58:278-288.
Deng X, et al., Mirk kinase inhibition blocks the in vivo growth of pancreatic cancer cells, Genes & Cancer (2014), 5(9-10), 337-347.
Frost D, et al., β-Carboline Compounds, Including Harmine, Inhibit DYRK1A and Tau Phosphorylation at Multiple Alzheimer's Disease-Related Sites, PLoS One 2011;6:e19264.
Fuentes JA, et al., An investigation on the central effects of harmine, harmaline and related beta-carbolines. Neuropharmacology 1971;10:15-23.
Gambelunghe C, et al., Identification of N,N☐Edimethyltryptamine and β☐carbolines in psychotropic ayahuasca beverage, Biomed Chromatogr 2008;22:1056-1059.
Guo et al., DYRK1A and DYRK3 Promote Cell Survival through Phosphorylation and Activation of SIRT1, J Biol. Chem. 2010, 285 (17), 13223-13232.
Hamann, M,.et al., Glycogen Synthase Kinase-3 (GSK-3) Inhibitory Activity and Structure—Activity Relationship (SAR) Studies of the Manzamine Alkaloids. Potential for Alzheimer's Disease J. Nat. Prod., 2007, 70(9), 1397-1405.
Hammerle et al., Transient expression of Mnb/Dyrk1 a couples cell cycle exit and differentiation of neuronal precursors by inducing p27KIP1 expression and suppressing NOTCH signaling 2011 Development 138, 2543-2554.
Hitchcock SA, Structure—Brain Exposure Relationships J. Med. Chem., 2006, 49(26), 7559-83.
International Search Reoprt and Written Opinion, International Patent Application No. PCT/US2016/050198, dated Feb. 7, 2017.
Ionescu et al. "DYRK1A Kinase Inhibitors with Emphasis on Cancer" Mini Reviews in Mediciinal Chemistry, Sep. 2012, vol. 12, p. 1-14.
Kawanishi K, et al., Pharmacol Biochem Behav 1994;47:689-699.
Khor B, et al., Khor B, et al., eLife 2015;4:e05920 eLife 2015;4:e05920.
Lott IT, et al., Cognitive deficits and associated neurological complications in individuals with Down's syndrome. Lancet neurology 2010;9:623-633.
Megarbane A, et al., The 50th anniversary of the discovery of trisomy 21: the past, present, and future of research and treatment of Down syndrome. Genet Med 2009;11:611-616.
Mennenga et al., Harmine treatment enhances short-term memory in old rats: Dissociation of cognition and the ability to perform the procedural requirements of maze testing. Physiol. Behav. 2015, 138, 260-265.
Michan et al., SIRT1 Is Essential for Normal Cognitive Function and Synaptic Plasticity J. Neurosci. 2010, 30(29), 9695-9707.
Nemoto T, et al., Constitutive activity of glycogen synthase kinase-3β: Positive regulation of steady-state levels of insulin receptor substrates-1 and -2 in adrenal chromaffin cells Brain Research 2006, 1110(1), 1-12.
Oumata N, et al., Roscovitine-derived, dual-specificity inhibitors of cyclin-dependent kinases and casein kinases 1. J. Med. Chem., 2008, 51(17), 5229-5242.
Perez DI, et al., Protein kinases CK1 and CK2 as new targets for neurodegenerative diseases. Med. Res. Rev., 2011, 31(6), 924-954.
Reeves RH, et al., A mouse model for Down syndrome exhibits learning and behaviour deficits. Nat Genet 1995;11:177-184.
Roskoski, R. USFDA approved protein kinase inhibitors. Blue Ridge Institute for Medical Research. Horse Shoe, NC. 2017, 13 pages.
Ryoo SR, et al., DYRK1A-mediated hyperphosphorylation of Tau. A functional link between Down syndrome and Alzheimer disease. J Biol Chem 2007;282:34850-34857.
Ryoo SR, et al., Dual specificity tyrosine(Y)phosphorylation regulated kinase 1Amediated phosphorylation of amyloid precursor protein: evidence for a functional link between Down syndrome and Alzheimer's disease. J Neurochem 2008;104:1333-1344.
Sago H, et al., Ts1Cje, a partial trisomy 16 mouse model for Down syndrome exhibits learning and behavioral abnormalities. PNAS 1998;95:6256-6261.
Seifert et al., DYRK1A phosphorylates caspase 9 at an inhibitory site and is potently inhibited in human cells by harmine. 2008 FEBS J. 275, 6268-6280.
Siarey RJ, et al., Abnormal synaptic plasticity in the Ts1Cje segmental trisomy 16 mouse model of Down syndrome. Neuropharmacology 2005;49:122-128.
Smith B, et al., Recent Advances in the Design, Synthesis, and Biological Evaluation of Selective DYRK1A Inhibitors: A New Avenue for a Disease Modifying Treatment of Alzheimer's? ACS Chem Neurosci 2012;3:857-872.
Smith DJ, et al., Functional screening of 2 Mb of human chromosome 21q22.2 in transgenic mice implicates minibrain in learning defects associated with Down syndrome. Nat Genet 1997;16:28-36.
Tahtouh, T., et al., Selectivity, Cocrystal Structures, and Neuroprotective Properties of Leucettines, a Family of Protein Kinase Inhibitors Derived from the Marine Sponge Alkaloid Leucettamine B. J Med Chem 2012, 55, 9312-9330.
Zhong, C. et al. "A QSAR study on inhibitory activities of 1-phenylbenzimidazoles against the platelet-derived growth factor receptor" Bioorganic & Medicinal Chemistry 12 (2004) 4009-4015.
Pagano et al. "Optimization of Protein Kinase CK2 Inhibitors Derived from 4,5,6,7-Tetrabromobenzimidazole" J. Med Chem. 47, pp. 6239-6247, Dec. 2, 2004.

(56) References Cited

OTHER PUBLICATIONS

Ramana, Tamminana et al. "Preparation of 2-Azido-1-Substituted-1 H-Benzo[d]imidazoles Using a Copper-Promoted Three-Component Reaction and Their Further Conversion into 2-Amino and 2-Triazolyl Derivatives" Chemistry—A European Journal, 18-42, pp. 13279-13283, Oct. 15, 2012.

Ziegler et al. "A Versatile Approach to Ullmann C-N Couplings at Room Temperature: New Families of Nucleophiles and Electrophiles for Photoinduced, Copper-Catalyzed Processes" JACS, 135/35, pp. 13107-13112, Aug. 22, 2013.

Bojjireddy, N. et al. "Pharmacological and Genetic Targeting of the PI4KA Enzyme Reveals Its Importatnt Role in Maintaining Plasma Membrane Phosphatidylinositol 4-Phosphate and Phosphatidylinositol 4,5-Bisphosphate Levels" The Journal of Biological Chemistry, 2014 289(9), 6120-32.

Examination Report, Australian Patent Application No. 2016315881, dated May 26, 2019, 7 pages.

* cited by examiner

United States Patent US 10,730,842 B2

SMALL MOLECULE INHIBITORS OF DYRK1A AND USES THEREOF

CROSS-REFERENCE TO RELATED APPLICATIONS

This application is a U.S. 371 national phase entry of International Patent Application No. PCT/US2016/050198, filed Sep. 2, 2016, which claims priority to and the benefit of U.S. Provisional Application No. 62/213,904, filed Sep. 3, 2015, which are hereby incorporated by reference in their entireties.

FIELD OF THE INVENTION

This invention is in the field of medicinal chemistry. In particular, the invention relates to a new class of small-molecules having a benzimidazole or imidazopyridine structure which function as inhibitors of DYRK1A protein, and their use as therapeutics for the treatment of Alzheimer's disease, Down syndrome, glioblastoma, autoimmune diseases, inflammatory disorders (e.g., airway inflammation), and other diseases.

INTRODUCTION

With 24.3 million people affected in 2005 and an estimated rise to 42.3 million in 2020, dementia is currently a leading unmet medical need and costly burden on public health. Seventy percent of these cases have been attributed to Alzheimer's disease (AD), a neurodegenerative pathology whose most evident symptom is a progressive decline in cognitive functions.

The underlying treatment of learning and/or memory disorders is a huge and significantly unmet medical need and also included learning and memory repair after, for example, incidents of stroke or significant brain damage. As such, an improved understanding of the dementia (and other neuropathology) and related improved treatment methods are needed.

SUMMARY OF THE INVENTION

In addition to the overwhelmingly prominent β-amyloid hypothesis being evaluated in a multitude of clinical trials through small molecule modulation of γ- and β-secretases and numerous immune-based approaches, aberrant phosphorylation of the tau protein is believed to significantly contribute to the development of AD and thus affords an alternate approach for therapeutic development. Tau is a cytoplasmic protein involved in the stabilization of microtubules under normal conditions. In AD, neuronal tau has been found to be excessively phosphorylated, with subsequent generation of aggregates of phosphorylated tau protein, known as "neurofibrillary tangles" (NFTs). NFTs and amyloid plaques are considered the most common hallmarks of AD and are correlated with neurofibrillary degeneration, neuronal death, and dementia.

Interestingly, several protein kinases have been implicated in neuronal development and, in particular, their overexpression and aberrant activation have been shown to play a significant role in the development of AD via tau phosphorylation. Dual specificity tyrosine phosphorylation regulated kinase-1A (DYRK1A) is important in neuronal development and plays a variety of functional roles within the adult central nervous system. The DYRK1A gene is located within the Down syndrome critical region (DSCR) on human chromosome 21 and current research suggests that overexpression of DYRK1A may be a significant factor leading to cognitive deficits in people with Alzheimer's disease (AD) and Down syndrome (DS).

Currently, treatment options for cognitive deficiencies associated with Down syndrome, as well as Alzheimer's disease, are extremely limited and represent a major unmet therapeutic need. Small molecule inhibition of DYRK1A activity in the brain may provide an avenue for pharmaceutical intervention of mental impairment associated with AD and other neurodegenerative diseases.

Increased expression of the DYRK1A gene has been implicated in both the cognitive deficits of Down syndrome (DS) and the early onset of tau and amyloid neuropathologies that are associated with this genetic disorder. DYRK1A levels are increased in transgenic mouse models of DS and develop DS-like phenotypes including hippocampal-dependent spatial learning and memory deficits and developmental delays. Together these data strongly support a central function for DYRK1A in cognitive deficits associated with DS. Moreover, inhibition of excess DYRK1A activity has been shown to improve these DYRK1A-mediated cognitive deficits after administration of the natural products epigallocatechin-3-gallate (EGCg) and harmine, the standards for DYRK1A inhibition at the on-set of this translational campaign. However, these probes are not significantly selective and have numerous off-target effects that reduce their practical long-term use. To circumvent many of the detrimental issues observed, in particular with harmine, knowledge-based design efforts herein have unearthed novel small molecule series of structurally unique benzimidazole and imidazopyridine DYRK1A inhibitors, amenable for use as probes to test the benefits of selective DYRK1A inhibition in mouse models of DS/AD and a variety of other disease states including Parkinson's disease, Pick's disease, Huntington's and additional tauopathies.

Experiments conducted during the course of developing embodiments for the present invention designed, synthesized and biologically evaluated benzimidazole and imidazopyridine compounds as inhibitors of the dual specificity tyrosine phosphorylation regulated kinase-1A (DYRK1A) and their potential for use as therapeutics against AD and other disorders related to DYRK-1A activity (e.g., DS, other neuropathology, cancer (e.g., glioblastoma), cognitive enhancement). Many benzimidazole and imidazopyridine compounds were also shown to exhibit activity against DYRK1B and exhibit some degree of activity against other kinases implicated in a variety of disease states.

The DYRK1A inhibitors described herein can also be considered as potential therapeutics for the treatment of developmental diseases such as Down syndrome, and neurodegenerative diseases such as Parkinson's disease, and Huntington's disease. Moreover, the DYRK1A inhibitors of the present invention have been also implicated as potential therapeutics for the treatment of glioblastomas and further potential utility is highlighted in the oncology arena (see, e.g., Ionescu et al., Mini-reviews in Medicinal Chemistry, 2012, 12, 1315-1329).

These novel DYRK1A inhibitors may also have utility as general cognitive enhancers, given the published findings that DYRK1A can phosphorylate sirtuin 1, a key regulator of learning and memory (see, e.g., Michan et al., J. Neurosci. 2010, 30(29), 9695-9707; Guo et al., J Biol. Chem. 2010, 285 (17), 13223-13232). The potential utility of these DYRK1A compound series is further reinforced by findings that harmine, a potent, but relatively less selective DYRK1A inhibitor, enhances memory performance in wild-type rodents (Mennenga et al., Physiol. Behav. 2015, 138, 260-265).

These novel DYRK1A inhibitors may also have further utility as results identify DYRK1A as a physiologically relevant regulator of $T_{reg}$ cell differentiation and suggest a broader role for other DYRK family members in immune homeostasis. As such, new roles may be found in autoimmune diseases such as inflammatory bowel disease and type 1 diabetes (see, e.g., Khor B, et al., eLife 2015; 4:e05920).

Accordingly, this invention relates to a new class of small-molecules having a benzimidazole or imidazopyridine structure which function as inhibitors of DYRK1A protein, and their use as therapeutics for the treatment of disorders related to DYRK1A activity (e.g., AD, DS, neuropathology, glioblastoma, autoimmune diseases, inflammatory disorders (e.g., airway inflammation)).

In a particular embodiment, benzimidazole and imidazopyridine compounds encompassed within Formula I are provided:

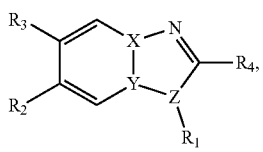

including pharmaceutically acceptable salts, solvates, and/or prodrugs thereof.

Formula I is not limited to a particular chemical moiety for R1, R2, R3, R4, X, Y and Z. In some embodiments, the particular chemical moiety for R1, R2, R3, R4, X, Y and Z independently include any chemical moiety that permits the resulting compound to inhibit DYRK1A activity. In some embodiments, the particular chemical moiety for R1, R2, R3, R4, X, Y and Z independently include any chemical moiety that permits the resulting compound to inhibit one or more of: DYRK1A related PI3K/Akt signaling; DYRK1A related tau phosphorylation; DYRK1A related NFAT phosphorylation; DYRK1A related ASK1/JNK1 pathway activation; DYRK1A related p53 phosphorylation; DYRK1A related Amph 1 phosphorylation; DYRK1A related Dynamin 1 phosphorylation; DYRK1A related Synaptojanin phosphorylation; DYRK1A related presenilin 1 (the catalytic sub-unit of γ-secretase) activity; DYRK1A related amyloid precursor protein phosphorylation; and DYRK1A related SIRT1 activation.

In some embodiments, X—Y—Z is

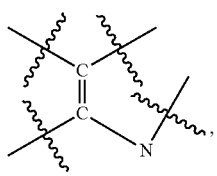 [SMILES: *NC(*)=C(*)*]

thereby rendering the resulting compound a benzimidazole compound having the following formula:

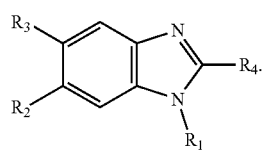

In some embodiments, X—Y—Z is

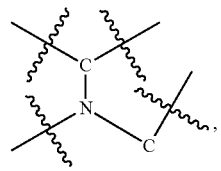 [SMILES: *CN(*)C(*)*]

thereby rendering the compound an imidazopyridine compound having the following formula:

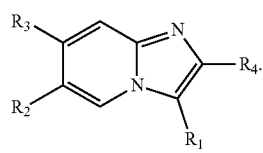

In some embodiments, R1 is selected from hydrogen, aryl and substituted aryl,

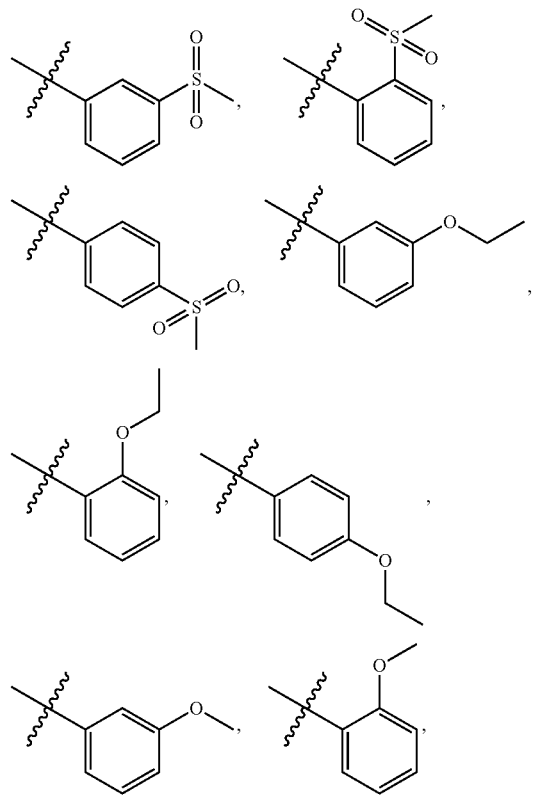

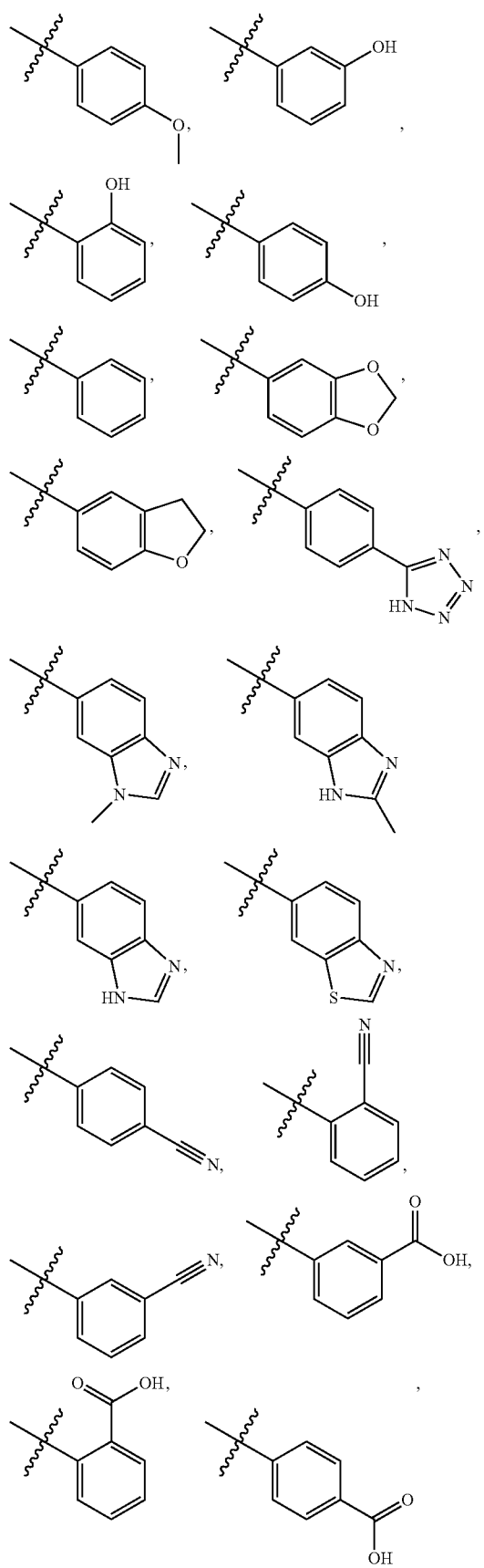
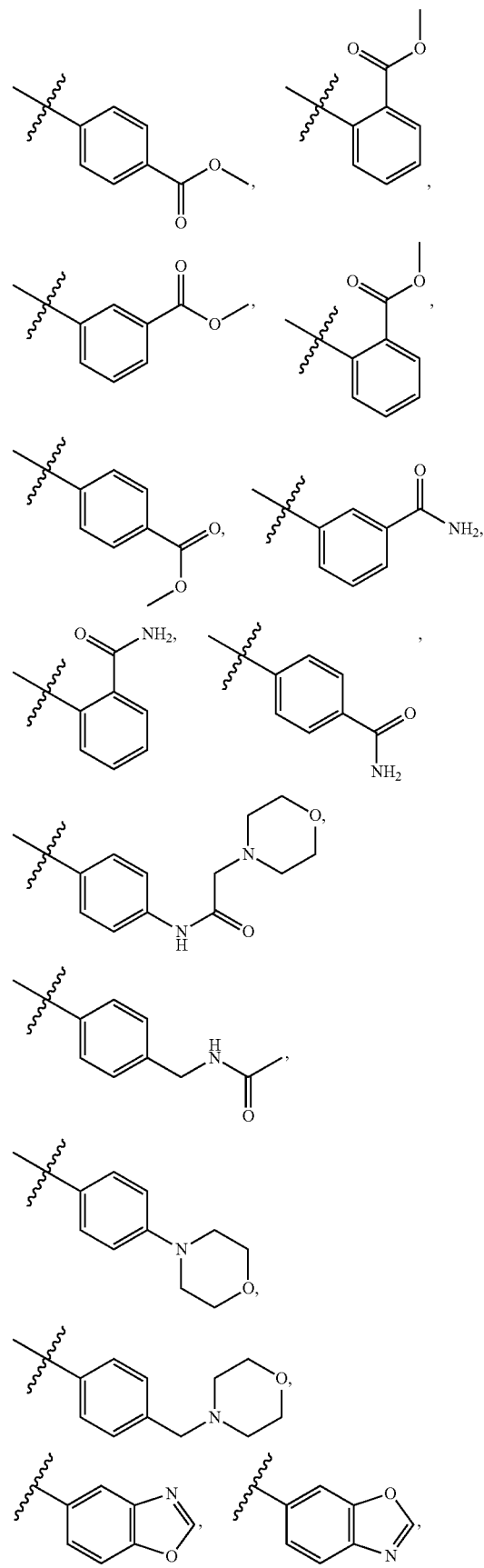

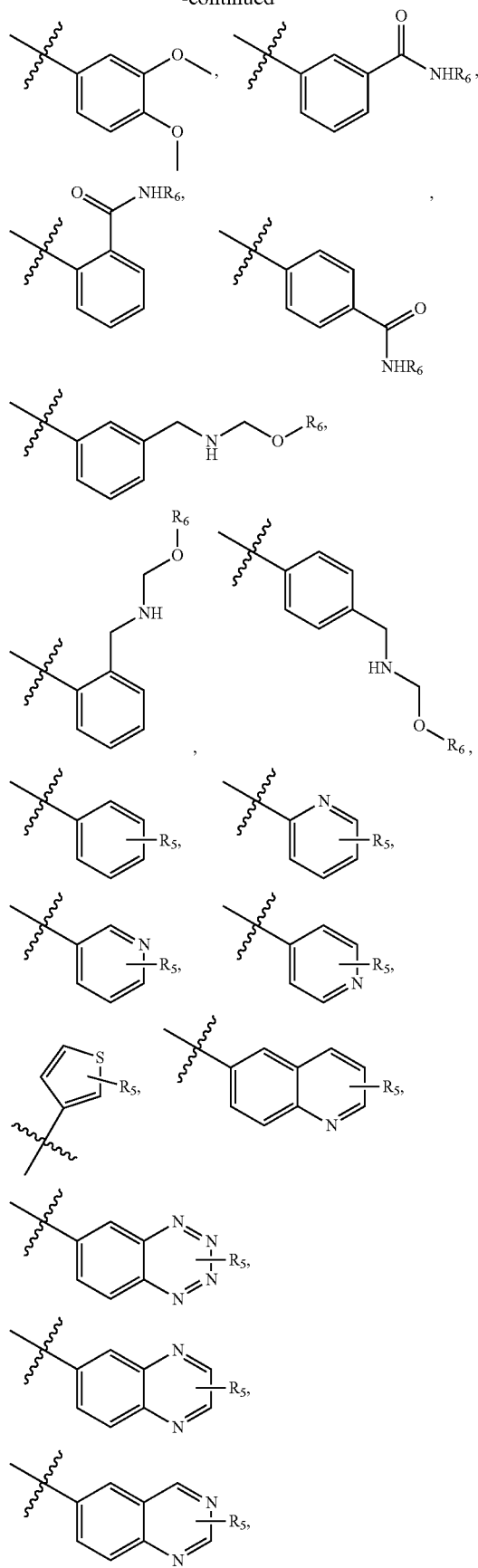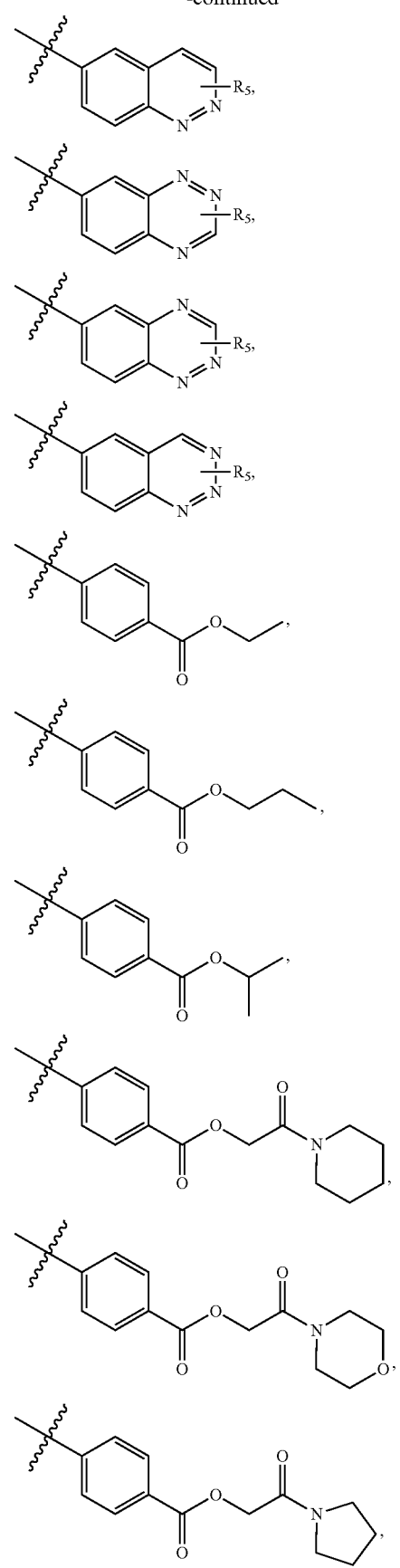

-continued

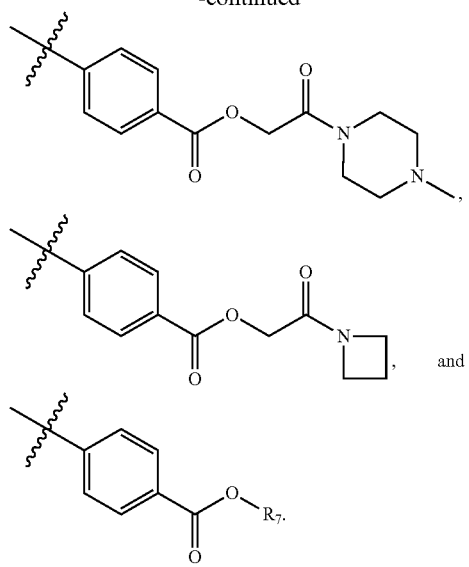

In some embodiments, R1 is an heteroaryl ring.

In some embodiments, R5 is an acidic bio-isostere. For example, in some embodiments R5 is selected from

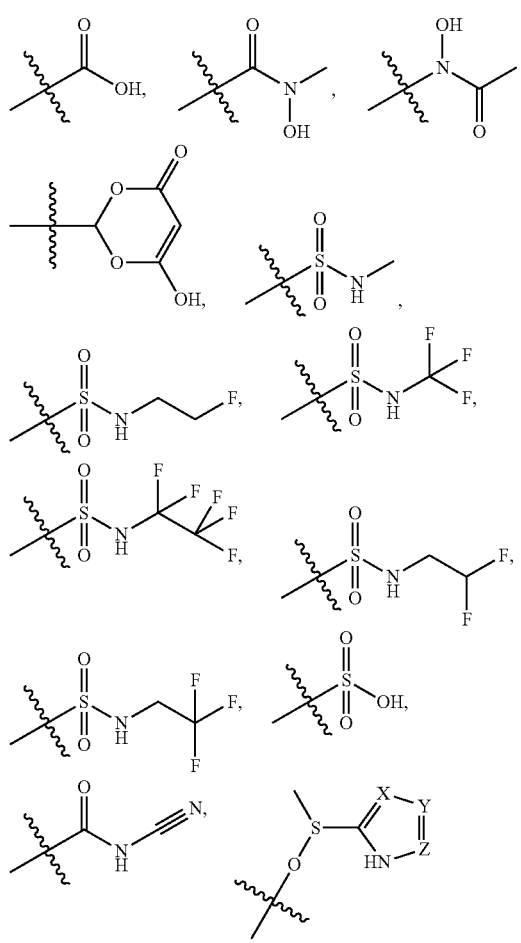

(wherein X, Y, Z are independently N, C or CO),

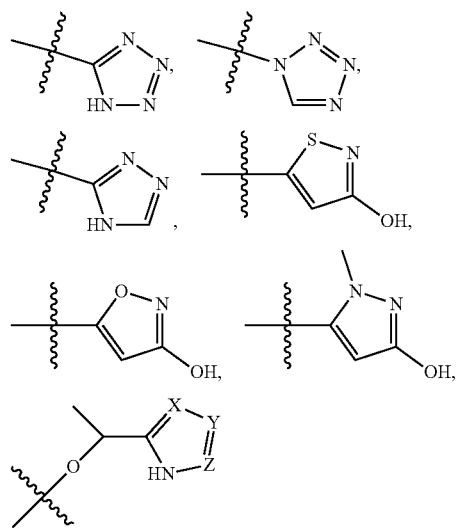

(wherein X, Y, Z are independently N, C or CO),

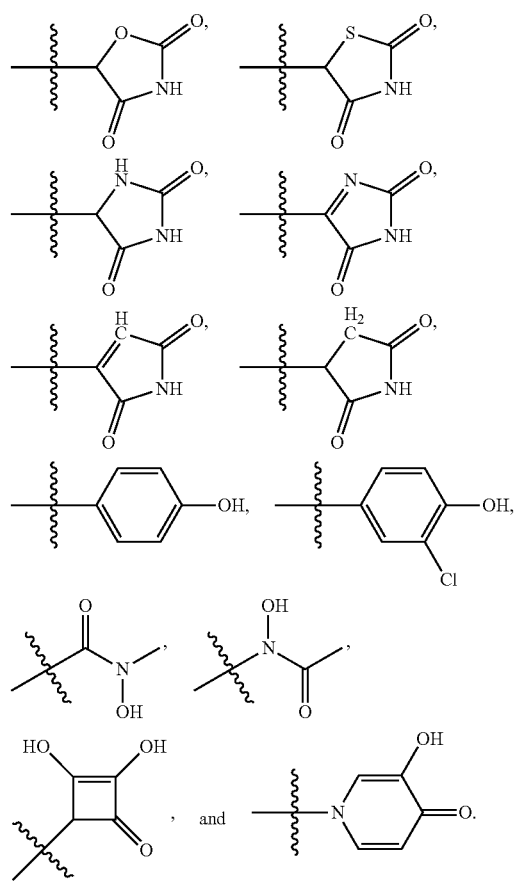

In some embodiments, R5 is selected from hydrogen, alkoxy, alkylsulfonyl, cyano, carboxy, ester, amido, substituted amido, sulfonamide, substituted sulfonamide, methylenedioxy, heterocyclyl alkyl, heterocyclyl, and heterocyclyl alkyl amido, a lipophilic moiety comprising ether functionality, methyl, ethyl, $(CH_2)_3$,

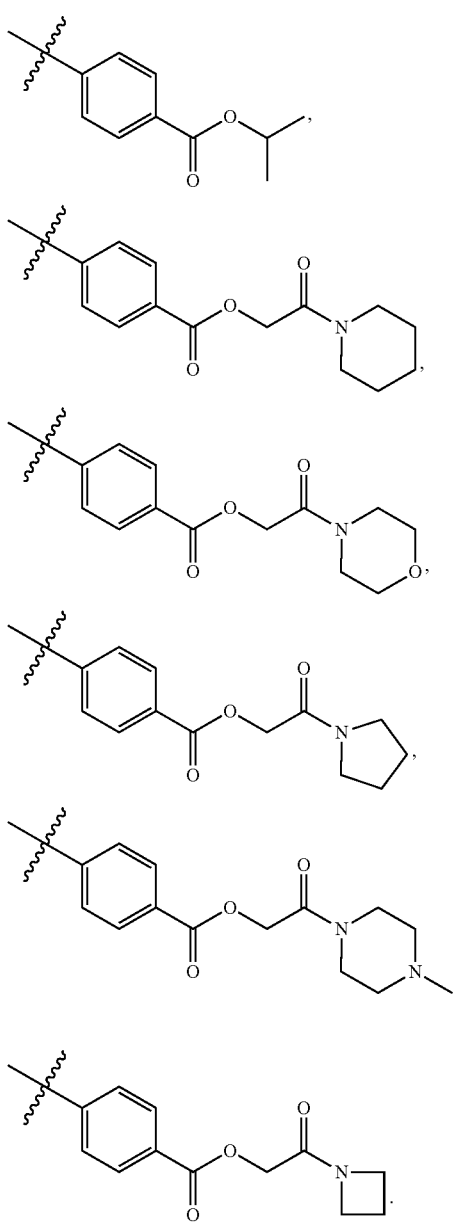

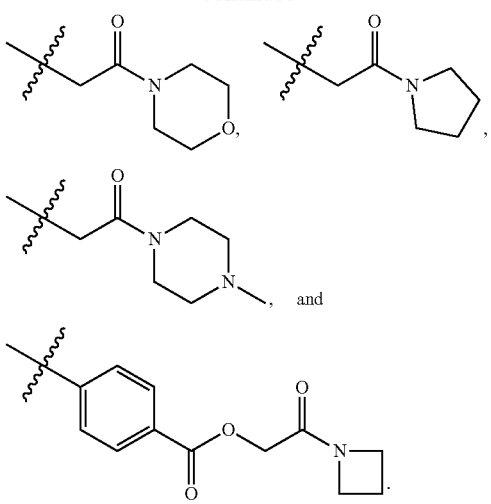

In some embodiments, each of R2 and R3 is independently selected from hydrogen, aryl, substituted aryl, heteroaryl, substituted heteroaryl,

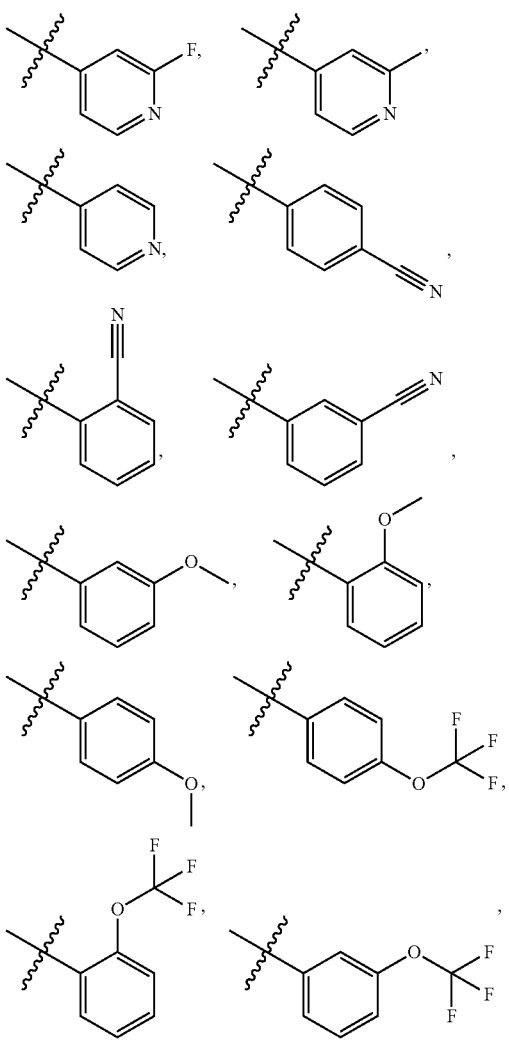

In some embodiments, R6 is selected from hydrogen, C1-C4 alkyl, heterocyclyl alkyl, heteroaryl alkyl, aryl alkyl, aryl, heterocyclyl, and heteroaryl.

In some embodiments, R7 is selected from hydrogen, alkoxy, alkylsulfonyl, cyano, carboxy, ester, amido, substituted amido, sulfonamide, substituted sulfonamide, methylenedioxy, heterocyclyl alkyl, heterocyclyl, and heterocyclyl alkyl amido, a lipophilic moiety comprising ether functionality, methyl, ethyl, $(CH_2)_3$,

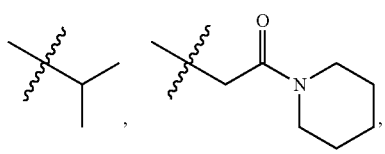

-continued
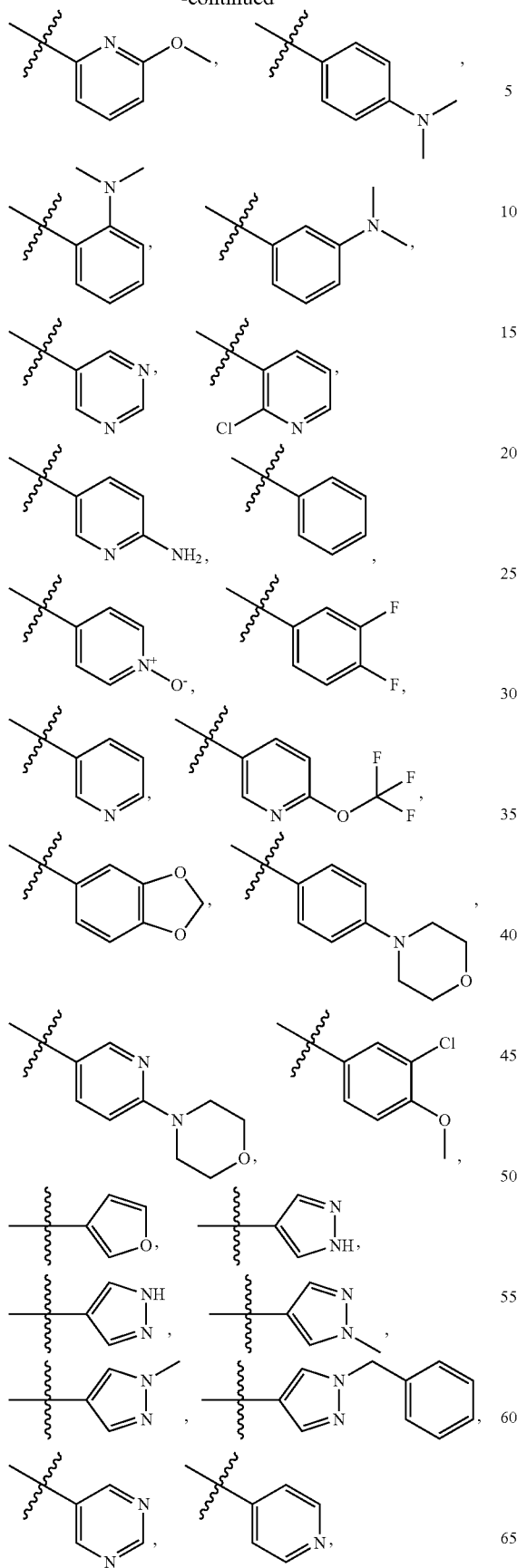
-continued
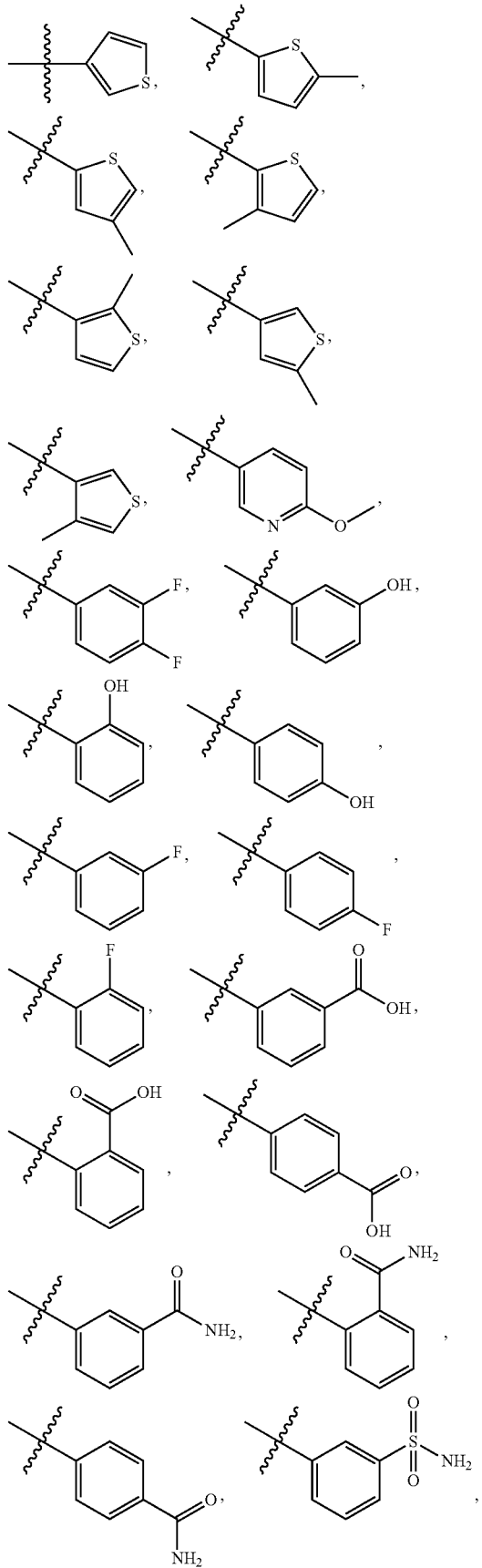

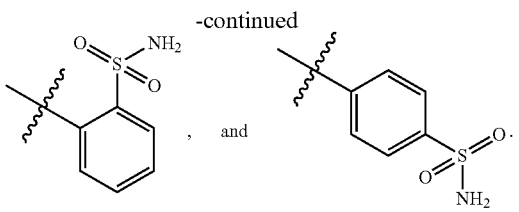

In some embodiments, R4 is selected from hydrogen, NH₂,

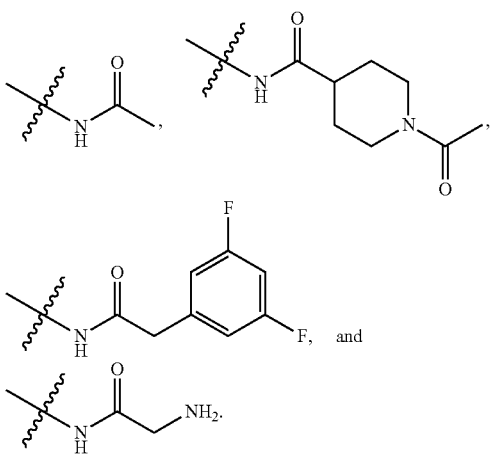

In some embodiments, the compound is selected from

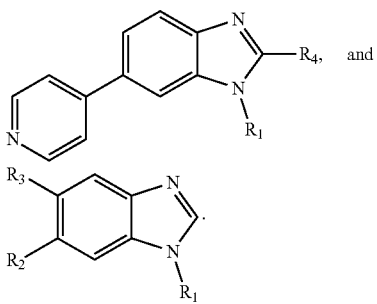

In some embodiments, the compound is one or more of the compounds shown in Examples II and/or III.

The invention further provides processes for preparing any of the compounds of the present invention.

The invention also provides the use of compounds to not only inhibit DYRK1A activity but also signaling pathways dependent upon DYRK1A phosphorylation (e.g., Tau, PI3K/AKt, APP, PSI, ASF, RCAN-1, NFAT, p53, ASK1/JNK1, SIRT1, GluN2A and other NMDA receptors). The invention also relates to the use of compounds for sensitizing cells to additional agent(s), such as agents known to be effective in the treatment of neurodegenerative disorders.

The compounds of the invention are useful for the treatment, amelioration, or prevention of disorders associated with DYRK1A activity (e.g., AD, DS, Parkinson's disease, Huntington's disease, glioblastoma), such as those responsive to DYRK1A activity inhibition. In certain embodiments, the compounds can be used to treat, ameliorate, or prevent cancer that is associated with DYRK1A activity (e.g., glioblastoma). In certain embodiments, the compounds can be used to treat, ameliorate, or prevent autoimmune diseases. In certain embodiments, the compounds can be used to treat, ameliorate, or prevent inflammatory disorders (e.g., airway inflammation).

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., agents useful in treating neurodegenerative disorders and/or anticancer agents.

In a particular embodiment, compounds encompassed within the following formula are provided:

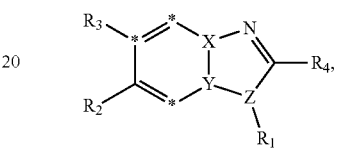

including pharmaceutically acceptable salts, solvates, and/or prodrugs thereof. In such embodiments, each of the "*" substituents is independently Carbon or Nitrogen, and X, Y, Z, R1, R2, R3, and R4 are as described above.

DETAILED DESCRIPTION OF THE INVENTION

Figure 1:
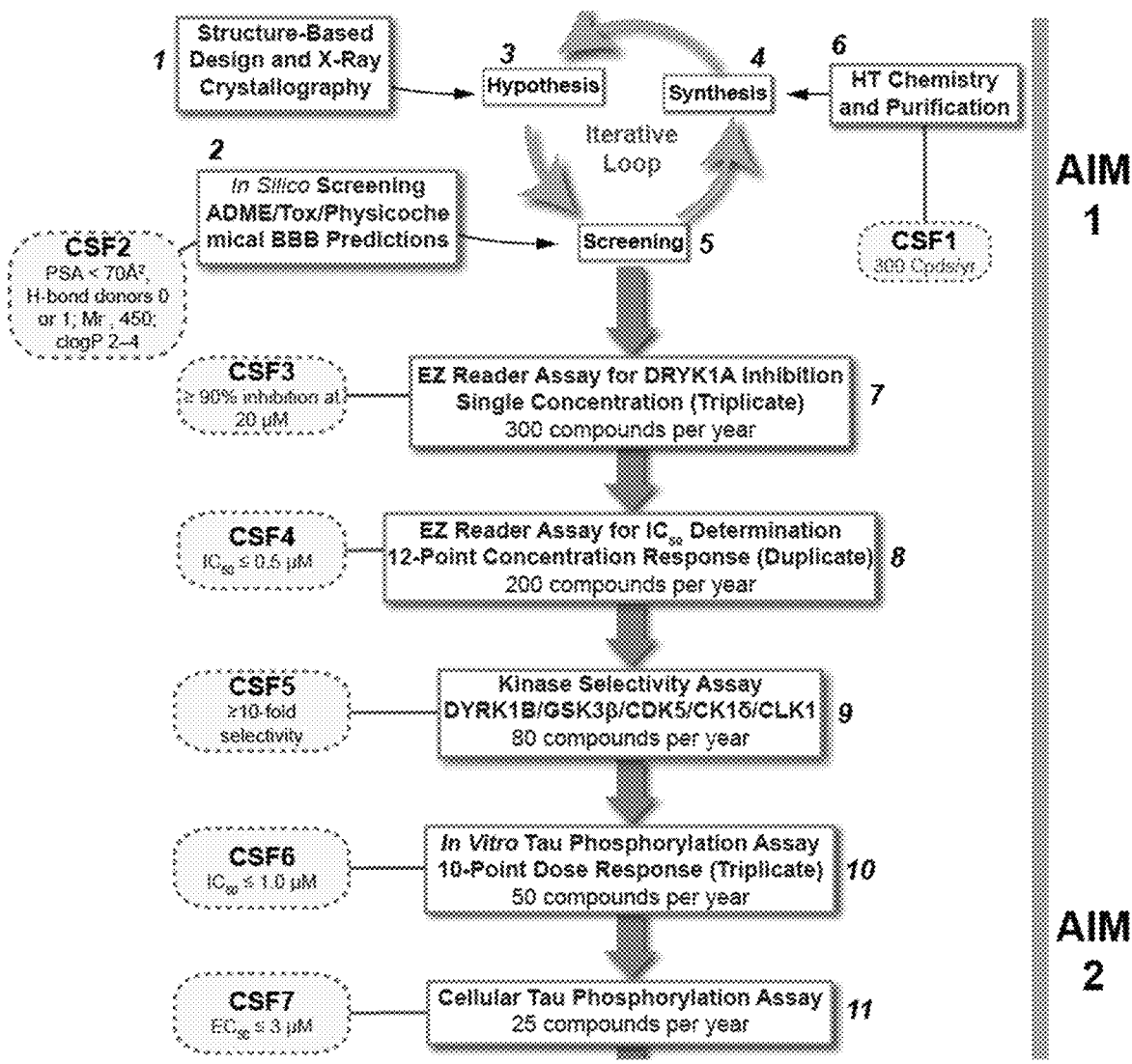
FIG. 1 presents a flow chart describing a screening paradigm for DYRK1A inhibitor progression.
Figure 1:
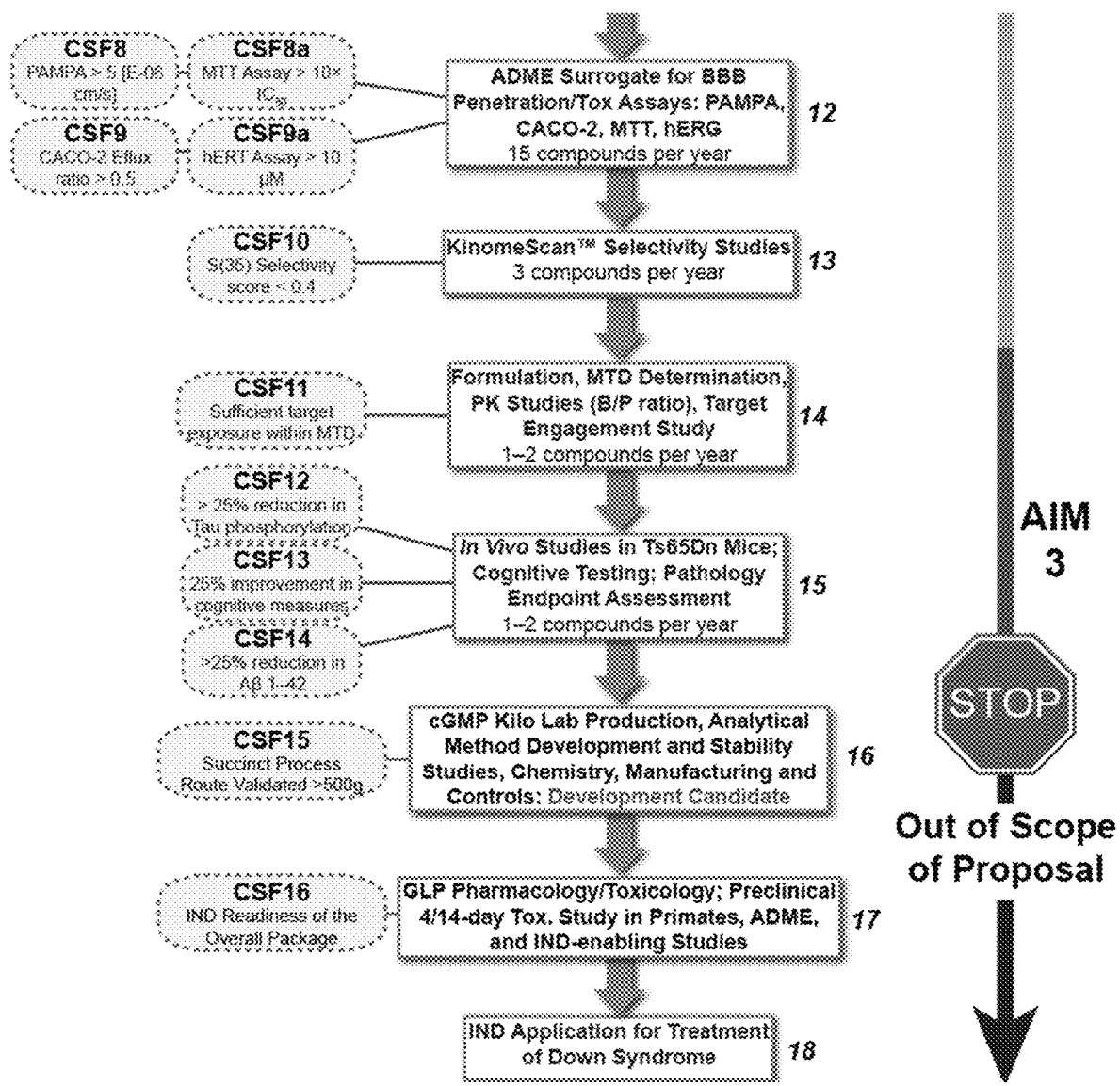

DYRK1A is a member of the DYRK family containing 5 kinases (DYRK1A, DYRK1B, DYRK2, DYRK3 and DYRK4). DYRKs belong to the CMGC group of proline-directed kinases, which also includes cyclin-dependent kinases (CDKs), mitogen-activated protein kinases (MAPKs), glycogen synthase kinases (GSKs) and CDC2-like kinases (CLKs). While the signaling pathways of CDK and MAPK families have been extensively studied, much less is known on how DYRKs and CLKs are linked to other proteins and various physiological or pathological processes.

The DYRK1A gene is located on chromosome 21 (21q22.2), a region known as the Down-Syndrome Critical Region (DSCR) (see, e.g., Hämmerle et al., 2011 Development 138, 2543-2554). The under- or over-expression of the Dyrk1a gene in mammals or of its orthologous gene mini-brain (mnb) in Drosophila causes severe retardation of central nervous system development and maturation. At the molecular level, DYRK1A phosphorylates the nuclear factor of activated T cells (NFAT), counteracting the effect of calcium signaling and maintaining inactive NFAT (see, e.g., Arron et al., 2006 Nature 411, 595-600). DYRK1A has been identified as a negative regulator of the cell cycle that promotes the switch to a quiescent state or differentiation (see, e.g., Chen et al., 2013 Mol. Cell 52, 87-100). In malignant cells, DYRK1A promotes survival via inhibition of pro-apoptotic proteins (see, e.g., Guo et al., 2010 J. Bio. Chem. 285, 13223-13232; Seifert et al., 2008 FEBS J. 275, 6268-6280).

Currently, treatment options for cognitive deficiencies associated with AD and DS are extremely limited and represent a major, extremely significant unmet therapeutic need. The DYRK1A inhibitors of the present invention provide a new avenue for pharmaceutical intervention of mental impairment associated with AD and other neurodegenerative diseases, and address a critical unmet medical need and significantly changing treatment paradigm for AD.

Experiments conducted during the course of developing embodiments for the present invention designed, synthesized and biologically evaluated benzimidazole and imidazopyridine compounds as inhibitors of the dual specificity tyrosine phosphorylation regulated kinase-1A (DYRK1A) and their potential for use as therapeutics against AD and other disorders related to DYRK-1A activity (e.g., DS, other neuropathology, cancer (e.g., glioblastoma)). Many benzimidazole and imidazopyridine compounds were also shown to exhibit activity against DYRK1B and exhibit some degree of activity against other kinases implicated in a variety of disease states.

Moreover, the DYRK1A inhibitors of the present invention can be used for treating other cellular pathways involved in mental impairment and neurodegenerative dementia. Specifically, the DYRK1A inhibitors of the present invention can be used for inhibiting DYRK1A activated PI3K/Akt signaling, a pathway largely involved in neuronal development, growth, and survival. The DYRK1A inhibitors of the present invention DYRK1A can be used for inhibiting DYRK1A stimulated ASK1/JNK1 activity, thereby inducing neuronal death and apoptosis. In addition, the DYRK1A inhibitors of the present invention DYRK1A can be used to inhibit DYRK1A phosphorylation of p53 during embryonic brain development, thereby preventing neuronal proliferation alteration. The DYRK1A inhibitors of the present invention can be used to inhibit DYRK1A phosphorylation of synaptic proteins Amph 1, Dynamin 1, and Synaptojanin, involved in the regulation of endocytosis, thereby retaining synaptic plasticity through preventing alteration of the number, size, and morphology of dendritic spines. The DYRK1A inhibitors of the present invention can be used to inhibit presenilin 1 (the catalytic sub-unit of γ-secretase).

As such, the present invention addresses the need for effective therapies for AD and DS by providing potent and selective DYRK1A inhibitors able to permeate the blood-brain barrier (BBB) and elicit on-mechanism therapeutic responses in AD animal models.

Accordingly, this invention relates to a new class of small-molecules having a benzimidazole or imidazopyridine structure which function as inhibitors of DYRK1A protein, and their use as therapeutics for the treatment of Alzheimer's disease, Down syndrome, glioblastoma, autoimmune diseases, inflammatory disorders (e.g., airway inflammation), and other diseases.

In a particular embodiment, benzimidazole and imidazopyridine compounds encompassed within Formula I are provided:

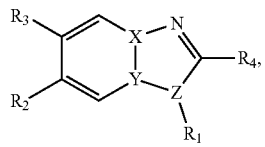

including pharmaceutically acceptable salts, solvates, and/or prodrugs thereof.

Formula I is not limited to a particular chemical moiety for R1, R2, R3, R4, X, Y and Z. In some embodiments, the particular chemical moiety for R1, R2, R3, R4, X, Y and Z independently include any chemical moiety that permits the resulting compound to inhibit DYRK1A activity. In some embodiments, the particular chemical moiety for R1, R2, R3, R4, X, Y and Z independently include any chemical moiety that permits the resulting compound to inhibit one or more of: DYRK1A related PI3K/Akt signaling; DYRK1A related tau phosphorylation; DYRK1A related NFAT phosphorylation; DYRK1A related ASK1/JNK1 pathway activation; DYRK1A related p53 phosphorylation; DYRK1A related Amph 1 phosphorylation; DYRK1A related Dynamin 1 phosphorylation; DYRK1A related Synaptojanin phosphorylation; DYRK1A related presenilin 1 (the catalytic sub-unit of γ-secretase) activity; DYRK1A related amyloid precursor protein phosphorylation; and DYRK1A related SIRT1 activation.

In some embodiments, X—Y—Z is

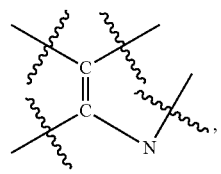 [SMILES: *NC(*)=C(*)*]

thereby rendering the resulting compound a benzimidazole compound having the following formula:

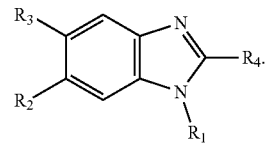

In some embodiments, X—Y—Z is

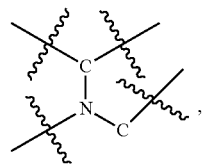 [SMILES: *CN(*)C(*)*]

thereby rendering the compound an imidazopyridine compound having the following formula:

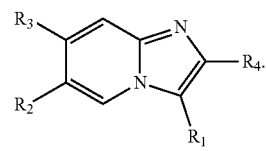

In some embodiments, R1 is selected from hydrogen, aryl and substituted aryl,

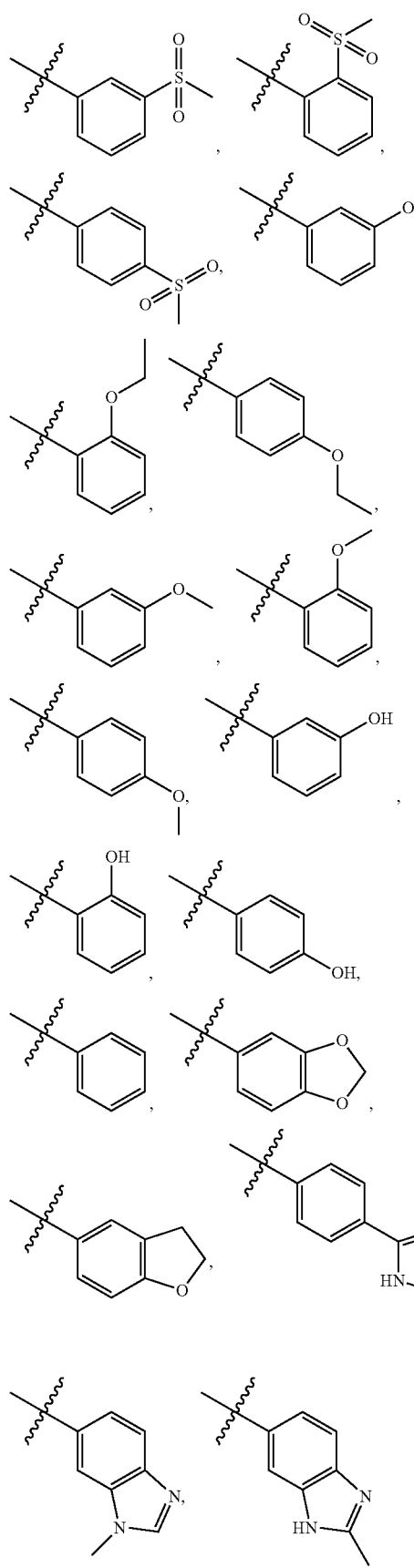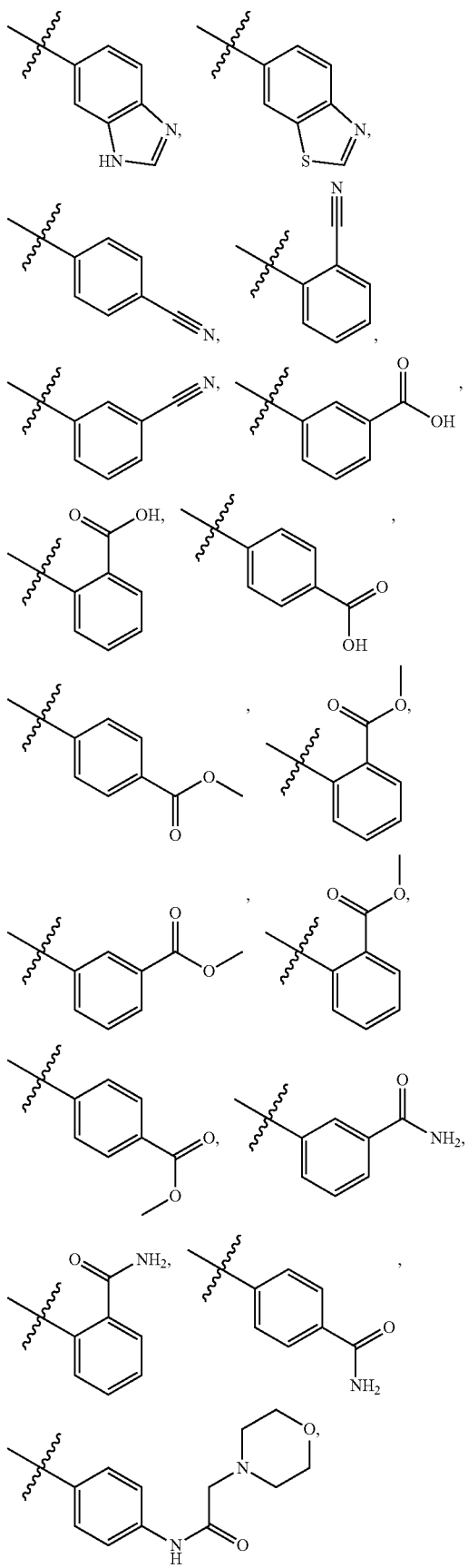

-continued
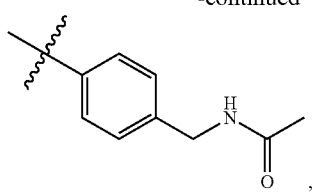
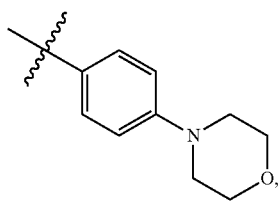
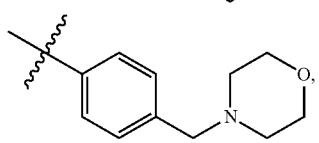
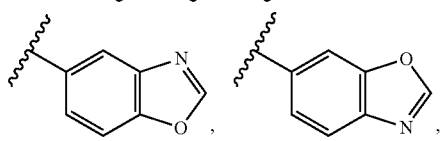
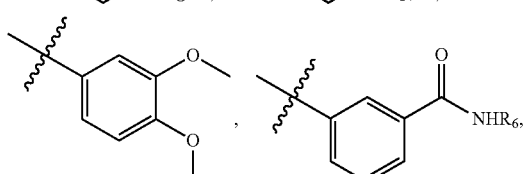
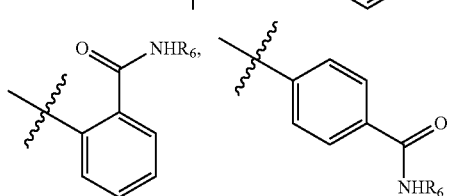
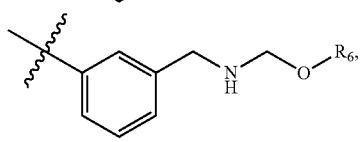
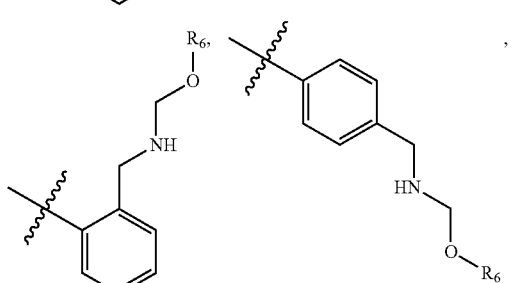
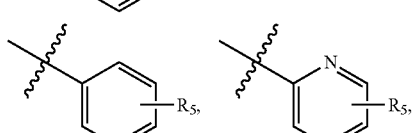
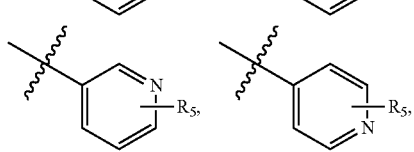
-continued
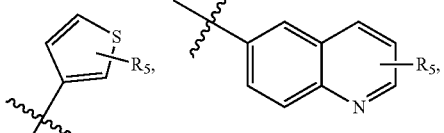
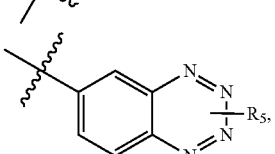
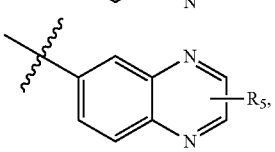
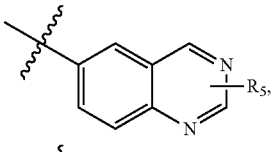
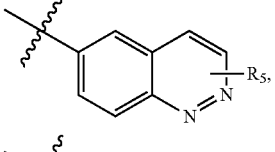
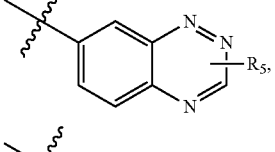
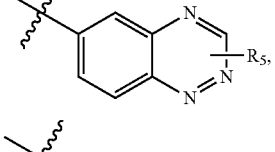
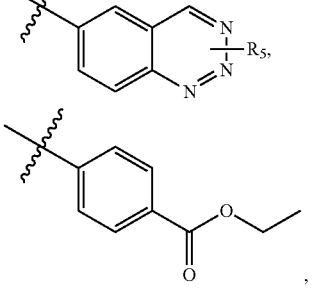
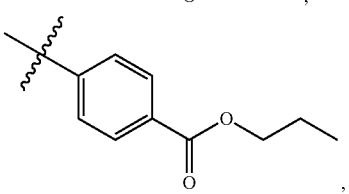
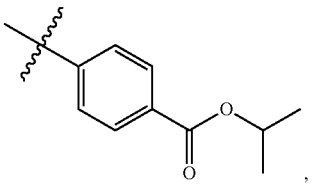

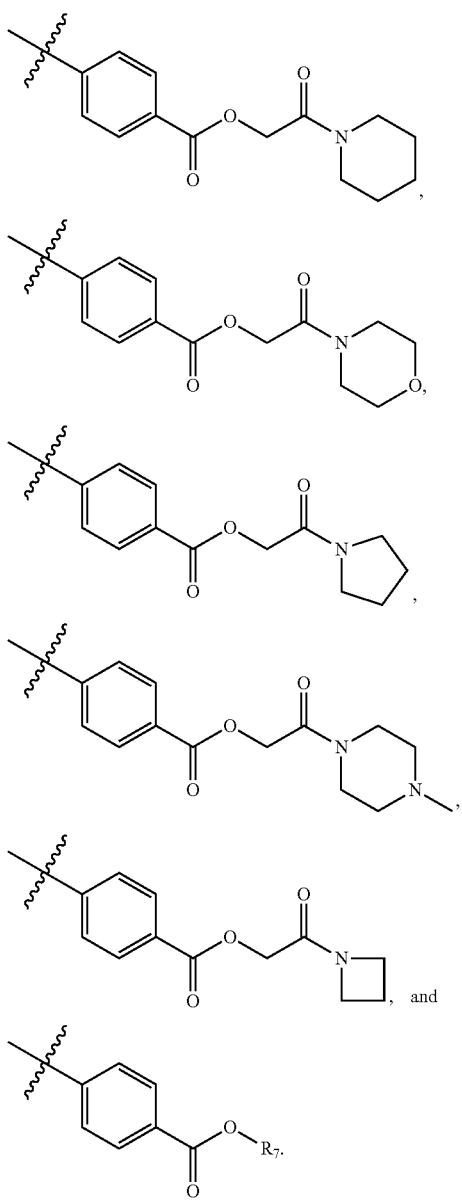
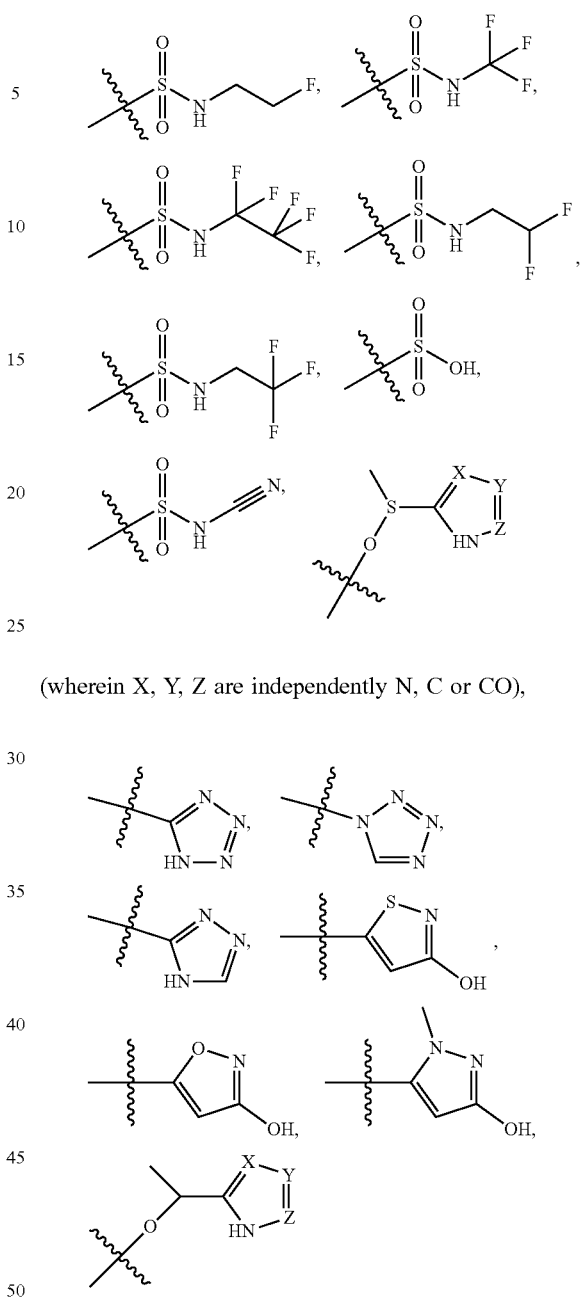
(wherein X, Y, Z are independently N, C or CO),
In some embodiments, R1 is a heteroaryl ring.
In some embodiments, R5 is an acidic bio-isostere. For example, in some embodiments R5 is selected from
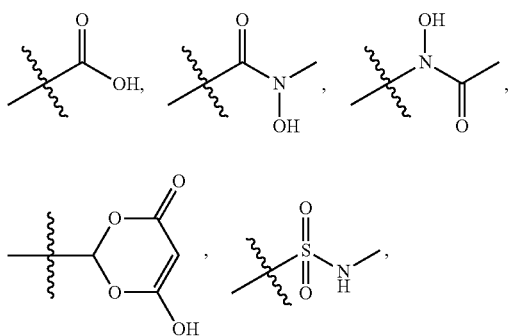
(wherein X, Y, Z are independently N, C or CO),
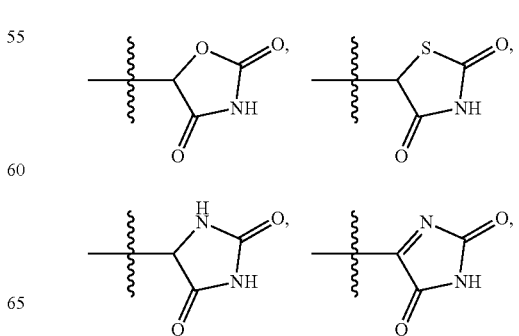

-continued

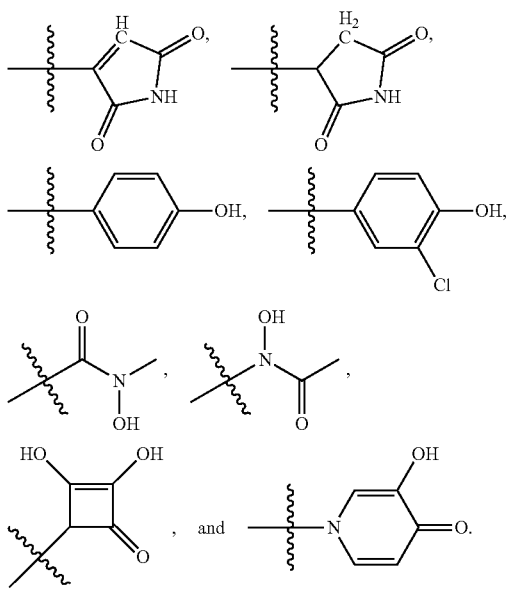

In some embodiments, R5 is selected from hydrogen, alkoxy, alkylsulfonyl, cyano, carboxy, ester, amido, substituted amido, sulfonamide, substituted sulfonamide, methylenedioxy, heterocyclyl alkyl, heterocyclyl, and heterocyclyl alkyl amido, a lipophilic moiety comprising ether functionality, methyl, ethyl, $(CH_2)_3$,

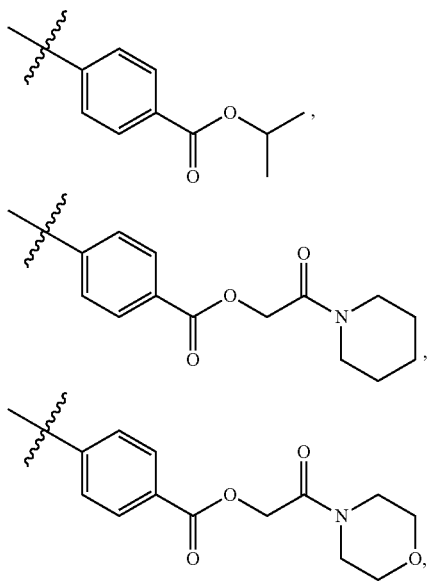

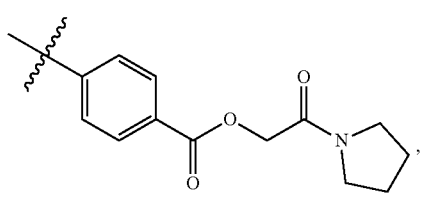

-continued

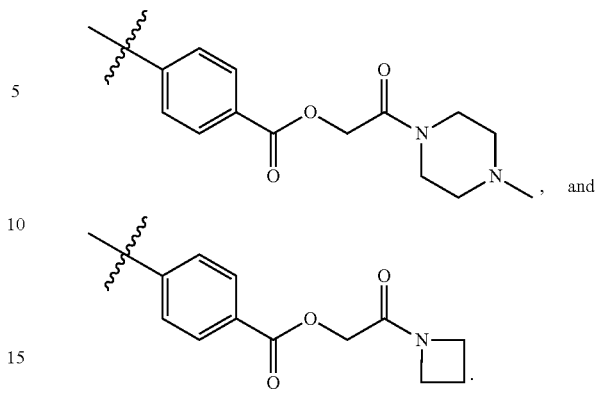

In some embodiments, R6 is selected from hydrogen, C1-C4 alkyl, heterocyclyl alkyl, heteroaryl alkyl, aryl alkyl, aryl, heterocyclyl, and heteroaryl.

In some embodiments, R7 is selected from hydrogen, alkoxy, alkylsulfonyl, cyano, carboxy, ester, amido, substituted amido, sulfonamide, substituted sulfonamide, methylenedioxy, heterocyclyl alkyl, heterocyclyl, and heterocyclyl alkyl amido, a lipophilic moiety comprising ether functionality, methyl, ethyl, $(CH_2)_3$,

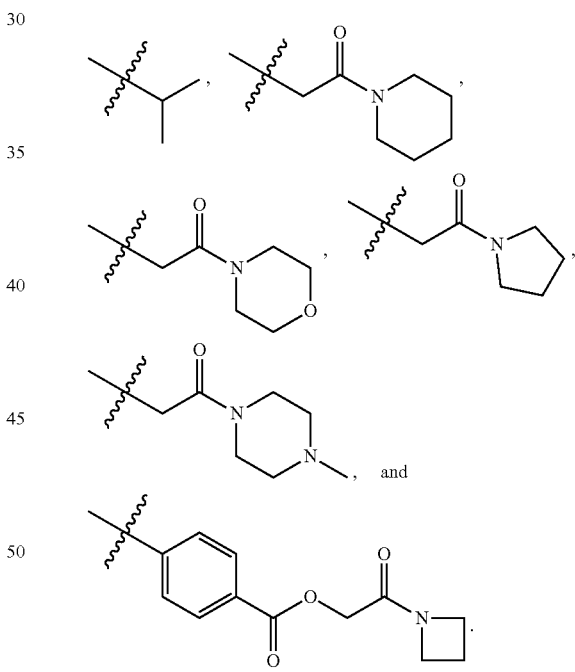

In some embodiments, each of R2 and R3 is independently selected from hydrogen, aryl, substituted aryl, heteroaryl, substituted heteroaryl,

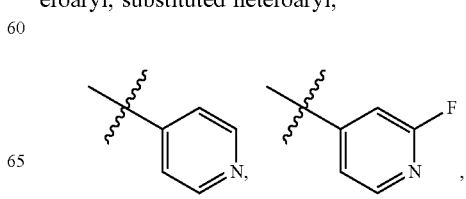

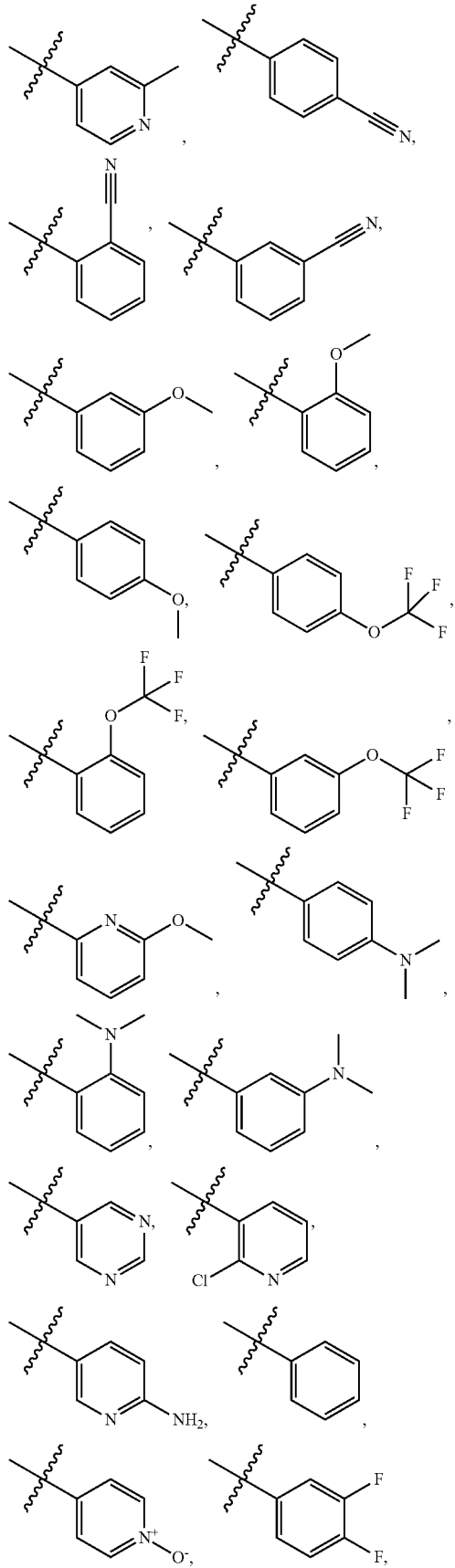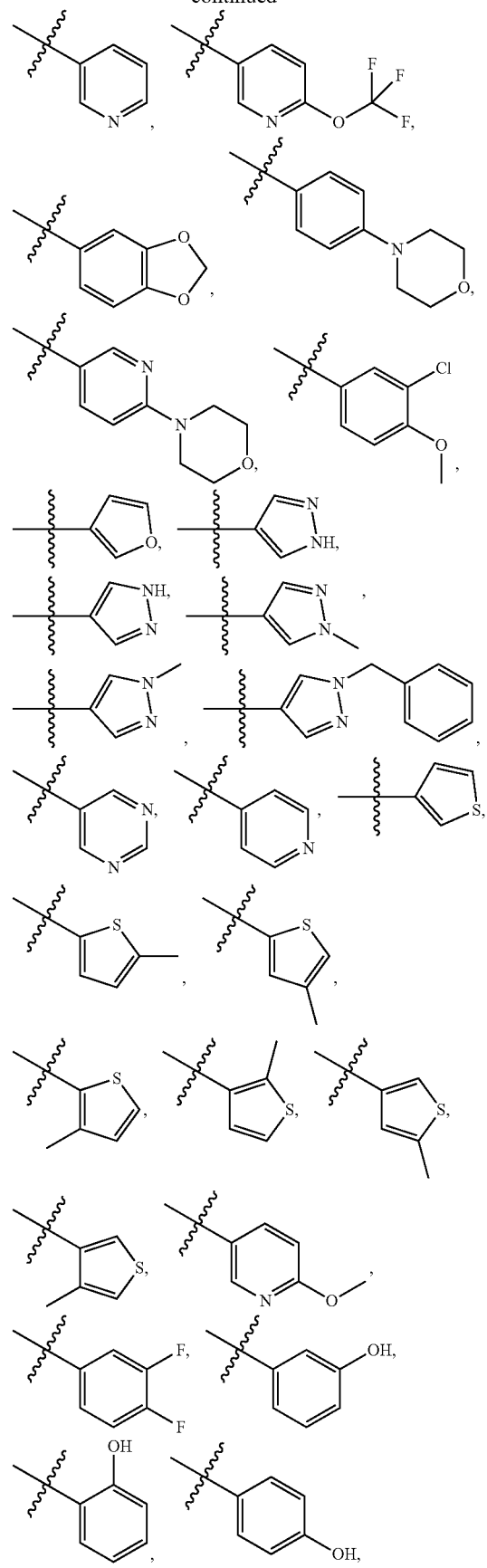

-continued

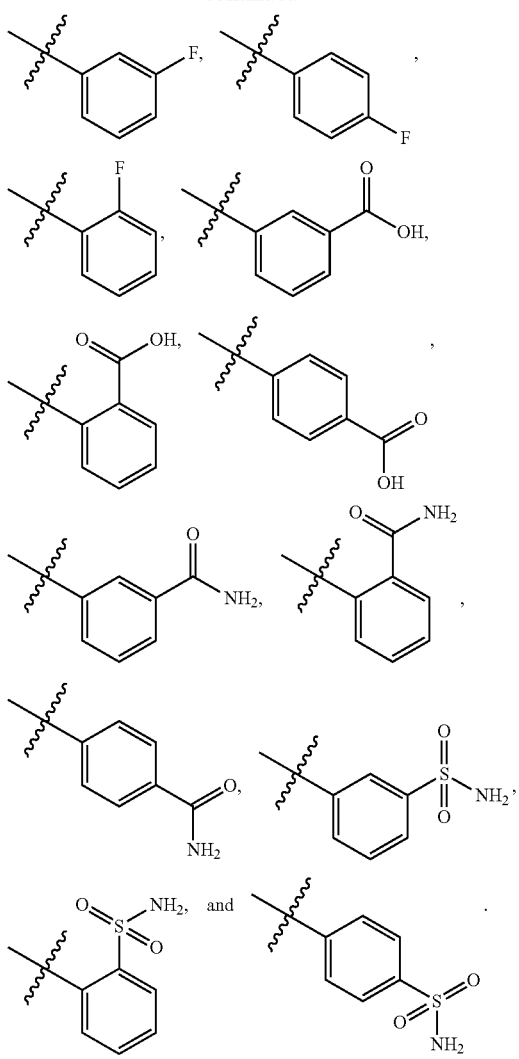

In some embodiments, R4 is selected from hydrogen, NH₂,

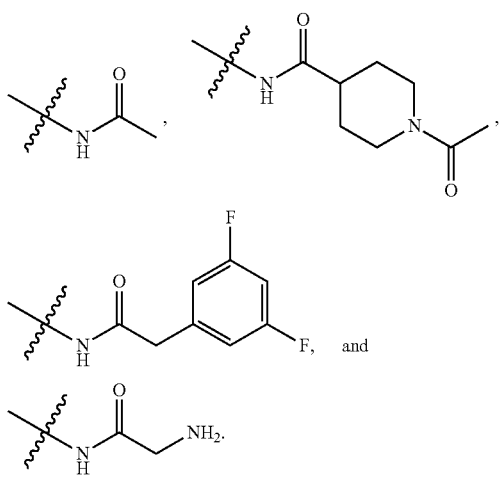

In some embodiments, the compound is selected from

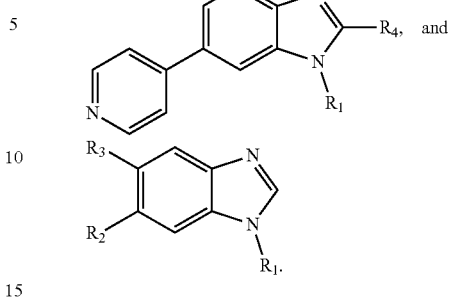

In some embodiments, the compound is one or more of the compounds shown in Examples II and/or III.

The invention further provides processes for preparing any of the compounds of the present invention.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, Alzheimer's disease, Down syndrome, Huntington's disease, Parkinson's disease, autoimmune diseases, inflammatory disorders (e.g., airway inflammation), any neurodegenerative disorder related to DYRK1A activity, and any type of cancer related to DYRK1A activity.

Some embodiments of the present invention provide methods for administering an effective amount of a compound of the invention and at least one additional therapeutic agent (including, but not limited to, any agent useful in treating Alzheimer's disease, Down syndrome, Huntington's disease, Parkinson's disease, autoimmune diseases, inflammatory disorders (e.g., airway inflammation), any neurodegenerative disorder related to DYRK1A activity, and any type of cancer characterized related to DYRK1A activity).

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

Human chromosome 21 trisomy (HSA21) results in Down syndrome (DS) (OMIM 190685) and is one of the most common human chromosomal disorders, occurring in ~1 in 700 live births. While the trisomy usually affects every tissue, reduced cognitive ability is among the most limiting features (see, Lott I T, et al., Lancet neurology 2010; 9:623-633; Megarbane A, et al., Genet Med 2009; 11:611-616). Therapies that address cognitive restrictions of DS could have a significant impact for individuals living with this disorder. To this end, normalizing expression levels or the function of critical genes on chromosome 21 could prevent or reverse the deleterious effects of gene overdose.

Three main murine models for DS have been developed (Ts65Dn (see, Reeves R H, et al., Nat Genet 1995; 11:177-184), Ts1Cje (see, Sago H, et al., PNAS 1998; 95:6256-6261), and Ts1Rhr (see, Belichenko N P, et al., J Neurosci 2009; 29:5938-5948)) that exhibit partial trisomy of chromosome 16, the murine ortholog to human chromosome 21. In all three models, the trisomic region of MMU16 contains the gene for dual-specificity tyrosine-(Y)-phosphorylation regulated kinase 1A (DYRK1A), a member of the CMGC family of kinases. These mice show characteristic symptoms of DS including learning and behavioral deficits (see, Reeves R H, et al., Nat Genet 1995; 11:177-184; Sago H, et al., PNAS 1998; 95:6256-6261; Belichenko N P, et al., J Neurosci 2009; 29:5938-5948) and alterations in their dendritic spines within the hippocampus and cortical regions of the brain (see, Belichenko N P, et al., J Neurosci 2009; 29:5938-5948; Belichenko P V, et al., J Comp Neurol 2004; 480:281-298; Belichenko P V, et al., J Comp Neurol 2007; 504:329-345; Siarey R J, et al., Neuropharmacology 2005; 49:122-128; Smith D J, et al., Nat Genet 1997; 16:28-36). Transgenic mice have also been prepared using a yeast artificial chromosome YAC 152F7 bearing extra copies of five different genes found in the DS critical region (DSCR) of human chromosome 21 including DYRK1A, PIGP, TTC3, DSCR9, and DSCR3. These mice demonstrate significantly impaired learning ability and brain abnormalities (see, Smith D J, et al., Nat Genet 1997; 16:28-36; Branchi I, et al., J Neuropathol Exp Neurol 2004; 63:429-440; Chabert C, et al., Behav Genet 2004; 34:559-569). In comparison, murine models transgenic for the yeast artificial chromosome YAC 141G6 which contains all genes encompassed in YAC 152F7 except DYRK1A do not exhibit noticeable cognitive impairment. In addition, mouse models that are transgenic for the human BAC gene (DYRK1A BAC Tg) or a murine BAC clone (TgDYRK1A) have been generated that specifically overexpress either human or murine DYRK1A, respectively. These mice similarly exhibit DS phenotypes including hippocampal-dependent spatial learning and motor deficits and developmental delays, which is highly suggestive of a central function for DYRK1A in mental deficits associated with DS (see, Smith D J, et al., Nat Genet 1997; 16:28-36; Ahn K J, et al., Neurobiol Dis 2006; 22:463-472; Altafaj X, et al., Hum Mol Genet 2001; 10:1915-1923). Cognitive impairment and dendritic tree alteration in TgDyrk1A recapitulates that of Ts65Dn mice (see, Ahn K J, et al., Neurobiol Dis 2006; 22:463-472; Altafaj X, et al., Hum Mol Genet 2001; 10:1915-1923). These combined observations indicate that DYRK1A overexpression is necessary and sufficient for cognitive abnormalities of DS and that normalization of DYRK1A activity is a promising therapeutic approach for this genetic disorder.

Harmine 3 is a β-carboline alkaloid with a reported $IC_{50}$ of 80 nM against DYRK1A (see, Bain J, et al., Biochem J 2003; 371:199-204; Bain J, et al., Biochem J 2007; 408:297-315). Despite high affinity for DYRK1A, β-carboline analogues, including harmine, have significant drawbacks to consider when exploring their potential therapeutic applications. The hallucinogenic properties of harmine have been exploited historically (see, Callaway J C, et al., J Ethnopharmacol 1999; 65:243-256; Gambelunghe C, et al., Biomed Chromatogr 2008; 22:1056-1059) and more recently shown to be the result of its affinity for the serotonin and tryptamine receptor binding sites (see, Airaksinen M M, et al., Pharmacol Toxicol 1987; 60:5-8). Animal studies conducted on the β-carbolines as early as the 1930s revealed a plethora of psychoactive effects including excitation, anxiety, tremors, convulsions, ataxia, pupil dilation, and alterations in the brain's electrical activity (electroencephalographic activity or EEG activity) (see, Fuentes J A, et al., Neuropharmacology 1971; 10:15-23; Kawanishi K, et al., Pharmacol Biochem Behav 1994; 47:689-699). In addition, β-carbolines methylated at the pyridine nitrogen can mimic the activity of the powerful neurotoxic metabolite MPTP. MPTP is converted to MPP+ in the brain, affecting the extrapyramidal dopaminergic system leading to permanent Parkinson's-like symptoms (see, Albores R, et al., PNAS 1990; 87:9368-9372). Due to their convulsive properties observed in vivo, it has been suggested that harmine and its analogues are likely susceptible to similar metabolic pathways. Harmine 3 also exhibits potent inhibition of monoamine oxidase-A (MAO-A) reuptake, leading to behavioral side effects (Ki 5 nM, $IC_{50}$ 2 nM) (see, Reeves R H, et al., Nat Genet 1995; 11:177-184). The deleterious off-target effects of both harmine and EGCg necessitate the development of potent and selective DYRK1A inhibitors for advancing inhibition of this kinase as a therapeutic target for DS. Experiments conducted during the course of developing embodiments for the present invention generated these much needed DYRK1A inhibitors.

A goal of such experiments was to deliver two advanced leads from innovative, structurally distinct chemical platforms worthy of evaluation in a GLP/GMP modality through critical success factors (CSFs) 15 & 16, Boxes 16-18 (FIG. 1). New molecules with the potential to improve the lives of patients with DS and other indications claimed herein have emerged. FIG. 1 simply represents one flow chart which can be modified with alternate in vivo studies/models for the other indications claimed herein.

At all times, several guiding principles correlating BBB penetration with physicochemical properties of CNS-active drugs were closely monitored. Key properties with preferred ranges for small-molecule BBB passive diffusion include molecular weight (MW≤450); polar surface area ($^t$PSA≤70 Å$^2$); log P or D (2-4), and H-bond donor count (HBD≤1) (CSF2, Box 2, FIG. 1) (see, Hitchcock S A, J. Med. Chem., 2006, 49(26), 7559-83).

At the beginning of this effort, three DYRK1A inhibitor-bound crystal structures were available: harmine (PDB ID: 3ANR) 3, INDY (PDB ID: 3ANQ) 6, and D15 (PDB ID: 2WO6) 7 (www.rcsb.org). Knowledge based approaches utilizing this information ultimately lead to the discovery described herein.

Isoform selectivity with DYRK1B is a challenge due to high homology with 1A, although no evidence exists to suggest this will be detrimental to the therapeutic index of a DRYK1A inhibitor and preliminary data suggests selectivity is achievable. Moreover, DYRK1B is over-expressed in certain cancer cells including colon, ovarian and pancreatic and could be an attractive target for cancer therapy (see, Deng X, et al., Genes & Cancer (2014), 5(9-10), 337-347; Berger F, et al., Ger. Offen. (2014), DE 102014009011 A1 20141218; Anderson K, et al., Bioorg. Med. Chem. Lett., 2013, 23(24), 6610-6615). There exists 27 FDA approved small molecule kinase-inhibiting drugs, and encouragingly the 2012 approval of Tofacitinib, a JAK3 inhibitor for rheumatoid arthritis, adds extra impetus to the feasibility of successfully targeting kinases for non-oncology related indications (see, Cohen, P. Nat. Rev. Drug Discov., 2002, 1(4), 309-315; Roskoski, R. USFDA approved protein kinase inhibitors. Blue Ridge Institute for Medical Research. Horse Shoe, N.C. www.brimr.org/PKI/PKIs.htmL).

To utilize a medium-throughput in vitro phosphorylation assay with recombinant DYRK1A to determine % inhibition and triage actives for $IC_{50}$ determination. (CSF 3 & 4, Box 7 & 8, FIG. 1). The DYRK1A kinase assay utilizes an EZ Reader Electrophoresis Mobility Chip Instrument (Caliper Life Science). In the assay, 8.7 nM recombinant DYRK1A enzyme (Invitrogen) is pre-incubated with the small molecule inhibitor, or control buffer, for 5-10 min. To date, these classes of inhibitors are directly competitive with ATP. After 5-10 minutes of pre-incubation, a substrate mix containing 100 µM ATP, 20 mM $MgCl_2$, and 3 µM fluorescently labeled substrate peptide (Caliper LS, FL-peptide 24, KKISGRL-SPIM) is added to give a final concentration of 0.8 nM enzyme, 45 µM ATP, 9.1 mM $MgCl_2$, and 1.4 µM substrate peptide within each reaction well. The phosphorylation level of the substrate peptide may then be determined. The assay is performed in a 384-well-plate format in which 112 compounds can be evaluated at a single concentration in triplicate, or 14 compounds can be evaluated at 12 concentrations in duplicate for $IC_{50}$ determination. To triage and evaluate compounds from Aim 2A in relevant selectivity panels, surrogate BBB penetration and cell viability assays and in silico and in vitro toxicology screens: (a) the established in-house selectivity panel (CSF5, Box 9). (b) PAMPA, Caco-2 studies and MTT assays (CSF8, 9 & 8a, Box 12). (c) KinomeScan™ (CSF10, Box 13). (d) hERG activity (CSF9a).

(a) All active compounds passing CSF4 are subject to an initial kinase panel selectivity screen against DYRK1B, GSK3β, CDK5/p25 and CK1δ respectively using the EZ Reader Electrophoresis Mobility Chip Instrument. Rationale for selection is: (i) DYRK1B shows the highest sequence homology (~95%) with DYRK1A, compared to only 43-45% homology to DYRK2/3/4. (ii) GSK3β(see, Hamann, M., et al., J. Nat. Prod., 2007, 70(9), 1397-1405) and CDK5 (see, Ahn J S, et al., Chem. Biol., 2005, 12(7), 811-823) are kinases that also catalyze tau phosphorylation in the brain. (iii) CK1δ mediates various processes in the brain including possible involvement in the glutamate deficiency associated with several neurodegenerative diseases (see, Perez D I, et al., Med. Res. Rev., 2011, 31(6), 924-954). (iv) Clk-1, although not part of the existing panel, will be added as in recent years many DYRK1A inhibitors have been shown to exhibit equipotent affinity for this kinase (see, Tahtouh, T., et al., J Med Chem 2012, 55, 9312-9330; Coombs, T. C., et al., Bioorg Med Chem Lett 2013, 23, 3654-3661). In addition to the pan-inhibitor staurosporine, known inhibitors SB216763 (GSK3β) (see, Nemoto T, et al., Brain Research 2006, 1110(1), 1-12), Roscovitine (CDK5/P25) (see, Oumata N, et al., J. Med. Chem., 2008, 51(17), 5229-5242), PF4800567 (CK1δ) (see, Perez D I, et al., Med. Res. Rev., 2011, 31(6), 924-954), and ML315 (see, Tahtouh, T., et al., J Med Chem 2012, 55, 9312-9330; Coombs, T. C., et al., Bioorg Med Chem Lett 2013, 23, 3654-3661) are/will be employed as standard controls in these assays. Determining activity against these kinases is viewed as key to differentiate functional modes of action of inhibitors in cells.

(b) Compounds progressing to CSF10, Box 13, FIG. 1, are subject to evaluation against a panel of 110 kinases via KinomeScan™ technology (DiscoveRx™), an active-site directed competition binding assay that measures thermodynamic interaction affinities. A selectivity score is determined as the # hits/# kinases tested (see, Details of KinomeScan™ may be found at http://www.discoverx.com/services/drug-discovery-development-services/kinase-profiling/kinomescan). The 110 kinases comprised, the 96 diversity kinase set from DiscoveRx™, with an additional 14 kinases hand-picked for their involvement in CNS diseases. Note that members of the internal selectivity panel are included in the larger KinomeScan™ set.

(c) CACO-2 determinations are performed by Absorption Systems™ using the protocol entitled "P-gp Interaction Assessment in Caco-2 cells" detailed at http://www.absorption.com/p-gp-interaction-assessment-caco-2-cells/.
PAMPA (Parallel Artificial Membrane Permeability Assay) determinations are performed by the CRO Analiza™ with assay details described at http://www.analiza.com/adme/pampa.html. An effective permeability above 2×10-6 cm/sec correlates with a human fraction absorbed (% FA) above 80% and is a common standard for good membrane permeability (CSF8, FIG. 1).

(d) Standard MTT assays are used to measure cytotoxicity (loss of viable cells) of potential DYRK1A inhibitors. The MTT assay is a rapid, high-throughput assay for assessing cell metabolic activity. NAD(P)H-dependent cellular oxidoreductase enzymes reflect the number of viable cells present. These enzymes are capable of reducing the tetrazolium dye MTT 3-(4,5-dimethylthiazol-2-yl)-2,5-diphenyltetrazolium bromide to its insoluble formazan, which has a purple color. Cell viability is, therefore, directly proportional to the production of the purple formazan reaction product (CSF8a, FIG. 1).

(e) Computational assessments of hERG activity (in silico, QikProp-ADME property prediction software Schrodinger Inc.) and patch clamp electrophysiology assays (in vitro) are available on main campus for nominal fees. Note that hERG activity is merely a flag for potential drug induced long QT syndrome and not a "hard" CSF per say (CSF9a, FIG. 1).

To triage and evaluate compounds derived from Aim 2B for inhibition of DYRK1A-catalyzed tau phosphorylation (CSF6 & 7, Box 10 & 11, FIG. 1).

In Vitro Phosphorylation Assay (CSF6, Box 10):

Promising compounds from Aim 2a will be sent for $IC_{50}$ determination using a physiologically relevant substrate, full-length tau protein. Details of the in vitro phosphorylation assay have been published previously, where experiments have shown the assay to be highly reproducible, able to clearly discriminate affinities down to the low nM range (see, Frost D, et al., PLoS One 2011; 6:e19264). The assay involves the use of recombinant DYRK1A protein and recombinant tau protein in a standard in vitro phosphorylation assay to assess the direct phosphorylation of tau by DYRK1A (see, Frost D, et al., PLoS One 2011; 6:e19264).

Cellular Activity Assay (CSF7, Box 10):

Methodological details of the assay is previously described (see, Frost D, et al., PLoS One 2011; 6:e19264).

Harmine and EGCg improve cognitive performance in wild-type mice and Ts65Dn mice and their mode of action is postulated to be through DYRK1A inhibition (see, De la Torre R, et al., Mol Nutr Food Res 2014; 58:278-288). Hence, it was proposed that inhibition of DYRK1A will improve cognitive performance in the Ts65Dn mice which experiments will directly evaluate using a battery of behavioral tests.

DYRK1A kinase phosphorylates several cellular substrates in vivo (see, Smith B, et al., ACS ChemNeurosci 2012; 3:857-872), including the microtubule associated protein tau (see, Ryoo S R, et al., J Biol Chem 2007; 282: 34850-34857) and the amyloid precursor protein (see, Ryoo S R, et al., J Neurochem 2008; 104:1333-1344). The combined effect of these phosphorylation events are to increase forms of hyperphosphorylated tau protein that are associated with neurodegeneration and to increase the production of neurotoxic amyloid beta peptides. These DYRK1A regulated events are thought to contribute to the early onset Alzheimer's pathology in DS patients and are highly relevant molecular endpoints that will directly assess the extent to which inhibitors ameliorate these deleterious molecular phenotypes.

Example II

This example provides information for specific benzimidazole compounds of the present invention:

1-(4-methoxyphenyl)-6-(pyridin-4-yl)-1H-benzo[d]imidazole, 1

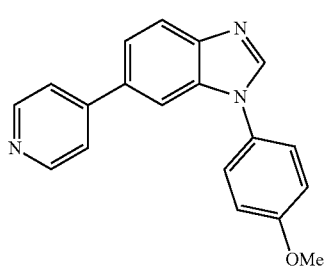

Chemical Formula: $C_{19}H_{15}N_3O$
Molecular Weight: 301.3419

Brown solid. Mp: 135-137° C. 1H NMR (400 MHz, CDCl$_3$) δ 8.65 (d, J=4.7 Hz, 2H), 8.12 (s, 1H), 7.97 (d, J=8.4 Hz, 1H), 7.68 (s, 1H), 7.62 (dd, J=8.4, 1.4 Hz, 1H), 7.54 (d, J=4.8 Hz, 2H), 7.46 (dd, J=6.8, 5.5 Hz, 2H), 7.17-7.08 (m, 2H), 3.91 (d, J=1.3 Hz, 3H). LC/MS [M+1]+=302.

1-(4-methoxyphenyl)-6-(pyrimidin-5-yl)-1H-benzo[d]imidazole, 2

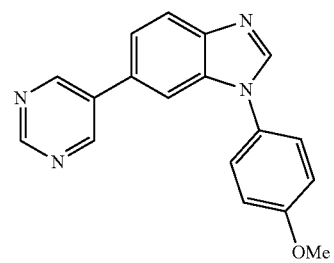

$^1$H NMR (400 MHz, CDCl$_3$) δ 9.19 (s, 1H), 8.97 (s, 2H), 8.14 (s, 1H), 8.01 (d, J=8.4 Hz, 1H), 7.59 (d, J=18.9 Hz, 1H), 7.53 (dt, J=15.9, 7.9 Hz, 1H), 7.49-7.40 (m, 2H), 7.16-7.04 (m, 2H), 3.91 (s, 3H). $^{13}$C NMR (100 MHz, CDCl$_3$) δ 159.75, 157.25, 155.12, 143.95, 134.85, 130.01, 128.57, 125.96, 121.92, 121.55, 115.38, 109.05, 55.71. LC/MS [M+1]+=303

6-(2-chloropyridin-3-yl)-1-(4-methoxyphenyl)-1H-benzo[d]imidazole, 3

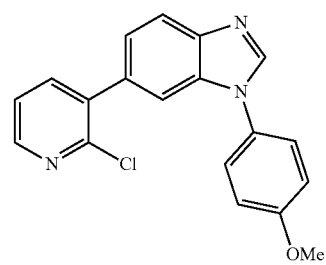

Yellow solid. Mp: 141-143° C. $^1$H NMR (400 MHz, CDCl$_3$) δ 8.46-8.35 (m, 1H), 8.13 (s, 1H), 7.98-7.89 (m, 1H), 7.77-7.68 (m, 1H), 7.54 (dd, J=1.6, 0.6 Hz, 1H), 7.47-7.41 (m, 2H), 7.41-7.38 (m, 1H), 7.33-7.25 (m, 1H), 7.11-7.05 (m, 2H), 3.89 (s, 3H). $^{13}$C NMR (100 MHz, CDCl$_3$) δ 159.52, 149.91, 148.27, 143.70, 143.56, 139.97, 137.29, 134.16, 133.00, 128.78, 125.77, 124.18, 122.46, 120.33, 115.26, 111.44, 55.66. LC/MS [M+1]+=336

5-(1-(4-methoxyphenyl)-1H-benzo[d]imidazol-6-yl)pyridin-2-amine, 4

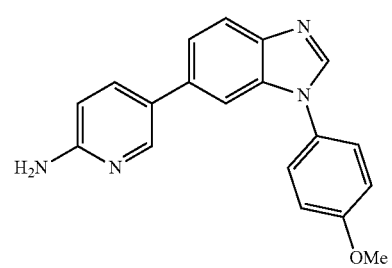

Yellow solid. Mp: 172-174° C. $^1$H NMR (400 MHz, CDCl$_3$) δ 8.32 (dd, J=2.4, 0.7 Hz, 1H), 8.06 (s, 1H), 7.90 (dd, J=8.4, 0.6 Hz, 1H), 7.69 (dd, J=8.5, 2.5 Hz, 1H), 7.52 (dd, J=1.7, 0.6 Hz, 1H), 7.49-7.40 (m, 3H), 7.15-7.04 (m, 2H), 6.58 (dd, J=8.5, 0.7 Hz, 1H), 4.54 (s, 2H), 3.90 (s, 3H). $^{13}$C NMR (100 MHz, CDCl$_3$) δ 159.46, 157.37, 146.43, 143.05, 143.01, 137.01, 134.95, 134.35, 129.01, 127.90, 125.86, 121.75, 120.78, 115.22, 108.53, 107.90, 55.68.

1-(4-methoxyphenyl)-6-phenyl-1H-benzo[d]imidazole, 5

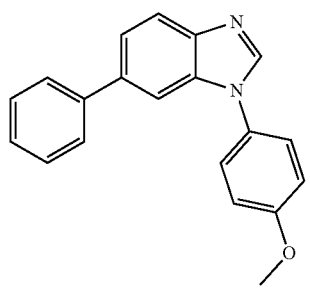

Solvent was degassed with N$_2$. The product of the previous reaction was dissolved in DMF:H$_2$O (4:1.10 mL). To the resulting solution, boronic acid (1 eq.), Na$_2$CO$_3$ (4 eq.) and Pd(dppf)Cl$_2$ (0.05 eq.) were added and the reaction was heated at 90° C. for 16 h. After cooling down to room temperature, the reaction was filtered through a celite pad, diluted with DCM:IPA (3:1, 100 mL), washed with H$_2$O (3×50 mL) and brine (1×100 mL), dried (MgSO$_4$) and concentrated under reduced pressure. The product was purified by silica gel column chromatography using an ISCO system (EtOAc/hexane, 0 to 80%) to afford 5 1-506, 113 mg, 38%; white solid; LC MS [M+1]$^+$ m/z 302.00; $^1$H NMR (400 MHz, DMSO$_{d6}$) δ: 8.49 (s, 1H, N=C$\underline{\text{H}}$—N), 7.48 (d, 1H, J=8.1, ArH), 7.71-7.76 (m, 4H, ArH), 7.58 (dd, 1H, J=8.7, 1.5, ArH), 7.48-7.40 (m, 2H, ArH), 7.37-7.30 (m, 1H, ArH), 7.21-7.12 (m, 2H, ArH), 3.85 (s, 3H, OCH$_3$); $^{13}$C NMR (100 MHz, DMSO$_{d6}$) δ: 158.7, 144.1, 143.1, 140.7, 136.0, 134.2, 128.9, 128.7, 127.1, 125.7, 121.7, 120.1, 115.2, 108.5, 55.5.

Synthetic Scheme to 5 & 7

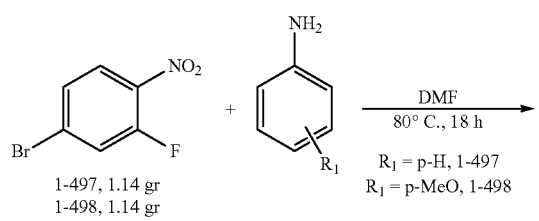

1-497, 1.14 gr
1-498, 1.14 gr

R$_1$ = p-H, 1-497
R$_1$ = p-MeO, 1-498

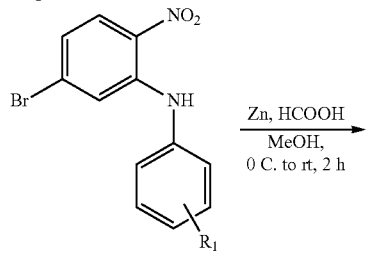

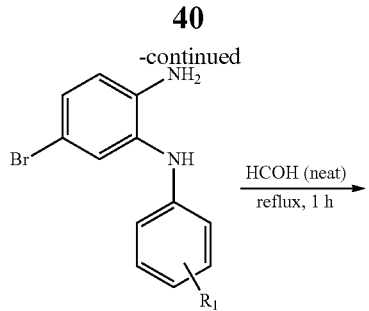

R$_1$ = p-H, 1-501
R$_1$ = p-MeO, 1-500

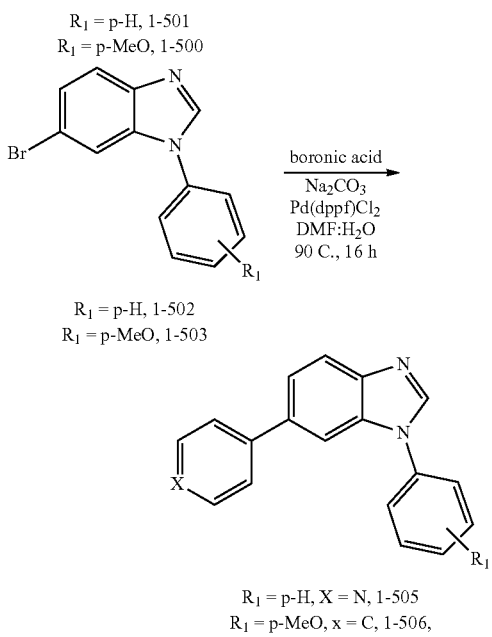

R$_1$ = p-H, 1-502
R$_1$ = p-MeO, 1-503

R$_1$ = p-H, X = N, 1-505
R$_1$ = p-MeO, x = C, 1-506,

Intermediates (5-bromo-2-nitro-N-phenylaniline) and 5-bromo-N-(4-methoxyphenyl)-2-nitroaniline A mixture of 4-bromo-2-fluoro-1-nitrobenzene (1.14 g, 1 eq) and aniline (1 eq) in DMF (30 mL) was heated at 80° C. and the reaction progression checked by LC MS. After 18 h the reaction was cooled down to room temperature, diluted with water (50 mL) and extracted with DCM (3×50 mL). The organic layers were collected, washed with H$_2$O (2×50 mL), brine (1×50 mL) and dried (MgSO$_4$). The solvent was removed under reduced pressure and the crude product was used in the next reaction without further purification. 1-497, LC MS [M+1]$^+$ m/z 293.00; 1-498, LC MS [M+1]$^+$ m/z 323.00.

Intermediates 1-500 (5-bromo-N1-(4-methoxyphenyl)benzene-1,2-diamine) and 501 (5-bromo-N1-phenylbenzene-1,2-diamine)

The crude product from the previous reaction was dissolved in MeOH (10 mL) and the resulting solution was cooled to 0° C. Zn (7 eq) and formic acid (7 eq) were slowly added keeping the reaction temperature at 0° C. After stirring for 2 h at room temperature, the solid was filtered off and the crude amine was obtained as a solid after removing the solvent under reduced pressure. The product was used in the following reaction without further purification. LC MS [M+1]$^+$ m/z 346.00; LC MS [M+1]$^+$ m/z 293.00.

Intermediates (6-bromo-1-phenyl-1H-benzo[d]imidazole) and (6-bromo-1-(4-methoxyphenyl)-1H-benzo[d]imidazole)

The crude product from the previous reaction was dissolved in neat formaldehyde (10 mL) and the resulting solution refluxed at 90° C. for 1 h. After cooling down to room temperature, the solvent was removed under reduced pressure and the product purified by silica gel column chromatography. Final yields: 508 mg, 36%, over 3 steps; 1.2 g, 84%, over 3 steps. LC MS [M+1]$^+$ m/z 273.00; LC MS [M+1]$^+$ m/z 303.00.

Synthesis of 6

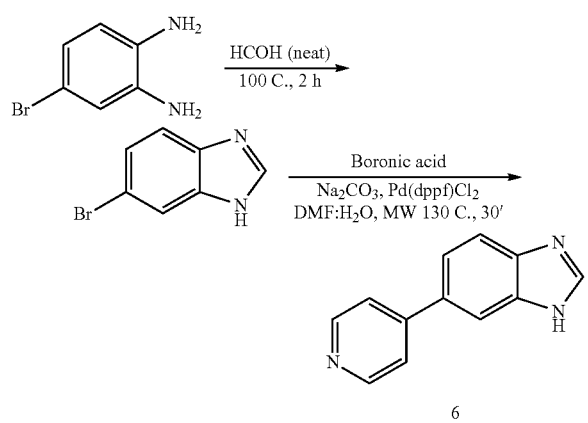

6

Intermediate 6-bromo-1H-benzo[d]imidazole

A stirring solution of starting material (1 gr, 1 eq) was dissolved in neat HCOH (10 mL) and heated for 2 h at 100° C. The reaction was cooled down to room temperature, the solvent removed under reduced pressure and the product purified by silica gel column chromatography using an ISCO system (EtOAc-hexane, 0-100%) (831 mg, 79%). LC MS [M+1]$^+$ m/z 196.00.

6-(pyridin-4-yl)-1H-benzo[d]imidazole, 6

Solvent was degassed with N$_2$. The product of the previous reaction (400 mg, 1 eq) was dissolved in DMF:H$_2$O (4:1, 5 mL). To the resulting solution, boronic acid (249 mg, 1 eq), Na$_2$CO$_3$ (848 mg, 4 eq) and Pd(dppf)Cl$_2$ (81 mg, 0.05 eq) were added and the reaction was heated at 130° C. for 30' under microwave irradiation. After cooling down to room temperature, the reaction was filtered through a celite pad, diluted with DCM:IPA (3:1, 10 mL), washed with NaHCO$_3$ (1×30 mL), H$_2$O (3×50 mL) and brine (1×100 mL), dried (MgSO$_4$) and concentrated under reduced pressure. The product was purified by silica gel column chromatography using an ISCO system (EtOAc/hexane, 0 to 80%). Final yields: 171 mg, 44%; white solid; LC MS [M+1]$^+$ m/z 198.00; $^1$H NMR (400 MHz, CDCl$_3$) δ: 10.16 (brs, 1H, NH), 8.27 (s, 1H, N=CH—N), 7.58 (m, 2H, ArH), 7.34-7.30 (m, 3H, ArH), 7.20-7.18 (m, 1H, ArH), 7.10-7.04 (m, 1H, ArH); $^{13}$C NMR (100 MHz, CDCl$_3$) δ: 163.4, 160.5, 139.2, 139.1, 130.3, 129.8, 124.6, 124.5, 120.0, 118.4.

1-phenyl-6-(pyridin-4-yl)-1H-benzo[d]imidazole, 7

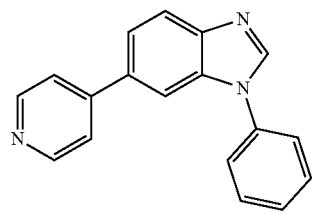

7

Solvent was degassed with N$_2$. The product of the previous reaction was dissolved in DMF:H$_2$O (4:1.10 mL). To the resulting solution, boronic acid (1 eq), Na$_2$CO$_3$ (4 eq) and Pd(dppf)Cl$_2$ (0.05 eq) were added and the reaction was heated at 90° C. for 16 h. After cooling down to room temperature, the reaction was filtered through a celite pad, diluted with DCM:IPA (3:1, 100 mL), washed with H$_2$O (3×50 mL) and brine (1×100 mL), dried (MgSO$_4$) and concentrated under reduced pressure. The product was purified by silica gel column chromatography using an ISCO system (EtOAc/hexane, 0 to 80%) to yield 10 (429 mg, 76% yield); brownish solid; $^1$H NMR (400 MHz, CDCl$_3$) δ: 8.70 (brs, 2H, ArH), 8.35 (brs, 1H, ArH), 7.57-7.54 (m, 2H, ArH), 7.37-7.30 (m, 4H, ArH), 7.20-7.09 (m, 4H, ArH). LC MS [M+1]$^+$ m/z 272.00

Synthesis route to 1-(4-methoxyphenyl)-1H-benzo[d]imidazole, 8

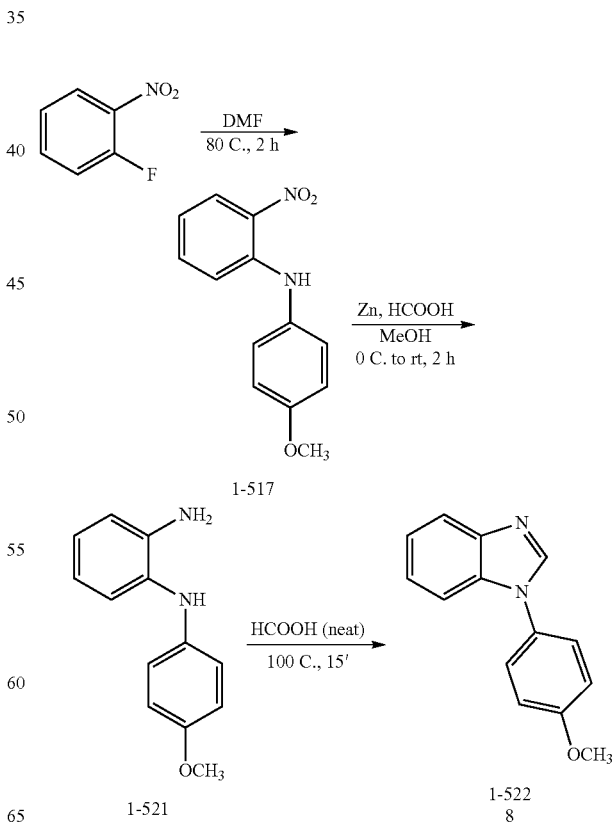

8

Intermediate N-(4-methoxyphenyl)-2-nitroaniline

Nitrofluorobenzene (1.5 g, 1 eq.) and p-anisidine (1.30 gr, 1 eq.) were mixed in DMF (20 mL) and heated at 80° C. for 2 h. The reaction mixture was diluted with EtOAc (10 mL) and washed with sat. NaHCO$_3$ (2×20 mL), H$_2$O (2×20 mL) and brine (20 mL). The organic layers were collected, dried (MgSO$_4$) and concentrated under reduced pressure. The crude product was used in the following reaction without further purification (2 gr); LC MS [M+1]$^+$ m/z 245.00.

Intermediate N1-(4-methoxyphenyl)benzene-1,2-diamine

Crude starting material (2 g) was dissolved in MeOH (10 mL). After cooling the resulting solution down to 0° C., Zn (7 eq.) and HCOOH (7 eq.) were slowly added. The reaction was stirred at room temperature for 2 h. The solid was filtered-off and the resulting solution concentrated under reduced pressure. The product was used in the next reaction without further purification (1 g); LC MS [M+1]$^+$ m/z 215.00.

1-(4-methoxyphenyl)-1H-benzo[d]imidazole. 8

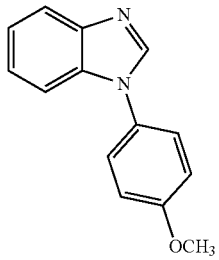

8

Crude starting material (1 gr) was dissolved in neat HCOH (10 mL) and the resulting solution heated at 100° C. for 15' under microwave irradiation. The reaction was concentrated under reduced pressure and the residue was purified by silica-gel column chromatography using an ISCO system (EtOAc-hexane 0-100%). The product was obtained as a brown solid (500 mg, 47% yield). LC/MS [M+1]$^+$ m/z 225.00; $^1$H NMR (400 MHz, CDCl$_3$) δ: 8.07 (s, 1H, N═C<u>H</u>—N), 7.90-7.84 (m, 1H, ArH), 7.47-7.42 (m, 1H, ArH), 7.40 (dd, 2H, J=9.0, AA'BB' system, ArH), 7.34-7.29 (m, 2H, ArH), 7.06 (dd, 2H, J=9.0, 2.4, ArH), 3.88 (s, 3H, OCH$_3$); $^{13}$C NMR (100 MHz, DMSO$_{d6}$) δ: 158.7, 143.6, 143.4, 133.6, 128.8, 125.4, 123.2, 122.2, 120.6, 115.1, 113.9, 55.5.

1-(4-methoxyphenyl)-6-(pyridin-4-yl-N-oxide)-1H-benzo[d]imidazole, 9

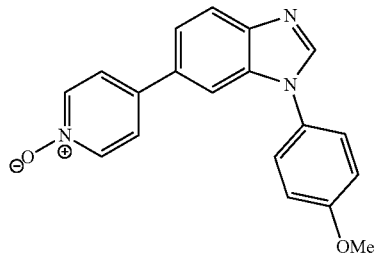

9

$^1$H NMR (400 MHz, DMSO-d6) δ 11.27 (s, 1H), 8.17 (dd, J=26.0, 6.9 Hz, 2H), 7.65 (d, J=7.1 Hz, 2H), 7.45 (dd, J=7.3, 4.9 Hz, 3H), 7.12 (dd, J=19.7, 8.7 Hz, 4H), 3.82 (s, 3H). $^{13}$C NMR (100 MHz, DMSO-d6) δ 158.89, 154.11, 139.13, 137.10, 131.93, 129.54, 129.28, 128.22, 127.20, 123.82, 120.63, 115.13, 110.00, 106.02, 55.85. LC/MS [M+1]$^+$=318.

1-(benzo[d][1,3]dioxol-5-yl)-6-(pyridin-4-yl)-1H-benzo[d]imidazole, 10

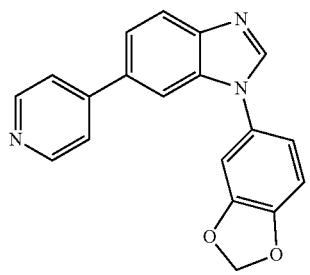

10

$^1$H NMR (400 MHz, CDCl$_3$) δ 8.65 (d, J=6.0 Hz, 2H), 8.10 (s, 1H), 7.96 (d, J=8.4 Hz, 1H), 7.70 (dd, J=8.3, 7.1 Hz, 1H), 7.62 (dd, J=8.4, 1.7 Hz, 1H), 7.54 (dd, J=4.5, 1.6 Hz, 2H), 7.04-6.95 (m, 3H), 6.12 (s, 2H). $^{13}$C NMR (100 MHz, CDCl$_3$) δ 165.96, 150.56, 147.87, 145.17, 145.07, 140.09, 133.68, 133.67, 131.57, 128.91, 124.03, 122.55, 122.16, 121.15, 109.94, 52.85.

1-(2,3-dihydrobenzofuran-5-yl)-6-(pyridin-4-yl)-1H-benzo[d]imidazole, 11

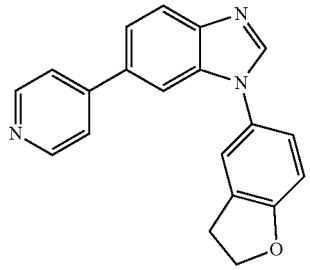

11

A suspension of 6-bromo-1-(2,3-dihydrobenzofuran-5-yl)-1H-benzo[d]imidazole (63 mg, 0.2 mmol), 4-pyridine boronic acid (37 mg, 0.3 mmol), Pd(Ph3)4 (10 mg, 0.04 mmol) and Na$_2$CO$_3$ (42 mg, 0.4 mmol) in dioxane/H$_2$O (5 ml, 4:1) under argon was irradiated with microwaves at 130° C. for 10 minutes. The solvent was evaporated in vacuo and product purified by column chromatography (0-100%, hexane/ethyl acetate) to afford 14 as white solid (35 mg, 56% yield). 1H NMR (400 MHz, CDCl3) δ 8.67-8.63 (m, 2H), 8.12 (s, 1H), 7.99-7.93 (m, 1H), 7.69-7.52 (m, 4H), 7.34-7.23 (m, 2H), 6.98-6.95 (m, 1H), 4.75-4.68 (m, 2H), 3.39-3.31 (m, 2H); 13C NMR (100 MHz, CDCl3) δ 160.4, 150.2, 148.8, 144.5, 144.1, 133.9, 129.2, 128.5, 125.0, 121.8, 121.0, 110.3, 109.0, 71.9, 29.7.

1-(4-(1H-tetrazol-5-yl)phenyl)-6-(pyridin-4-yl)-1H-benzo[d]imidazole, 12

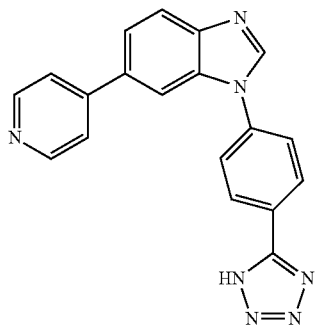

12

A suspension of 4-(6-(pyridin-4-yl)-1H-benzo[d]imidazol-1-yl)benzonitrile (30 mg, 0.10 mmol), NaN$_3$ (7 mg, 0.13 mmol), NH$_4$Cl (7 mg, 0.13 mmol) and LiCl (2 mg, 0.01 mmol) in DMF (8 ml) was heated to 100° C. under argon. The solvent was evaporated in vacuo and the residue was diluted with EtOAc and washed with brine. The organic layer was dried (MgSO$_4$), evaporated in vacuo and product purified by column chromatography (0-40%, hexane/ethylacetate) to afford a white solid 15 (23 mg, 67% yield). 1H NMR (400 MHz, DMSO-d6) δ 8.59-8.58 (m, 2H), 8.36-8.30 (m, 3H), 7.97-7.95 (m, 2H), 7.86-7.85 (m, 1H), 7.69-7.63 (m, 4H), 7.38 (s, 1H); 13C (100 MHz, DMSO-d6) δ 149.6, 144.2, 143.8, 135.7, 134.4, 134.3, 132.2, 132.1, 130.8, 129.0, 128.8, 128.6, 124.7, 120.9, 109.7.

6-(pyridin-4-yl)-3'H-1,5'-dibenzo[d]imidazole, 13

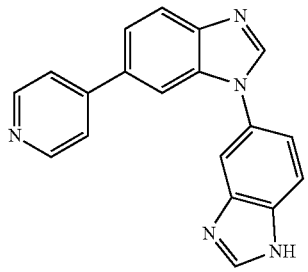

13

1H NMR (400 MHz, CDCl$_3$) δ 8.56 (d, J=4.8 Hz, 2H), 8.29 (s, 1H), 8.23 (s, 1H), 7.96 (d, J=8.5 Hz, 1H), 7.89 (dd, J=18.4, 6.2 Hz, 2H), 7.79 (d, J=0.9 Hz, 1H), 7.72-7.65 (m, 1H), 7.65-7.56 (m, 2H), 7.51-7.44 (m, 1H). $^{13}$C NMR (100 MHz, CDCl$_3$) δ 149.35, 149.16, 144.10, 143.59, 143.11, 134.86, 133.79, 130.33, 122.25, 122.18, 120.38, 119.61, 109.25.

6-(3-methoxyphenyl)-1-(4-(methylsulfonyl)phenyl)-1H-benzo[d]imidazole, 14

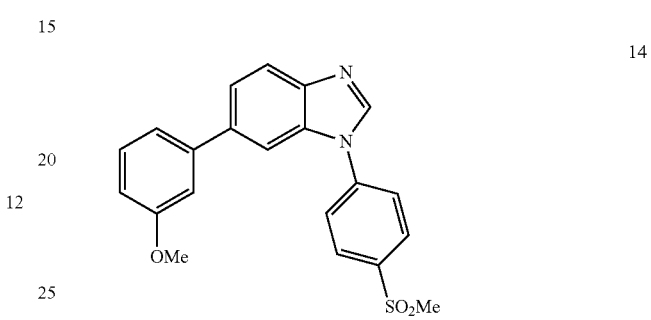

14

Brown solid. Mp: 118-120° C. $^1$H NMR (400 MHz, CDCl$_3$) δ 8.20 (d, J=8.3 Hz, 3H), 8.06-7.56 (m, 5H), 7.38 (t, J=7.9 Hz, 1H), 7.24-7.11 (m, 2H), 6.92 (ddd, J=8.3, 2.5, 0.8 Hz, 1H), 3.87 (s, 3H), 3.15 (d, J=3.5 Hz, 3H). $^{13}$C NMR (100 MHz, CDCl$_3$) δ 159.99, 142.71, 139.85, 138.23, 129.91, 129.84, 124.28, 123.48, 121.13, 120.04, 113.68, 112.40, 108.79, 55.40, 44.60. LC/MS [M+1]+=379

6-(3,4-difluorophenyl)-1-(4-(methylsulfonyl)phenyl)-1H-benzo[d]imidazole, 15

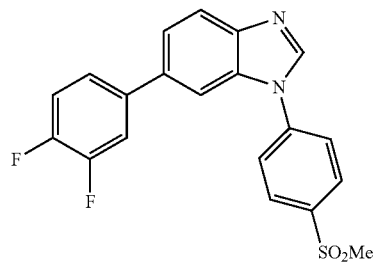

15

Brown solid. Mp: 211-213° C. $^1$H NMR (400 MHz, CDCl$_3$) δ 8.22 (d, J=8.1 Hz, 3H), 7.95 (d, J=7.4 Hz, 1H), 7.80 (d, J=8.3 Hz, 2H), 7.68 (s, 1H), 7.55 (d, J=6.0 Hz, 1H), 7.40 (ddd, J=11.2, 7.5, 2.0 Hz, 1H), 7.36-7.29 (m, 1H), 7.26-7.19 (m, 1H), 3.16 (s, 3H). $^{13}$C NMR (100 MHz, CDCl$_3$) δ 151.77, 151.26, 151.13, 149.30, 148.78, 148.65, 140.02, 138.30, 136.20, 129.88, 124.33, 123.45, 123.41, 123.39, 123.35, 123.13, 121.41, 117.72, 117.56, 116.47, 116.30, 108.65, 44.56. LC/MS [M+1]+=385

1-(4-(methylsulfonyl)phenyl)-6-(pyridin-4-yl)-1H-benzo[d]imidazole, 16

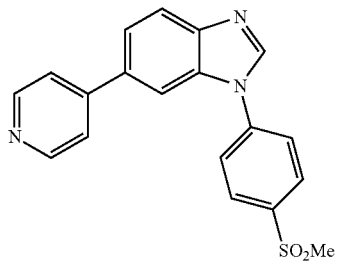

White solid. Mp: 209-211° C. ¹H NMR (400 MHz, CDCl₃) δ 8.67 (dd, J=4.6, 1.6 Hz, 2H), 8.34-8.17 (m, 3H), 8.01 (d, J=8.4 Hz, 1H), 7.85-7.74 (m, 3H), 7.68 (dd, J=8.5, 1.6 Hz, 1H), 7.54 (dd, J=4.5, 1.7 Hz, 2H), 3.17 (s, 3H). ¹³C NMR (100 MHz, CDCl₃) δ 150.31, 148.40, 144.93, 142.89, 140.64, 140.18, 135.06, 133.71, 129.94, 124.40, 123.00, 121.98, 121.72, 108.85, 44.57. LC/MS [M+1]+=350.

1-(4-(methylsulfonyl)phenyl)-6-(pyridin-3-yl)-1H-benzo[d]imidazole, 17

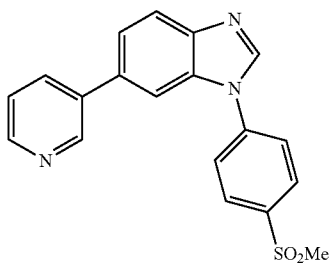

Orange solid. Mp: 203-205° C. ¹H NMR (400 MHz, CDCl₃) δ 8.88 (d, J=2.3 Hz, 1H), 8.61 (dd, J=4.8, 1.5 Hz, 1H), 8.33-8.14 (m, 3H), 8.00 (d, J=8.4 Hz, 1H), 7.95-7.88 (m, 1H), 7.84-7.78 (m, 2H), 7.77-7.73 (m, 1H), 7.61 (dd, J=8.4, 1.7 Hz, 1H), 7.39 (dd, J=7.9, 4.8 Hz, 1H), 3.16 (s, 3H). ¹³C NMR (100 MHz, CDCl₃) δ 148.57, 148.55, 144.25, 142.54, 140.71, 140.03, 136.73, 134.75, 134.73, 133.68, 129.89, 124.32, 123.61, 123.26, 121.64, 108.90, 44.58. LC/MS [M+1]+=350

1-(4-(methylsulfonyl)phenyl)-6-(4-(trifluoromethoxy)phenyl)-1H-benzo[d]imidazole, 18

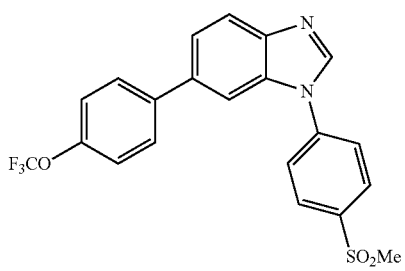

Brown solid. Mp: 219-221° C. ¹H NMR (400 MHz, CDCl₃) δ 8.22 (t, J=7.1 Hz, 3H), 7.96 (d, J=8.2 Hz, 1H), 7.80 (d, J=8.5 Hz, 2H), 7.72 (s, 1H), 7.66-7.55 (m, 3H), 7.30 (d, J=8.1 Hz, 2H), 3.16 (s, 3H). ¹³C NMR (100 MHz, CDCl₃) δ 148.76, 139.99, 136.97, 129.88, 128.87, 124.32, 123.35, 121.38, 108.83, 44.58. LC/MS [M+1]+=433

6-(benzo[d][1,3]dioxol-5-yl)-1-(4-(methylsulfonyl)phenyl)-1H-benzo[d]imidazole, 19

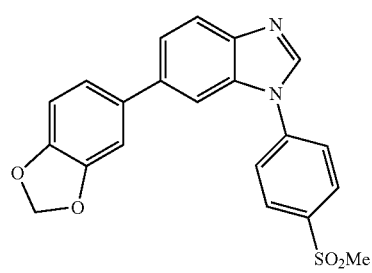

Gray solid. Mp: 182-184° C. ¹H NMR (400 MHz, CDCl₃) δ 8.19 (t, J=6.7 Hz, 3H), 7.91 (d, J=8.3 Hz, 1H), 7.78 (t, J=8.1 Hz, 2H), 7.66 (s, 1H), 7.54 (t, J=7.5 Hz, 1H), 7.12-7.00 (m, 2H), 6.89 (dd, J=7.6, 0.8 Hz, 1H), 6.01 (d, J=1.3 Hz, 2H), 3.15 (d, J=2.7 Hz, 3H). ¹³C NMR (100 MHz, CDCl₃) δ 148.21, 147.22, 142.02, 140.93, 139.80, 138.15, 135.52, 129.83, 124.24, 123.28, 121.11, 121.03, 108.66, 108.39, 108.01, 101.26, 44.60. LC/MS [M+1]+=393

4-(5-(1-(4-(methylsulfonyl)phenyl)-1H-benzo[d]imidazol-6-yl)pyridin-2-yl)morpholine, 20

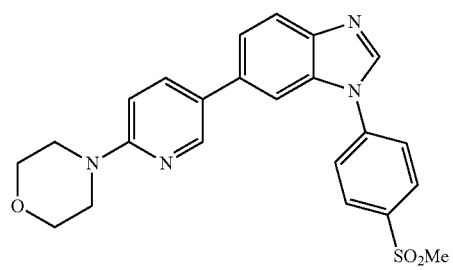

Brown solid. 235-237° C. ¹H NMR (400 MHz, CDCl₃) δ 8.48 (d, J=2.2 Hz, 1H), 8.20 (d, J=8.4 Hz, 3H), 8.03-7.47 (m, 5H), 6.73 (d, J=8.7 Hz, 2H), 3.98-3.78 (m, 4H), 3.55 (dd, J=19.4, 14.6 Hz, 4H), 3.16 (s, 3H). ¹³C NMR (100 MHz, CDCl₃) δ 139.83, 129.81, 126.75, 124.19, 122.61, 121.39, 109.98, 107.72, 106.77, 66.70, 45.64, 44.59. LC/MS [M+1]+=435.

6-(3-chloro-4-methoxyphenyl)-1-(4-(methylsulfonyl)phenyl)-1H-benzo[d]imidazole, 21

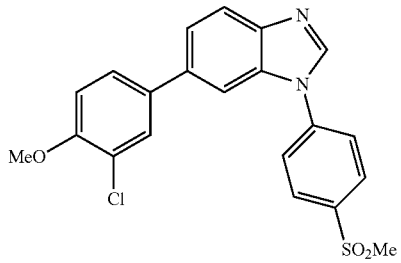

Gray solid. Mp: 199-201° C. $^1$H NMR (400 MHz, CDCl$_3$) δ 8.22 (d, J=7.9 Hz, 3H), 7.93 (s, 1H), 7.80 (d, J=8.2 Hz, 2H), 7.74-7.52 (m, 3H), 7.47 (dd, J=8.5, 2.2 Hz, 1H), 7.02 (d, J=8.5 Hz, 1H), 3.95 (s, 3H), 3.16 (s, 3H). $^{13}$C NMR (100 MHz, CDCl$_3$) δ 154.54, 139.93, 136.75, 134.62, 129.89, 129.16, 126.71, 124.35, 122.90, 121.28, 112.37, 56.31, 44.61. LC/MS [M+2]+=414

6-(furan-3-yl)-1-(4-(methylsulfonyl)phenyl)-1H-benzo[d]imidazole, 22

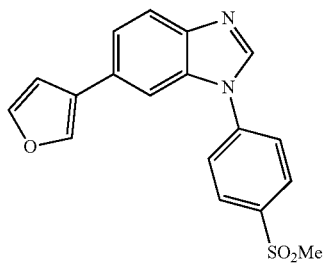

White solid. Mp: 194-196° C. $^1$H NMR (400 MHz, CDCl$_3$) δ 8.21 (dd, J=31.2, 22.8 Hz, 3H), 7.89 (d, J=8.4 Hz, 1H), 7.84-7.72 (m, 3H), 7.63 (d, J=0.6 Hz, 1H), 7.57-7.48 (m, 2H), 6.81-6.66 (m, 1H), 3.17 (s, 3H). $^{13}$C NMR (100 MHz, CDCl$_3$) δ 143.89, 143.47, 141.91, 140.91, 139.87, 138.62, 129.84, 129.42, 126.54, 124.27, 122.30, 121.33, 109.09, 107.21, 44.59. LC/MS [M+1]+=339.

4-(6-(pyridin-4-yl)-1H-benzo[d]imidazol-1-yl)benzonitrile, 23

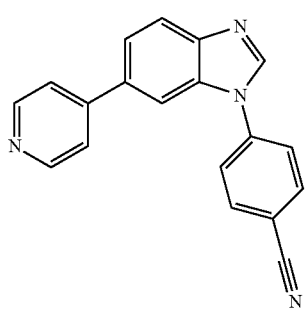

To a suspension of 4-(6-bromo-1H-benzo[d]imidazol-1-yl)benzonitrile (297 mg, 1.0 mmol), 4-pyridine boronic acid (148 mg, 1.2 mmol) and Na$_2$CO$_3$ (220 mg, 2 mmol) in a 1,4-dioxane and H$_2$O solution (4:1, 10 ml) under argon, was added Pd(PPh$_3$)$_4$(20 mg). The reaction was irradiated with microwave at 130° C. for 20 min. The solvent was removed in vacuo and the product was purified by column chromatography to yield 26 as a white solid (169 mg, 57%). LC/MS [M+1]$^+$ m/z 297; $^1$H NMR (400 MHz, DMSO$_{d6}$) δ: 8.64 (s, 1H), 8.23 (s, 1H), 7.97-8.12 (m, 4H), 7.85 (s, 1H), 7.75-7.78 (m, 2H), 7.73 (s, 1H), 7.59-7.61 (m, 1H), 7.04 (s, 1H). $^{13}$C NMR (100 MHz, DMSO$_{d6}$) δ: 144.63, 144.00, 143.62, 140.18, 139.88, 134.79, 133.45, 128.68, 126.61, 124.62, 121.86, 120.85, 118.79, 110.32, 109.62, 108.02.

4-(6-(furan-3-yl)-1H-benzo[d]imidazol-1-yl)benzonitrile, 24

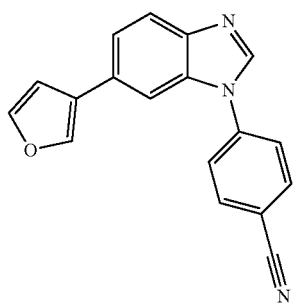

To a suspension of 4-(6-bromo-1H-benzo[d]imidazol-1-yl)benzonitrile (297 mg, 1.0 mmol), boronic acid (133 mg, 1.2 mmol), Na$_2$CO$_3$ (212 mg, 2.0 mmol) in 1,4-dioxane/H$_2$O (10 ml/2 ml) under argon was added Pd(PPh$_3$)$_4$(30 mg). The reaction was irradiated with microwaves at 130° C. for 30 mins. The reaction mixture was filtered, evaporated in vacuo and the 27 was purified by column chromatography (0-100%, ethyl acetate/hexane) to afford 27 (188 mg, 66% yield) as a white solid. LC MS [M+1]$^+$ m/z 286; $^1$H NMR (400 MHz, DMSO$_{d6}$) δ: 8.44 (s, 1H), 8.20-8.24 (m, 2H), 7.67-7.76 (m, 4H), 7.41-7.42 (m, 1H), 7.29-7.33 (m, 2H), 6.14 (s, 1H). $^{13}$C NMR (100 MHz, DMSO$_{d6}$) δ: 150.57, 147.86, 145.17, 145.13, 140.01, 134.81, 133.78, 133.54, 124.75, 122.69, 122.19, 121.17, 110.53, 110.05.

4-(6-(1H-pyrazol-4-yl)-1H-benzo[d]imidazol-1-yl)benzonitrile, 25

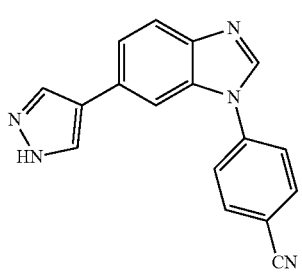

Synthetic Route to 25 and 37

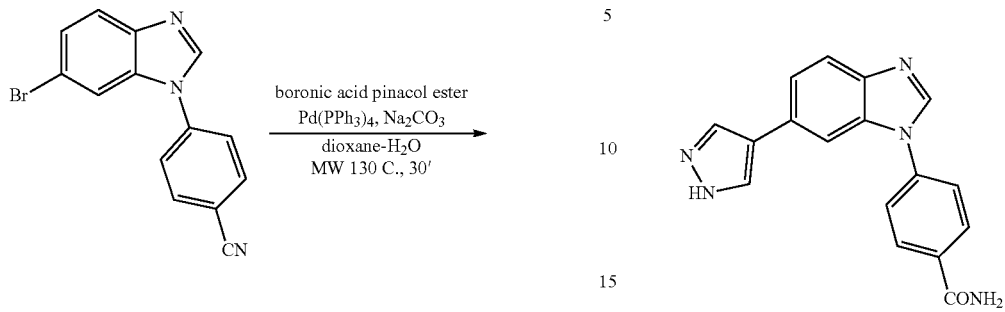

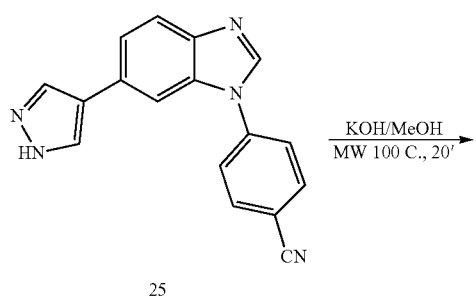

4-(6-(1H-pyrazol-4-yl)-1H-benzo[d]imidazol-1-yl)benzamide, 37

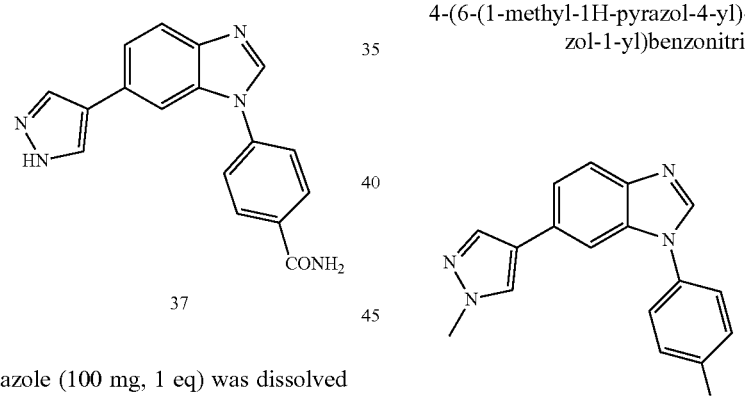

To a suspension of 25 (41 mg, 1 eq) in MeOH (3 mL), KOH (40 mg, 5 eq) was added and the reaction was heated at 100° C. for 20' under microwave irradiation. The solvent was removed under reduced pressure and the residue was columned on silica gel using an ISCO system (EtOAc-hexane, 0-100%). Final yields: 14 mg, 33%. white solid; LC MS [M+1]+ m/z 304.00. $^1$H NMR (400 MHz, DMSO$_{d6}$) δ: 12.90 (br s, 2H, NH$_2$), 8.56 (s, 1H, N=C$\underline{H}$—N), 8.30-7.91 (m, 5H, ArH), 7.87-7.79 (m, 2H, ArH), 7.75 (dd, 1H, J=8.4, 3.5, ArH), 7.59 (dd, 1H, J=8.4, 1.4, ArH), 7.50 (br s, 1H, NH); $^{13}$C NMR (100 MHz, DMSO$_{d6}$) δ: 166.9, 143.2, 142.4, 138.3, 133.4, 133.0, 129.4, 129.1, 123.1, 121.6, 121.0, 120.2, 109.5, 109.6, 106.8.

4-(6-(1-methyl-1H-pyrazol-4-yl)-1H-benzo[d]imidazol-1-yl)benzonitrile, 26

The bromo-benzimidazole (100 mg, 1 eq) was dissolved in dioxane:H$_2$O (4:1, 5 mL). To the resulting solution, boronic acid pinacol ester (97 mg, 1.5 eq), Na$_2$CO$_3$ (70 mg, 4 eq) and Pd(PPh$_3$)$_4$ (38 mg, 0.1 eq) were added and the reaction was heated at 130° C. for 30' under microwave irradiation. After cooling down to room temperature, the reaction was filtered through a celite pad, diluted with DCM:IPA (3:1, 10 mL), washed with NaHCO$_3$ (1×30 mL), H$_2$O (3×50 mL) and brine (1×100 mL), dried (MgSO$_4$) and concentrated under reduced pressure. The product was purified by silica gel column chromatography using an ISCO system (EtOAc/hexane, 0 to 80%). Yield: 80 mg, 85%; white solid; LC MS [M+1]+ m/z 286.00; $^1$H NMR (400 MHz, DMSO$_{d6}$) δ: 12.92 (brs, 1H, NH), 8.62 (s, 1H, N=C$\underline{H}$—N), 8.39-7.82 (m, 7H, ArH), 7.76 (d, 1H, J=8.5, ArH), 7.61 (dd, 1H, J=8.5, 1.6, ArH); $^{13}$C NMR (100 MHz, DMSO$_{d6}$) δ: 143.1, 142.5, 139.8, 136.5, 134.3, 133.1, 129.3, 125.6, 124.1, 121.5, 121.2, 120.3, 118.4, 109.7, 106.8.

Synthetic Route to 26 and 38

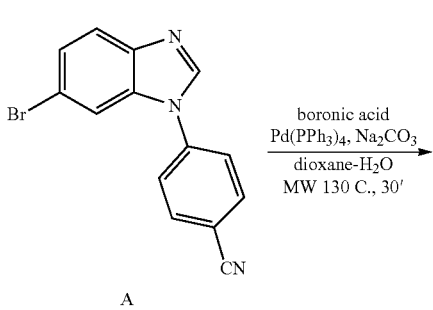

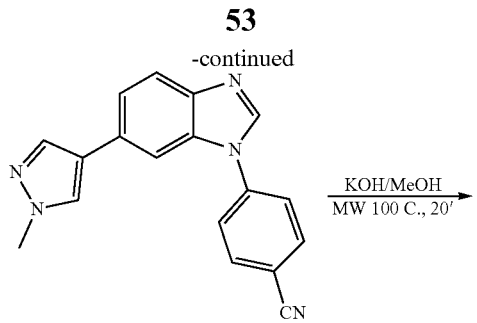

26

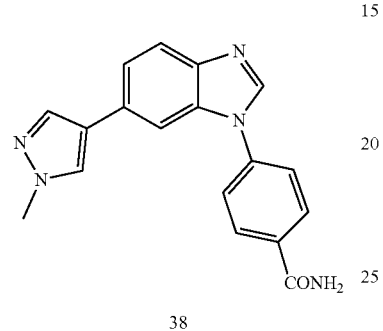

38

Solvent was degassed with $N_2$. The bromo-benzimidazole A (100 mg, 1 eq) was dissolved in dioxane:$H_2O$ (4:1, 3 mL). To the resulting solution, boronic acid (106 mg, 1.5 eq.), $Na_2CO_3$ (70 mg, 2 eq.) and $Pd(PPh_3)_4$ (38 mg, 0.01 eq) were added and the reaction was heated at 130° C. for 30' under microwave irradiation. After cooling down to room temperature, the reaction was filtered through a celite pad, diluted with DCM:IPA (3:1, 10 mL), washed with $NaHCO_3$ (1×30 mL), $H_2O$ (3×50 mL) and brine (1×100 mL), dried ($MgSO_4$) and concentrated under reduced pressure. The product was purified by silica gel column chromatography using an ISCO system (EtOAc/hexane, 0 to 80%). Yield: 75 mg, 76%; white solid; LC MS [M+1]$^+$ m/z 300.00; $^1$H NMR [400 MHz, $(CD_3)_2CO$] δ: 8.44 (s, 1H, N=C$\underline{H}$—N), 8.09-8.00 (m, 4H, ArH), 7.86 (m, 2H, ArH), 7.75 (d, 2H, J=8.8, ArH), 7.57 (d, 1H, J=8.5, ArH), 3.91 (s, 3H, $CH_3$); $^{13}$C NMR [100 MHz, $(CD_3)_2CO$] δ: 143.5, 141.3, 137.2, 135.1, 130.6, 128.4, 125.2, 124.0, 122.1, 121.7, 118.9, 111.8, 111.0, 107.8, 38.0.

4-(6-(1-methyl-1H-pyrazol-4-yl)-1H-benzo[d]imidazol-1-yl)benzamide, 38

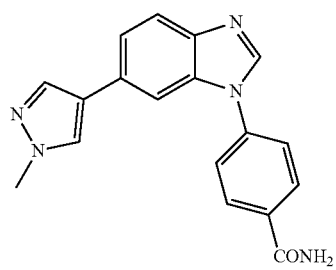

38

To a suspension of 26 (30 mg, 1 eq) in MeOH (3 mL), KOH (28 mg, 5 eq) was added and the reaction was heated at 100° C. for 20' under microwave irradiation. The solvent was removed under reduced pressure and the residue was columned on silica gel using an ISCO system (EtOAc-hexane, 0-100%). Yield: 10 mg, 32%; white solid; LC MS [M+1]$^+$ m/z 318.00; $^1$H NMR (400 MHz, $CDCl_3$) δ: 8.12 (s, 1H, N=C$\underline{H}$—N), 8.07 (d, 2H, J=8.7, 2.0, A'ABB' system, ArH), 7.86 (d, 1H, J=8.4, ArH), 7.76 (s, 1H, ArH), 7.64-7.60 (m, 3H, ArH), 7.49 (dd, 1H, J=8.1, 1.4, ArH), 3.96 (s, 3H, $CH_3$).

4-(6-(pyridin-4-yl)-1H-benzo[d]imidazol-1-yl)benzoic acid, 27

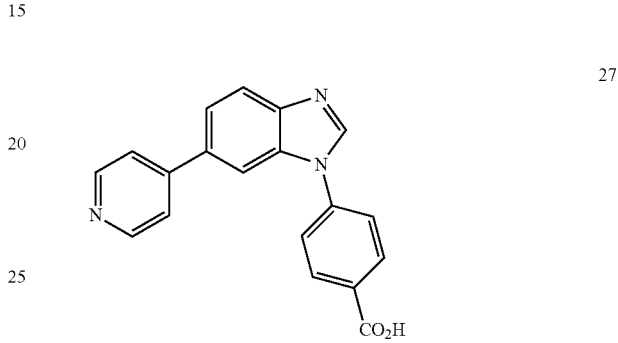

27

0.13 g (0.395 mmol) of the methyl ester 32 were mixed with 5% NaOH (1.58 mL) and microwaved for 5 minutes at 90 C with stirring. The solution was titrated to pH 4.0 using 1N HCl until product precipitated. The white solid was filtered using a Buchner funnel and filter paper, then dried under vacuum overnight at 30° C. to yield 27 (95% yield). LC/MS [M+1]$^+$ m/z 316; $^1$H NMR [400 MHz, DMSO-d6] δ: 8.68 (s, 1H), 8.60-8.63 (m, 2H), 8.11-8.15 (m, 2H), 7.98 (s, 1H), 7.90-7.92 (m, 1H), 7.77-7.80 (m, 2H), 7.73-7.76 (m, 1H), 7.68-7.72 (m, 2H).

4-(6-(furan-3-yl)-1H-benzo[d]imidazol-1-yl)benzoic acid, 28

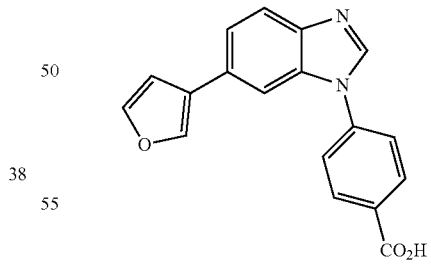

28

A suspension of 4-(6-(furan-3-yl)-1H-benzo[d]imidazol-1-yl)benzonitrile (57 mg, 2.0 mmol) and KOH (56 mg, 10.00 mmol) in MeOH (6 ml) was heated with microwave at 150° C. for 20 mins. The reaction mixture was then acidified to ~pH 4 and solvent was evaporated in vacuo. The product was purified by column chromatography (0-80%, hexane/ethylacetate) to afford 28 (52 mg, 85% yield) as a white solid.

55

4-(6-(1H-pyrazol-4-yl)-1H-benzo[d]imidazol-1-yl)benzoic acid, 29

56

4-(6-(1-methyl-1H-pyrazol-4-yl)-1H-benzo[d]imidazol-1-yl)benzoic acid, 30

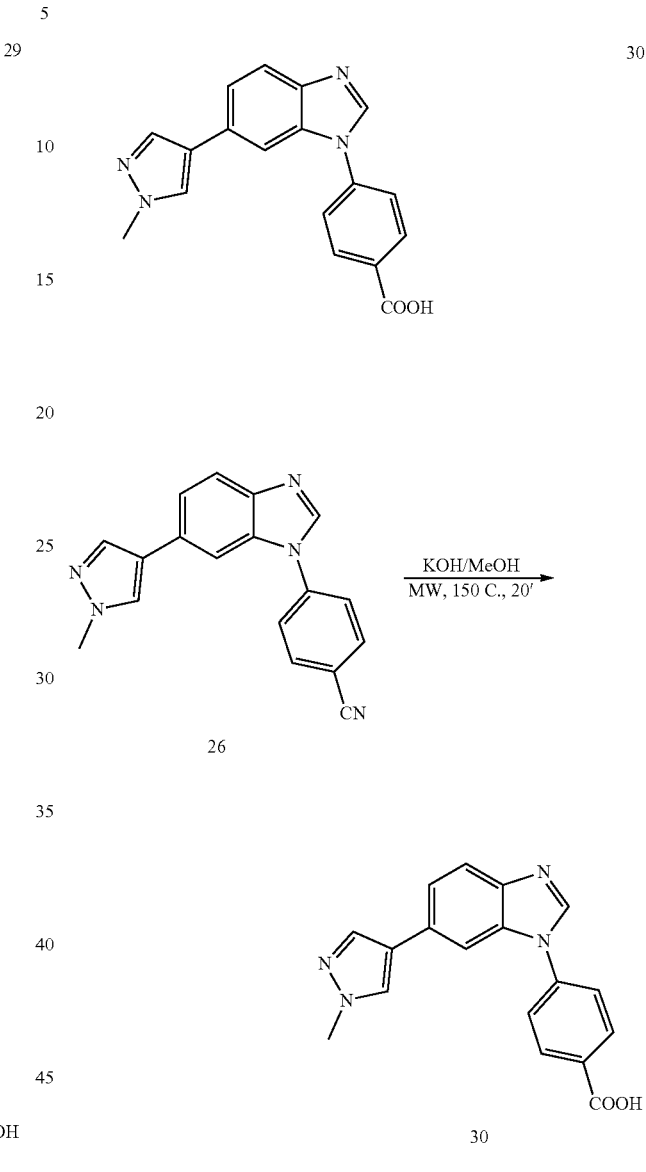

To a suspension of 25 (84 mg, 1 eq) in MeOH (1 mL), KOH (79 mg, 5 eq) was added and the resulting mixture was heated at 150° C. for 20' under microwave irradiation. After cooling down to room temperature, MeOH was removed under reduced pressure and the residue suspended in $H_2O$ (5 mL) and acidified to pH 2 by slow addition of conc. HCl. The organic layer was extracted with DCM (3×10 mL), washed with brine (1×10 mL), dried ($MgSO_4$) and the solvent removed under reduced pressure. The residue was purified by silica gel column chromatography using an ISCO system (DCM/MeOH, 0-20%) to yield 29:60 mg, 71%. LC MS [M+1]$^+$ m/z 305.00; $^1$H NMR (400 MHz, DMSO$_{d6}$) δ: 9.62 (s, 1H, N=C<u>H</u>—N), 8.32-8.16 (m, 4H, ArH), 8.06-7.77 (m, 5H, ArH); $^{13}$C NMR (100 MHz, DMSO$_{d6}$) δ: 166.4, 142.1, 137.8, 133.4, 132.2, 131.6, 131.5, 131.4, 131.2×2, 127.9, 123.7, 120.7, 117.1, 107.9.

KOH (75 mg, 5 eq.) was added to a suspension of starting material 26 (81 mg, 1 eq.) in MeOH (1 mL) and the resulting mixture was heated at 150° C. for 20' under microwave irradiation. After cooling down to room temperature, MeOH was removed under reduced pressure, the residue suspended in $H_2O$ (5 mL) and acidified to pH 2 by slow addition of conc. HCl. The water layer was extracted with DCM (3×10 mL), the organic layers collected and washed with brine (1×10 mL), dried ($MgSO_4$) and the solvent removed under reduced pressure. The residue was purified by silica gel column chromatography using an ISCO system (MeOH/DCM, 0-20%). Yield: 59 mg, 69%; LC/MS [M+1]$^+$ m/z 319.00; $^1$H NMR (400 MHz, DMSO$_{d6}$) δ: 9.40 (s, 1H, N=C<u>H</u>—N), 8.30-8.21 (m, 3H, ArH), 8.00-7.85 (m, 5H, ArH), 7.78-7.74 (m, 1H, ArH), 3.86 (s, 3H, CH$_3$); $^{13}$C NMR (100 MHz, DMSO$_{d6}$): 169.9, 143.2, 142.4, 138.3, 133.4, 133.0, 129.4, 129.0, 123.1, 121.6, 121.0, 120.2, 109.6, 106.8, 39.0.

Methyl 4-(6-(furan-3-yl)-1H-benzo[d]imidazol-1-yl)benzoate, 31

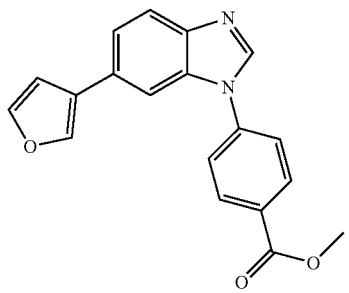

31

To a suspension of 4-(6-(furan-3-yl)-1H-benzo[d]imidazol-1-yl)benzoic acid (30.4 mg, 1.0 mmol), EDC (38 mg, 2 mmol) and DMAP (5 mg, 0.2 mmol) in DMF (3 ml) was added MeOH dropwise at room temperature. The solvent was removed and product purified by column chromatography (0-100%, ethylacetate/hexane) to afford 31 as a white solid (26 mg, 83%). 1H NMR (400 MHz, CDCl$_3$) δ 8.30-8.27 (m, 2H), 8.15 (s, 1H), 7.88-7.85 (m, 1H), 7.75 (s, 1H), 7.65-7.62 (m, 3H), 7.52-7.48 (m, 2H), 6.72 (s, 1H), 3.98 (s, 3H); 13C NMR (100 MHz, CDCl$_3$) δ 166.1, 143.9, 142.3, 140.1, 138.6, 133.8, 131.8, 129.7, 129.1, 126.7, 123.5, 122.0, 121.2, 109.2, 107.5, 52.6.

Methyl 4-(6-(pyridin-4-yl)-1H-benzo[d]imidazol-1-yl)benzoate, 32

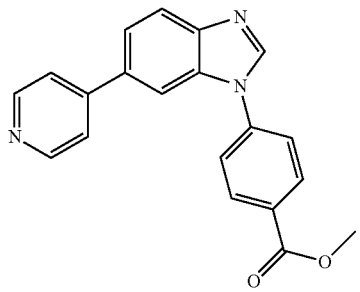

32

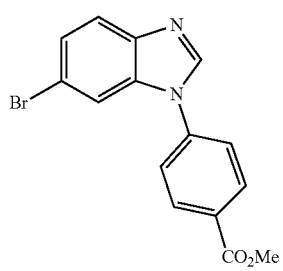

methyl 4-(6-bromo-1H-benzo[d]imidazol-1-yl)benzoate

Pd$_2$(dba)$_3$ (0.01 eq)
PCy$_3$ (0.03 eq)
Na$_2$CO$_3$ (4 eq)
DMF:H$_2$O (4:1)
0.122M
MW, 130 °C., 30 min -continued

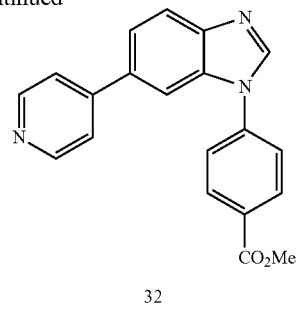

32
39%

Methyl 4-(6-bromo-1H-benzo[d]imidazol-1-yl) benzoate and reagents specified above were placed in a microwave vial, followed by addition of the designated solvent. The capped vial was purged with argon gas for 5 minutes. The reaction was then heated via microwave irradiation for 30 minutes at 130° C. After reaction completion, the crude material was filtered through celite, and the celite flushed with methanol. The remaining solvent was evaporated in vacuo via azeotropic removal with toluene. The crude material was then reabsorbed onto silica gel and product purified by flash chromatography 0-100% EtOAc/Hex or 0-100% EtOAC/DCM to afford 32 as an orange-beige solid (39% yield), $^1$H NMR (400 MHz, DMSO-d6) δ=8.77 (s, 1H), 8.66-8.59 (m, 2H), 8.24-8.16 (m, 2H), 8.05 (dd, J=1.7, 0.7, 1H), 8.03-7.88 (m, 3H), 7.83-7.72 (m, 3H), 3.92 (s, 3H). 13C NMR (100 MHz, DMSO-d6) δ=165.97, 150.58, 147.89, 145.21, 145.09, 140.11, 133.71, 133.69, 131.58, 128.92, 124.04, 122.56, 122.18, 121.17, 109.96, 52.86; M+1 (m/z): 330.

Methyl 4-(6-(1-methyl-1H-pyrazol-4-yl)-1H-benzo[d]imidazol-1-yl)benzoate, 33

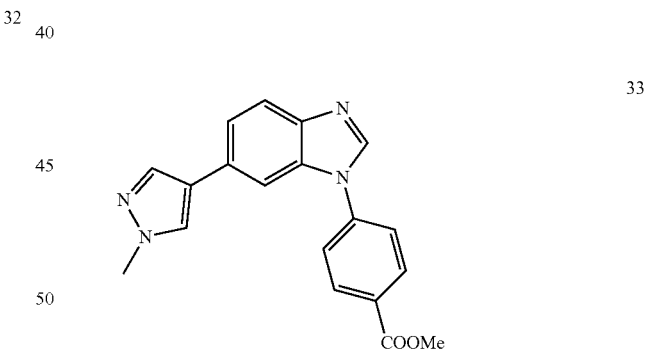

33

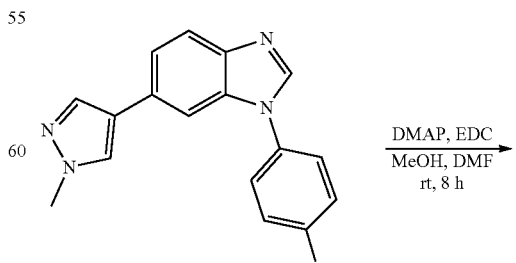

30

DMAP, EDC
MeOH, DMF
rt, 8 h

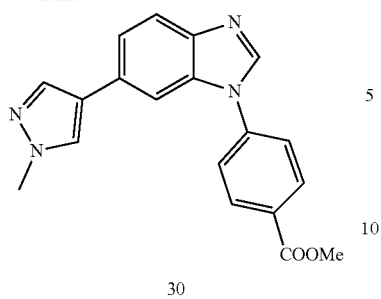

30

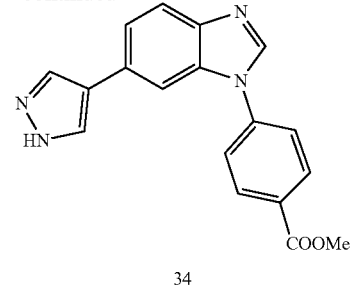

34

To a suspension of the carboxylic acid 30 (112 mg, 1 eq) in DMF (1 mL), were added DMAP (8 mg, 0.2 eq), EDC (134 mg, 2 eq) and MeOH (2 drops). The reaction was stirred at room temperature for 8 h. The solvent was removed and the final product purified by silica gel column chromatography using an ISCO system (EtOAc-hexane, 0-50%). Final yield: 41 mg, 35%; white solid; LC MS [M+1]$^+$ m/z 333.00; $^1$H NMR [400 MHz, DMSO$_{d6}$] δ: 8.62 (s, 1H, N=CH—N), 8.21-8.19 (m, 2H, ArH), 87.93-7.90 (m, 2H, ArH), 7.83-7.75 (m, 2H, ArH), 7.57-7.54 (m, 2H, ArH), 3.96 (s, 3H, OCH$_3$), 3.85 (s, 3H, NCH$_3$); $^{13}$C NMR [400 MHz, (CD$_3$)$_2$CO] δ: 165.5, 143.2, 142.4, 140.3, 136.1, 131.2, 129.3, 128.9, 127.2, 123.3, 122.9, 120.9, 120.5, 114.2, 106.7, 51.6, 38.1.

Methyl 4-(6-(1H-pyrazol-4-yl)-1H-benzo[d]imidazol-1-yl)benzoate, 34

To a suspension of the carboxylic acid 29 (35 mg, 1 eq) in DMF (1 mL), DMAP (3 mg, 0.2 eq), EDC (44 mg, 2 eq) and MeOH (2 drops) were added. The reaction was stirred at room temperature for 8 h. The solvent was removed under reduced pressure and the final product 34 purified by silica gel column chromatography using an ISCO system (EtOAc-hexane, 0-50%). Yield: 5 mg, 14%; white solid; LC MS [M+1]$^+$ m/z 305.00; $^1$H NMR (400 MHz, DMSO$_{d6}$) δ: 12.97 (brs, 1H, NH), 8.61 (s, 1H, N=CH—N), 8.37-8.10 (m, 3H, ArH), 8.07-7.82 (m, 4H, ArH), 7.66 (d, 1H, J=8.7, ArH), 7.60 (d, 1H, J=8.1 Hz, ArH), 3.92 (s, 3H, OCH$_3$); $^{13}$C NMR (100 MHz, DMSO$_{d6}$) δ: 168.5, 165.6, 143.1, 142.5, 140.0, 133.2, 131.1, 129.2, 128.2, 127.3, 123.4, 121.5, 121.1, 120.3, 106.9, 52.4.

4-(6-(pyridin-4-yl)-1H-benzo[d]imidazol-1-yl)benzamide, 35

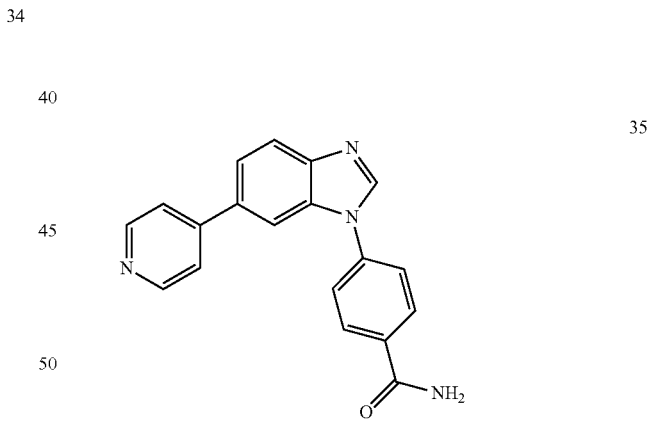

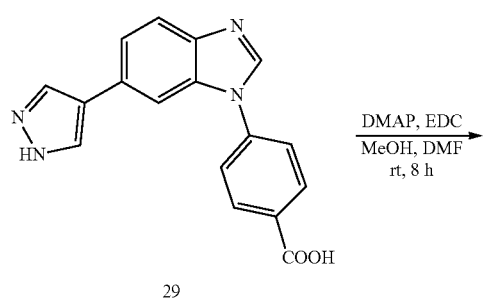

A suspension of 4-(6-(pyridin-4-yl)-1H-benzo[d]imidazol-1-yl)benzonitrile (29.6 mg, 1.0 mmol) and KOH (28 mg, 5.0 mmol) in MeOH (3 ml) was heated in a microwave at 100° C. for 20 mins. The solvent was evaporated in vacuo and product purified by column chromatography (0-50%, hexane/ethylacetate) to afford 38 (22 mg, 70% yield) as a white solid. 1H NMR (400 MHz, CDCl$_3$) δ 8.67-8.66 (m, 2H), 8.10-7.98 (m, 3H), 7.78 (s, 1H), 7.68-7.65 (m, 3H), 7.54-7.53 (m, 2H), 5.30 (s, 2H).

4-(6-(furan-3-yl)-1H-benzo[d]imidazol-1-yl)benzamide, 36

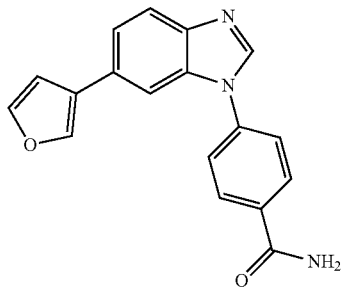

¹H NMR (400 MHz, MeOD) 8.47 (s, 1H), 8.19-8.21 (m, 2H), 7.91 (s, 1H), 7.20-7.27 (4H, 2×m), 7.5-7.65 (2H, 2×m), 6.80 (1H, s), 5.5 (2H, s). ¹³C NMR (100 MHz, MeOD) δ 169.61, 143.72, 142.77, 142.18, 138.77, 138.74, 133.49, 133.29, 129.39, 129.31, 126.47, 123.52, 123.51, 121.67, 119.56, 108.49, 107.22. [M+H]$^+$=304

2-morpholino-N-(4-(6-(pyridin-4-yl)-1H-benzo[d]imidazol-1-yl)phenyl)acetamide, 39

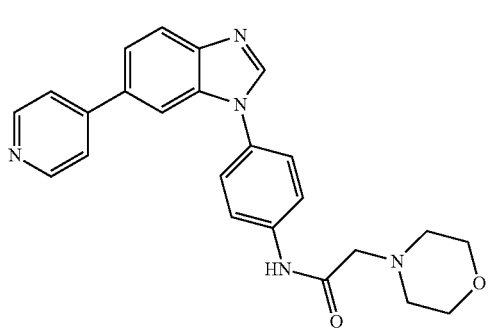

Yellow solid. Mp: 220-222° C. ¹H NMR (400 MHz, CDCl$_3$) δ 9.30 (s, 1H), 8.64 (d, J=4.5 Hz, 2H), 8.15 (s, 1H), 7.97 (d, J=8.4 Hz, 1H), 7.84 (d, J=8.5 Hz, 2H), 7.71 (s, 1H), 7.63 (d, J=8.4 Hz, 1H), 7.52 (d, J=8.7 Hz, 3H), 3.98-3.69 (m, 4H), 3.17 (d, J=34.4 Hz, 2H), 2.72 (dd, J=37.6, 33.6 Hz, 4H). ¹³C NMR (100 MHz, CDCl$_3$) δ 168.29, 150.10, 148.72, 144.50, 143.52, 137.69, 134.61, 134.17, 131.73, 125.17, 122.17, 121.95, 121.19, 120.93, 108.95, 67.01, 62.41, 53.83. LC/MS [M+1]+=414

2-morpholino-N-(4-(6-(pyridin-3-yl)-1H-benzo[d]imidazol-1-yl)phenyl)acetamide, 40

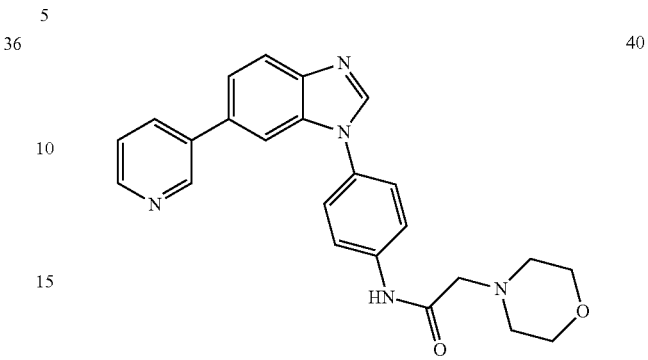

Orange solid. Mp: 85-89° C. ¹H NMR (400 MHz, CDCl$_3$) δ 9.33 (d, J=26.4 Hz, 1H), 8.86 (s, 1H), 8.59 (d, J=4.6 Hz, 1H), 8.14 (s, 1H), 7.97 (d, J=8.4 Hz, 1H), 7.94-7.88 (m, 1H), 7.83 (d, J=8.4 Hz, 2H), 7.65 (d, J=0.8 Hz, 1H), 7.55 (ddd, J=15.5, 8.1, 4.6 Hz, 3H), 7.37 (dd, J=7.9, 4.8 Hz, 1H), 3.91-3.71 (m, 4H), 3.19 (t, J=15.7 Hz, 2H), 2.76-2.59 (m, 4H). ¹³C NMR (100 MHz, CDCl$_3$) δ 168.16, 148.48, 148.24, 143.86, 143.16, 137.60, 137.03, 134.72, 133.91, 131.86, 125.12, 123.54, 122.46, 121.17, 120.88, 108.95, 66.99, 62.40, 53.82. LC/MS [M+1]+=414

2-Morpholino-N-(4-(6-(pyrimidin-5-yl)-1H-benzo[d]imidazol-1-yl)phenyl)acetamide, 41

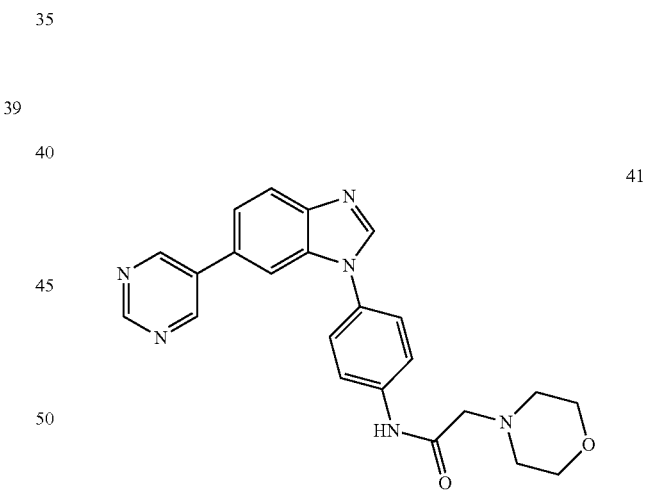

Yellow solid. Mp: 191-193° C. ¹H NMR (400 MHz, CDCl$_3$) δ 9.43-9.08 (m, 2H), 8.97 (s, 2H), 8.17 (s, 1H), 8.01 (d, J=8.4 Hz, 1H), 7.83 (t, J=13.0 Hz, 2H), 7.65 (s, 1H), 7.54 (dd, J=12.5, 8.6 Hz, 2H), 3.91-3.73 (m, 4H), 3.22 (s, 2H), 2.85-2.60 (m, 4H). ¹³C NMR (100 MHz, CDCl$_3$) δ 168.27, 157.28, 155.11, 143.63, 137.83, 134.78, 131.62, 130.18, 125.20, 122.11, 121.68, 120.95, 108.99, 67.02, 62.43, 53.85. LC/MS [M+1]+=415

N-(4-(6-(pyridin-4-yl)-1H-benzo[d]imidazol-1-yl)benzyl)acetamide, 42

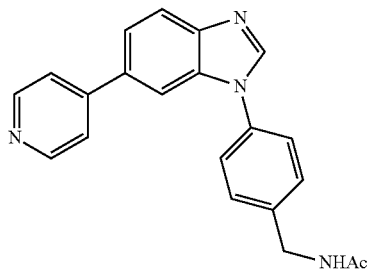

Brown solid. Mp: 81-83° C. ¹H NMR (400 MHz, CDCl₃) δ 8.62 (d, J=6.0 Hz, 2H), 8.09 (d, J=5.8 Hz, 1H), 7.95 (d, J=8.5 Hz, 1H), 7.72 (d, J=1.6 Hz, 1H), 7.62 (dd, J=8.4, 1.7 Hz, 1H), 7.58-7.47 (m, 5H), 6.48 (s, 1H), 4.55 (t, J=8.1 Hz, 2H), 2.10 (s, 3H). ¹³C NMR (100 MHz, CDCl₃) δ 170.26, 150.10, 148.71, 144.57, 143.46, 139.22, 135.03, 134.40, 134.21, 129.53, 124.46, 122.25, 121.98, 121.18, 109.03, 43.06, 23.27. LC/MS [M+1]+=343

N-(4-(6-(pyridin-3-yl)-1H-benzo[d]imidazol-1-yl)benzyl)acetamide, 43

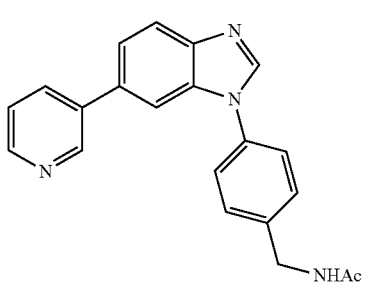

Brown solid. Mp: 217-219° C. ¹H NMR (400 MHz, DMSO-d6) δ 7.59 (d, J=2.0 Hz, 1H), 7.21 (dd, J=4.7, 1.3 Hz, 1H), 7.12 (t, J=5.9 Hz, 1H), 6.85-6.73 (m, 1H), 6.52 (dd, J=18.1, 5.0 Hz, 2H), 6.38 (dd, J=8.7, 2.1 Hz, 2H), 6.30 (dd, J=8.4, 1.7 Hz, 1H), 6.20-6.06 (m, 3H), 3.02 (t, J=9.0 Hz, 2H), 1.99 (s, 2H), 1.15 (dt, J=3.5, 1.8 Hz, 1H). ¹³C NMR (100 MHz, DMSO-d6) δ 174.45, 153.35, 153.25, 149.50, 148.96, 144.66, 141.37, 139.77, 139.58, 138.92, 138.04, 134.08, 129.00, 128.88, 127.11, 125.70, 114.37, 46.85, 27.79. LC/MS [M+1]+=343

N-(4-(6-(thiophen-3-yl)-1H-benzo[d]imidazol-1-yl)benzyl)acetamide, 44

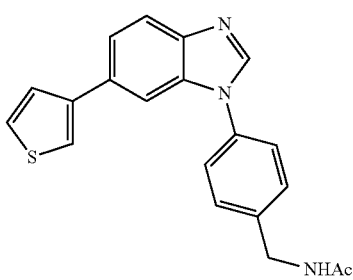

Brown solid. Mp: 188-190° C. ¹H NMR (400 MHz, CDCl₃) δ 7.98 (s, 1H), 7.86 (d, J=8.4 Hz, 1H), 7.65 (s, 1H), 7.59 (dd, J=8.4, 1.2 Hz, 1H), 7.54-7.44 (m, 4H), 7.44-7.40 (m, 1H), 7.40-7.35 (m, 2H), 6.35 (s, 1H), 4.54 (d, J=5.9 Hz, 2H), 2.10 (s, 3H). ¹³C NMR (100 MHz, CDCl₃) δ 170.18, 143.10, 142.60, 142.48, 138.84, 135.30, 134.21, 132.27, 129.47, 126.63, 126.32, 124.37, 122.24, 120.65, 120.29, 108.08, 43.08, 23.26. LC/MS [M+1]+=348

N-(4-(6-phenyl-1H-benzo[d]imidazol-1-yl)benzyl)acetamide, 45

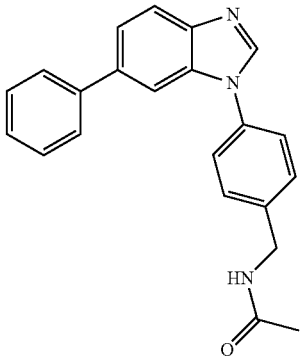

Brown oil. ¹H NMR (400 MHz, CDCl₃) δ 8.02 (d, J=7.0 Hz, 1H), 7.91 (d, J=8.4 Hz, 1H), 7.68 (dd, J=16.3, 5.2 Hz, 1H), 7.64-7.56 (m, 2H), 7.55-7.29 (m, 7H), 6.30 (s, 1H), 4.64-4.48 (m, 2H), 2.09 (s, 3H). ¹³C NMR (100 MHz, CDCl₃) δ 170.29, 142.61, 141.42, 138.80, 137.75, 135.33, 134.23, 129.47, 129.42, 129.25, 128.80, 128.53, 127.51, 127.21, 124.39, 124.23, 122.88, 120.56, 120.23, 119.06, 108.93, 43.11, 23.25. LC/MS [M+1]+=342.

N-(4-(6-(pyrimidin-5-yl)-1H-benzo[d]imidazol-1-yl)benzyl)acetamide, 46

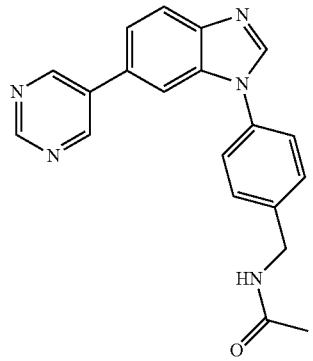

Brown solid. Mp: 205-207° C. $^1$H NMR (400 MHz, CDCl$_3$) δ 9.19 (s, 1H), 8.97 (s, 2H), 8.16 (d, J=14.1 Hz, 1H), 8.01 (d, J=8.4 Hz, 1H), 7.71 (d, J=39.9 Hz, 1H), 7.61-7.45 (m, 4H), 6.08 (s, 1H), 4.56 (d, J=6.0 Hz, 2H), 2.10 (s, 3H), 1.87 (s, 1H). $^{13}$C NMR (100 MHz, CDCl$_3$) δ 170.12, 157.31, 155.12, 144.46, 143.52, 139.27, 135.02, 134.76, 134.60, 130.24, 129.60, 124.52, 122.17, 121.69, 109.07, 43.10, 23.30. LC/MS [M+1]$^+$=344

N-(4-(6-(6-methoxypyridin-3-yl)-1H-benzo[d]imidazol-1-yl)benzyl)acetamide, 47

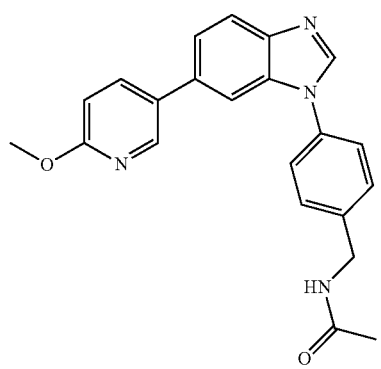

Brown solid. Mp: 71-73° C. $^1$H NMR (400 MHz, CDCl$_3$) δ 8.16 (dt, J=12.2, 6.1 Hz, 1H), 8.08 (s, 1H), 7.90 (d, J=8.4 Hz, 1H), 7.67 (d, J=1.1 Hz, 1H), 7.62 (dd, J=7.3, 1.9 Hz, 1H), 7.53 (dd, J=8.4, 1.6 Hz, 1H), 7.50 (s, 4H), 7.02-6.94 (m, 1H), 6.02 (s, 1H), 4.54 (d, J=6.0 Hz, 2H), 3.96 (s, 3H), 2.09 (d, J=2.8 Hz, 3H). $^{13}$C NMR (100 MHz, CDCl$_3$) δ 170.08, 160.88, 145.72, 142.71, 138.90, 138.65, 135.44, 132.76, 129.42, 124.89, 124.57, 124.30, 120.16, 117.09, 111.15, 53.63, 43.11, 23.31. LC/MS [M+1]+=373.

N-(4-(6-(3,4-difluorophenyl)-1H-benzo[d]imidazol-1-yl)benzyl)acetamide, 48

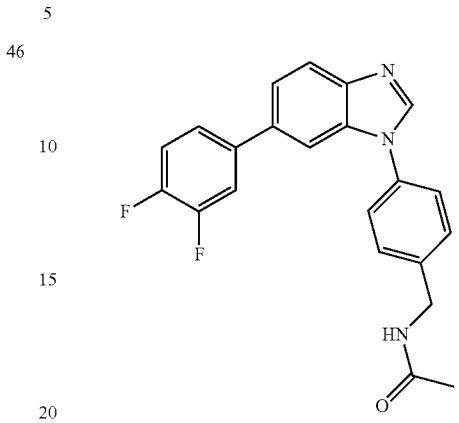

Brown solid. Mp: 62-64° C. $^1$H NMR (400 MHz, CDCl$_3$) δ 8.09 (s, 1H), 7.91 (t, J=7.4 Hz, 1H), 7.59 (d, J=1.4 Hz, 1H), 7.56-7.48 (m, 4H), 7.43-7.34 (m, 1H), 7.33-7.28 (m, 1H), 7.25-7.17 (m, 1H), 6.08 (s, 1H), 4.54 (dd, J=10.6, 6.0 Hz, 2H), 2.10 (s, 3H), 1.86 (brs, 1H). $^{13}$C NMR (100 MHz, CDCl$_3$) δ 170.14, 143.61, 143.02, 138.96, 135.51, 135.23, 134.31, 129.52, 124.48, 123.40, 123.34, 122.49, 120.92, 117.62, 117.45, 116.41, 116.24, 108.82, 43.11, 23.31.

4-(4-(6-(pyridin-4-yl)-1H-benzo[d]imidazol-1-yl)phenyl)morpholine, 49

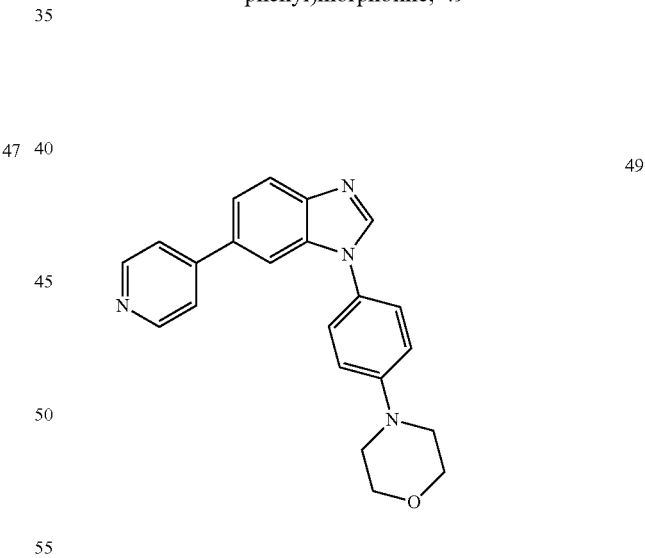

Brown solid. Mp: 207-209° C. $^1$H NMR (400 MHz, CDCl$_3$) δ 8.65 (d, J=4.3 Hz, 2H), 8.11 (s, 1H), 7.95 (d, J=8.4 Hz, 1H), 7.74-7.66 (m, 1H), 7.61 (dd, J=8.4, 1.5 Hz, 1H), 7.53 (d, J=5.5 Hz, 2H), 7.45-7.38 (m, 2H), 7.09 (t, J=6.0 Hz, 2H), 3.96-3.87 (m, 4H), 3.33-3.22 (m, 4H). 13C NMR (100 MHz, CDCl$_3$) δ 151.26, 150.14, 148.84, 144.55, 143.93, 135.08, 133.89, 127.56, 125.61, 121.99, 121.90, 121.07, 116.29, 109.06, 66.74, 48.84. LC/MS [M+1]+=357.

4-(4-(6-(pyridin-4-yl)-1H-benzo[d]imidazol-1-yl)benzyl)morpholine, 50

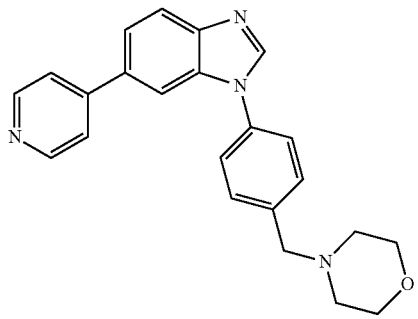

Brown solid. Mp: 166-168° C. $^1$H NMR (400 MHz, DMSO-d6) δ 8.61 (m, 3H), 8.24 (s, 1H), 8.00-7.84 (m, 2H), 7.78-7.64 (m, 4H), 7.58 (d, J=8.0 Hz, 2H), 3.62 (m, 4H), 3.33 (s, 2H), 2.59-2.39 (m, 4H). $^{13}$C NMR (100 MHz, DMSO-d6) δ 150.39, 148.09, 144.96, 138.23, 134.98, 133.43, 130.80, 124.01, 122.01, 120.95, 109.55, 79.61, 79.28, 78.95, 66.68, 62.34, 53.64. LC/MS [M+1]+=371

4-(4-(6-phenyl-1H-benzo[d]imidazol-1-yl)benzyl)morpholine, 51

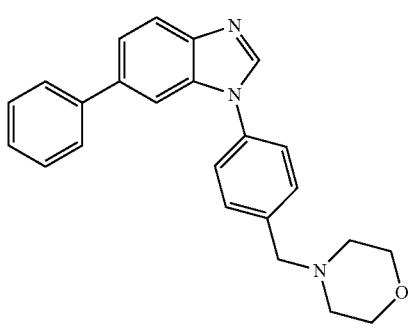

Yellow solid. Mp: 111-113° C. $^1$H NMR (400 MHz, CDCl3) δ 8.14 (s, 1H), 7.93 (d, J=8.4 Hz, 1H), 7.70 (t, J=3.9 Hz, 1H), 7.62 (t, J=1.7 Hz, 1H), 7.60 (dd, J=2.2, 1.4 Hz, 1H), 7.59-7.56 (m, 1H), 7.55 (d, J=2.1 Hz, 1H), 7.53-7.40 (m, 5H), 7.39-7.31 (m, 1H), 3.74 (dd, J=15.9, 11.2 Hz, 4H), 3.60 (s, 2H), 2.60-2.43 (m, 4H). $^{13}$C NMR (100 MHz, CDCl$_3$) δ 142.85, 141.62, 138.32, 137.62, 135.17, 134.30, 130.68, 128.76, 127.56, 127.14, 124.04, 122.77, 120.66, 110.01, 109.00, 67.01, 62.76, 53.67. LC/MS [M+1]+=370

4-(4-(6-(furan-3-yl)-1H-benzo[d]imidazol-1-yl)benzyl)morpholine, 52

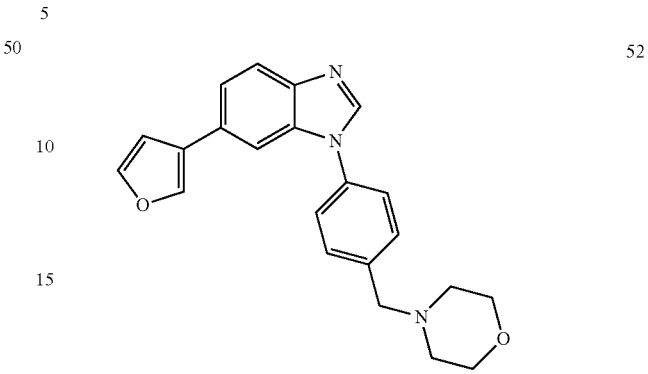

Brown solid. Mp: 119-121° C. $^1$H NMR (400 MHz, CDCl$_3$) δ 8.10 (d, J=10.5 Hz, 1H), 7.86 (dd, J=8.4, 0.5 Hz, 1H), 7.72 (ddd, J=9.0, 3.6, 2.1 Hz, 1H), 7.58 (dd, J=4.8, 4.3 Hz, 3H), 7.52-7.45 (m, 4H), 6.74-6.70 (m, 1H), 3.75 (dd, J=13.9, 9.3 Hz, 4H), 3.61 (s, 2H), 2.49 (d, J=31.1 Hz, 4H). $^{13}$C NMR (100 MHz, CDCl$_3$) δ 143.68, 143.28, 142.64, 138.45, 130.72, 128.53, 126.84, 124.05, 121.54, 120.85, 109.21, 107.50, 106.33, 66.99, 62.76, 53.68. LC/MS [M+1]+=358

4-(4-(6-(1-methyl-1H-pyrazol-4-yl)-1H-benzo[d]imidazol-1-yl)benzyl)morpholine, 53

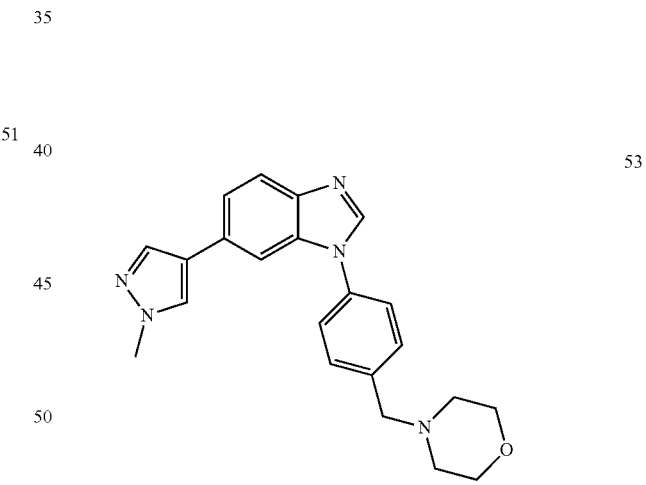

Brown solid. Mp: 105-107° C. $^1$H NMR (400 MHz, DMSO-d6) δ 8.35 (d, J=32.9 Hz, 1H), 8.10 (d, J=17.5 Hz, 1H), 7.81 (s, 1H), 7.76-7.67 (m, 2H), 7.64 (d, J=8.0 Hz, 2H), 7.57 (d, J=7.9 Hz, 2H), 7.49 (d, J=8.4 Hz, 1H), 3.86 (d, J=13.3 Hz, 3H), 3.61 (m, 4H), 3.33 (s, 2H), 2.49 (m, 4H). $^{13}$C NMR (100 MHz, DMSO-d6) δ 143.40, 142.82, 136.46, 135.24, 134.16, 130.74, 128.84, 128.07, 123.84, 122.88, 120.91, 120.55, 106.88, 66.68, 62.36, 53.64, 39.42.

1-(4-methoxyphenyl)-5-(1H-pyrazol-4-yl)-1H-benzo[d]imidazole, 54

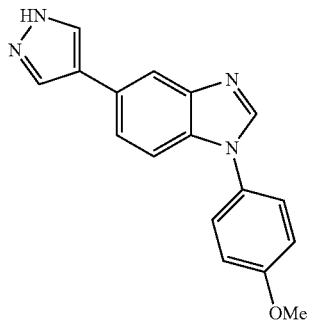

¹H NMR (400 MHz, CDCl₃) δ 8.16-7.84 (m, 4H), 7.55-7.38 (m, 4H), 7.13-7.04 (m, 2H), 3.90 (dd, J=3.5, 2.3 Hz, 3H). ¹³C NMR (100 MHz, CDCl₃) δ 159.39, 144.43, 143.17, 131.92, 129.05, 128.47, 127.42, 125.63, 122.17, 117.25, 115.17, 110.72, 55.67. LC/MS [M+1]+=291.

4-(5-(pyridin-4-yl)-1H-benzo[d]imidazol-1-yl)benzonitrile, 55

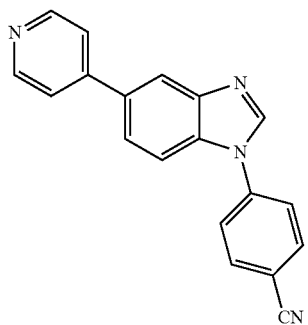

¹H NMR (400 MHz, d6-DMSO) δ 8.76 (d, J=5.7 Hz, 1H), 8.62 (d, J=5.7 Hz, 2H), 8.25 (s, 1H), 8.12 (d, J=8.4 Hz, 2H), 7.97 (d, J=8.4 Hz, 2H), 7.89-7.73 (m, 5H). ¹³C NMR (100 MHz, d6-DMSO) δ 150.63, 147.60, 145.24, 144.88, 140.01, 134.79, 133.52, 132.82, 124.41, 123.33, 121.84, 118.99, 118.74, 112.16, 110.51. LC/MS [M+1]+=297

4-(5-(pyridin-4-yl)-1H-benzo[d]imidazol-1-yl)benzamide, 56

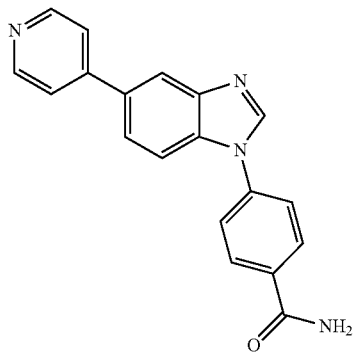

¹H NMR (400 MHz, d6-DMSO) δ 8.69 (d, J=5.7 Hz, 1H), 8.57 (d, J=6.0 Hz, 2H), 8.21 (s, 1H), 8.08 (d, J=8.6 Hz, 3H), 7.79 (s, 1H), 7.76 (dd, J=6.1, 2.5 Hz, 5H), 7.47 (s, 1H). ¹³C NMR (100 MHz, d6-DMSO) δ 167.28, 150.63, 147.75, 145.13, 144.94, 138.48, 133.90, 133.73, 132.51, 129.83, 123.49, 123.14, 121.84, 118.89, 112.10. LC/MS [M+1]+=315.

4-(5-(pyridin-4-yl)-1H-benzo[d]imidazol-1-yl)benzoic acid, 57

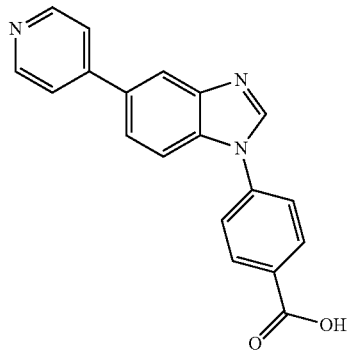

¹H NMR (400 MHz, d6-DMSO) δ 8.75 (s, 1H), 8.62 (d, J=5.4 Hz, 2H), 8.27 (t, J=5.9 Hz, 1H), 8.16 (dt, J=14.6, 4.3 Hz, 2H), 7.84 (ddd, J=17.0, 9.8, 3.5 Hz, 6H). ¹³C NMR (100 MHz, d-DMSO) δ 150.63, 147.72, 145.18, 144.90, 133.81, 132.59, 131.60, 123.58, 123.19, 121.85, 118.94, 112.13. LC/MS [M+1]+=316.

1-(3,4-dimethoxyphenyl)-6-(4-pyridinyl)-1H-benzo[d]imidazole, 58

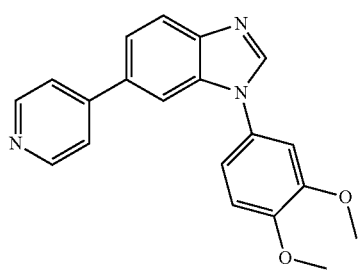

6-bromo-1-(3,4-dimethoxyphenyl)-1H-benzo[d]imidazole (0.300 mmol, 100 mg), pyridine-4-boronic acid (1.0 eq., 0.300 mmol, 38.8 mg), Na₂CO₃ (4.0 eq., 1.20 mmol, 127 mg), and a mixture of 4:1 DMF/water (3 mL) were added to a microwave vial. The vial was purged with Ar(g) then tris(dibenzylideneacetone)dipalladium (0) (Pd₂(dba)₃, 0.01 eq., 3.0 μmol, 2.9 mg) and tricyclohexylphosphine (0.03 eq., 9.0 μmol, 2.6 mg) was added. The reaction was microwave irradiated under Ar (g) at 130° C. for 30 min. then filtered through celite washing down with CH₂Cl₂ and MeOH. The filtrate was evaporated in vacuo and DMF was removed by azeotroping with toluene. The crude material was purified via flash chromatography eluting with a CH₂Cl₂/MeOH gradient to obtain 65 (0.232 mmol, 76.9 mg). Yield: 77%, light red solid. $^1$H NMR (400 MHz, DMSO-d6) δ 8.59 (d, J=5.4 Hz, 2H), 8.57 (s, 1H), 7.87 (d, J=8.6 Hz, 2H), 7.73 (d, J=6.1 Hz, 2H), 7.70 (dd, J=8.5, 1.6 Hz, 1H), 7.30 (d, J=2.3 Hz, 1H), 7.25 (dd, J=8.5, 2.4 Hz, 1H), 7.16 (d, J=8.6 Hz, 1H), 3.84 (s, 6H). $^{13}$C NMR (100 MHz, DMSO-d6) δ 150.57, 150.03, 148.94, 148.00, 145.50, 144.79, 134.75, 133.08, 129.04, 122.08, 121.90, 120.87, 116.63, 112.76, 109.65, 109.13, 56.30; [M+H]$^+$=332.0.

1-(3,4-ethylenedioxyphenyl)-6-(4-pyridinyl)-H-benzo[d]imidazole, 59

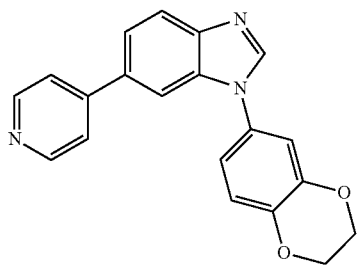

59

6-bromo-1-(3,4-ethylenedioxyphenyl)-1H-benzo[d]imidazole (0.151 mmol, 50.0 mg), pyridine-4-boronic acid (1.0 eq., 0.151 mmol, 19.6 mg), Na$_2$CO$_3$ (4.0 eq., 0.604 mmol, 64.0 mg), and a mixture of 4:1 DMF/water (2 mL) were added to a microwave vial. The vial was purged with Ar(g) then tris(dibenzylideneacetone)dipalladium (0) (Pd$_2$(dba)$_3$, 0.01 eq., 1.6 μmol, 1.5 mg) and tricyclohexylphosphine (0.03 eq., 4.6 μmol, 1.4 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via flash chromatography eluting with a hexanes/EtOAc gradient to obtain 66 (0.097 mmol, 31.8 mg). Yield: 64%, dark purple solid. $^1$H NMR (400 MHz, DMSO-d6) δ 8.61 (d, J=4.8 Hz, 2H), 8.55 (d, J=1.1 Hz, 1H), 7.88 (d, J=8.4 Hz, 1H), 7.86 (s, 1H), 7.75 (dt, J=4.5, 1.2 Hz, 2H), 7.71 (dt, J=8.4, 1.3 Hz, 1H), 7.29 (dd, J=2.5, 1.1 Hz, 1H), 7.21 (ddd, J=8.6, 2.5, 1.1 Hz, 1H), 7.10 (dd, J=8.6, 1.1 Hz, 1H), 4.34 (d, J=0.9 Hz, 4H). $^{13}$C NMR (100 MHz, DMSO-d6) δ 150.14, 147.61, 144.98, 144.33, 144.09, 143.25, 134.11, 132.75, 128.95, 121.67, 121.54, 120.46, 118.11, 117.17, 113.27, 109.14, 64.23, 64.13; [M+H]$^+$=330.0.

1-(3,4-methylenedioxyphenyl)-6-(2-fluoro-4-pyridinyl)-1H-benzo[d]imidazole, 60

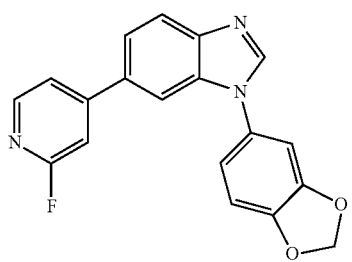

60

6-bromo-1-(3,4-methylenedioxyphenyl)-1H-benzo[d]imidazole (0.315 mmol, 100 mg), 2-fluoro-pyridine-4-boronic acid (1.0 eq., 0.315 mmol, 45.8 mg), Na$_2$CO$_3$ (4.0 eq., 1.26 mmol, 134 mg), and a mixture of 4:1 DMF/water (3.5 mL) were added to a microwave vial. The vial was purged with Ar(g) then tris(dibenzylideneacetone)dipalladium (0) (Pd$_2$(dba)$_3$, 0.01 eq., 3.2 μmol, 3.0 mg) and tricyclohexylphosphine (0.03 eq., 9.5 μmol, 2.8 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via flash chromatography eluting with a hexanes/EtOAc gradient to obtain 67 (0.270 mmol, 90.5 mg). Yield: 86%, light purple solid. $^1$H NMR (400 MHz, DMSO-d6) δ 8.57 (s, 1H), 8.27 (d, J=5.3 Hz, 1H), 7.94 (d, J=1.7 Hz, 1H), 7.88 (d, J=8.5 Hz, 1H), 7.79-7.72 (m, 2H), 7.60 (s, 1H), 7.41 (d, J=2.2 Hz, 1H), 7.20 (dd, J=8.2, 2.2 Hz, 1H), 7.14 (d, J=8.2 Hz, 1H), 6.17 (s, 2H). $^{13}$C NMR (100 MHz, DMSO-d6) δ 165.25, 162.93, 153.81 (d, J=8.6 Hz), 148.30, 147.91 (d, J=15.9 Hz), 147.04, 145.36, 144.71, 134.12, 131.50 (d, J=3.5 Hz), 129.50, 121.74, 120.42, 120.09 (d, J=3.7 Hz), 117.89, 109.76, 108.89, 107.10, 106.72, 105.92, 102.03; [M+H]$^+$=334.0.

1-(3,4-methylenedioxyphenyl)-6-(2-methyl-4-pyridinyl)-1H-benzo[d]imidazole, 61

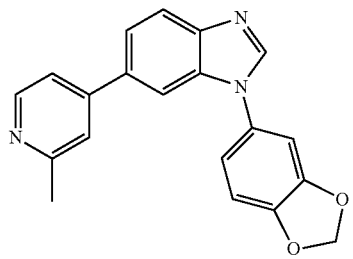

61

6-bromo-1-(3,4-methylenedioxyphenyl)-1H-benzo[d]imidazole (0.315 mmol, 100 mg), 2-fluoro-pyridine-4-boronic acid (1.0 eq., 0.315 mmol, 43.2 mg), Na$_2$CO$_3$ (4.0 eq., 1.26 mmol, 134 mg), and a mixture of 4:1 DMF/water (3.5 mL) were added to a microwave vial. The vial was purged with Ar(g) then tris(dibenzylideneacetone)dipalladium (0) (Pd$_2$(dba)$_3$, 0.01 eq., 3.2 μmol, 3.0 mg) and tricyclohexylphosphine (0.03 eq., 9.5 μmol, 2.8 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via flash chromatography eluting with a hexanes/EtOAc gradient to obtain 68 (0.180 mmol, 58.9 mg). Yield: 57%, off-white oil. A portion of the product was further purified through preparative reverse phase LCMS eluting with a water/acetonitrile gradient to obtain an analytically pure sample. $^1$H NMR (400 MHz, DMSO-d6) δ 8.73 (br. s, 2H), 7.93 (br. s, 2H), 7.70 (br. s, 2H), 7.61 (br. s, 1H), 7.40 (s, 1H), 7.17 (q, J=8.2 Hz, 2H), 6.17 (s, 2H), 2.54 (s, 3H). [M+H]$^+$=330.0.

1-(3,4-methylenedioxyphenyl)-6-(1H-pyrazol-4-yl)-1H-benzo[d]imidazole, 62

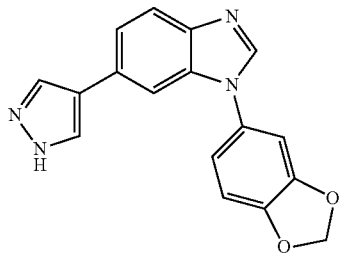

6-bromo-1-(3,4-methylenedioxyphenyl)-1H-benzo[d]imidazole (0.315 mmol, 100 mg), (1H-pyrazol-4-yl) boronic acid pinacol ester (1.0 eq., 0.315 mmol, 64.4 mg), Na$_2$CO$_3$ (4.0 eq., 1.26 mmol, 134 mg), and a mixture of 4:1 DMF/water (3.5 mL) were added to a microwave vial. The vial was purged with Ar(g) then tris(dibenzylideneacetone)dipalladium (0) (Pd$_2$(dba)$_3$, 0.01 eq., 3.2 μmol, 3.0 mg) and tricyclohexylphosphine (0.03 eq., 9.5 μmol, 2.8 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via flash chromatography eluting with a CH$_2$Cl$_2$/MeOH gradient to obtain 69 (0.270 mmol, 82.0 mg). Yield: 85%, pink solid. $^1$H NMR (400 MHz, DMSO-d6) δ 12.91 (br. s, 1H), 8.38 (s, 1H), 8.08 (br. s, 2H), 7.72 (d, J=8.4 Hz, 1H), 7.68 (d, J=1.3 Hz, 1H), 7.55 (dd, J=8.4, 1.6 Hz, 1H), 7.34 (t, J=1.3 Hz, 1H), 7.14 (d, J=1.4 Hz, 2H), 6.17 (s, 2H). $^{13}$C NMR (100 MHz, DMSO-d6) δ 148.27, 146.85, 143.55, 142.08, 134.23, 129.89, 128.70, 121.68, 120.66, 120.03, 117.75, 108.89, 106.55, 105.87, 101.98; [M+H]$^+$=305.0.

1-(4-methoxyphenyl)-6-(pyridin-4-yl)-1H-benzo[d]imidazol-2-amine, 63

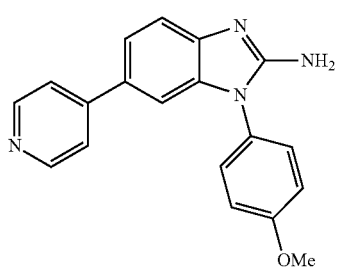

$^1$H NMR (400 MHz, CDCl$_3$) δ 8.56 (d, J=5.9 Hz, 2H), 7.51 (d, J=8.2 Hz, 1H), 7.49-7.44 (m, 3H), 7.44-7.36 (m, 2H), 7.18 (d, J=1.6 Hz, 1H), 7.16-7.10 (m, 2H), 5.13 (d, J=10.8 Hz, 2H), 3.91 (d, J=0.5 Hz, 3H). $^{13}$C NMR (100 MHz, CDCl$_3$) δ 160.10, 150.01, 149.02, 143.20, 130.19, 128.34, 126.67, 121.42, 121.25, 116.60, 115.71, 106.72, 55.66.

N-(1-(4-methoxyphenyl)-6-(pyridin-4-yl)-1H-benzo[d]imidazol-2-yl)acetamide, 64

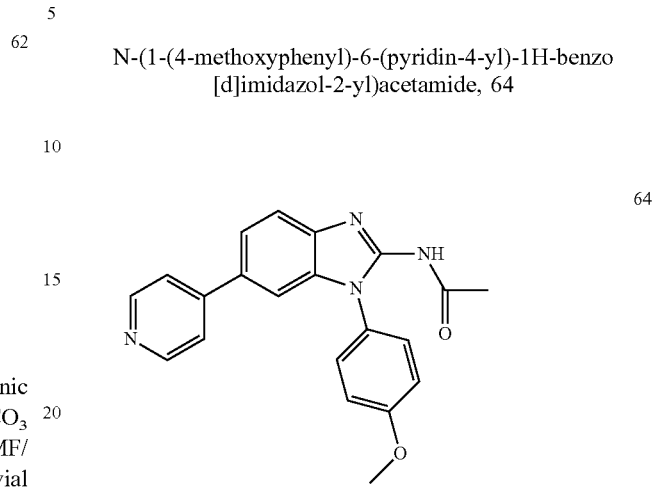

$^1$H NMR (400 MHz, CDCl$_3$) δ 8.55-8.60 (m, 2H), 7.5-7.6 (2×m, 4H), 7.25-7.39 (m, 3H), 7.05-7.25 (m, 2H), 3.91 (s, 3H), 2.33 (s, 3H). $^{13}$C NMR (100 MHz, CDCl$_3$) δ160.17, 150.21, 150.15, 150.03, 148.31, 128.43, 128.37, 122.28, 121.67, 121.44, 121.35, 116.41, 115.76, 115.32, 108.35, 106.81, 55.69; [M+H]$^+$=359.0.

1-acetyl-N-(1-(4-methoxyphenyl)-6-(pyridin-4-yl)-1H-benzo[d]imidazol-2-yl)piperidine-4-carboxamide, 65

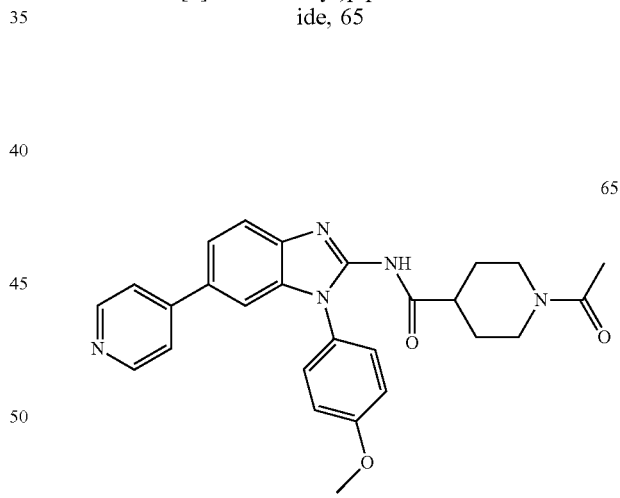

$^1$H NMR (400 MHz, CDCl$_3$) δ 8.61-8.64 (m, 2H), 7.50-7.60 (m, 1H), 7.4-7.5 (m, 4H), 7.3 (s, 1H), 7.25 (s, 1H), 7.09-7.12 (m, 2H), 4.47-4.50 (m, 1H), 3.95 (s, 3H), 3.48-3.52 (m, 1H), 3.1-3.2 (m, 1H), 2.72-2.78 (m, 1H), 2.6 (br s, 1H), 2.09 (s, 3H), 1.8-2.0 (m, 2H), 1.55-1.75 (m, 2H). $^{13}$C NMR (100 MHz, CDCl$_3$) δ168.84, 159.74, 150.20, 148.03, 133.79, 128.25, 126.20, 122.63, 121.66, 114.92, 108.55, 55.61, 46.09, 41.26, 29.16, 28.71, 21.54; [M+H]$^+$=470.0.

2-(3,5-difluorophenyl)-N-(1-(4-methoxyphenyl)-6-(pyridin-4-yl)-1H-benzo[d]imidazol-2-yl)acetamide, 66

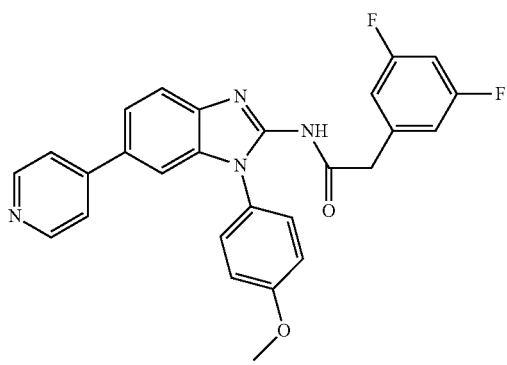

66

$^1$H NMR (400 MHz, CDCl$_3$) δ 12.1-12.5 (br s, 1H), 7.25-7.55 (3×m, 7H), 7.41-7.19 (m, 2H), 6.83-6.91 (m, 2H), 6.60-6.75 (m, 1H), 3.93 (s, 3H), 3.70-3.74 (m, 2H). $^{13}$C NMR (100 MHz, CDCl$_3$) δ164.03, 163.90, 161.57, 161.44, 159.86, 150.27, 147.93, 133.95, 128.31, 125.96, 122.73, 121.65, 114.94, 112.64, 112.39, 108.61, 101.79, 55.62.

2-amino-N-(1-(4-methoxyphenyl)-6-(pyridin-4-yl)-1H-benzo[d]imidazol-2-yl)acetamide, 67

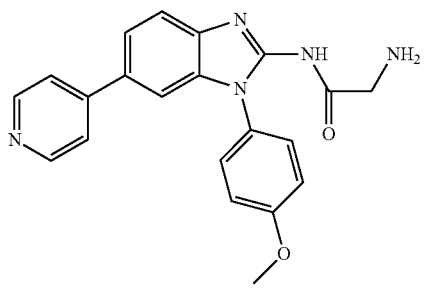

67

$^1$H NMR (400 MHz, CDCl$_3$) δ 8.55-8.61 (br s, 2H), 7.30-7.55 (3×m, 7H), 7.02-7.21 (2×m, 4H), 5.25 (br s, 2H), 3.89 (s, 3H). $^{13}$C NMR (100 MHz, CDCl$_3$) δ171.42, 160.22, 154.15, 150.05, 148.87, 135.89, 130.58, 128.44, 128.35, 126.28, 121.50, 121.46, 121.43, 121.16, 116.72, 116.37, 115.84, 106.89, 55.68, 46.04, 29.71. [M+H]$^+$=374.0.

6-(4-pyridinyl)imidazo[1,2-a]pyridine, 68

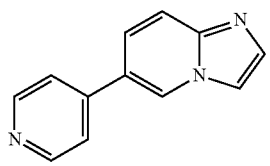

68

6-bromoimidazo[1,2-a]pyridine (7.61 mmol, 1.5 g), pyridine-4-boronic acid (1.0 eq., 7.61 mmol, 985 mg), Na$_2$CO$_3$ (4.0 eq., 30.5 mmol, 3.23 g), and a mixture of 4:1 DMF/water (80 mL) were added to a microwave vial. The vial was purged with Ar(g) then tris(dibenzylideneacetone)dipalladium (0) (Pd$_2$(dba)$_3$, 0.01 eq., 0.076 mmol, 72.0 mg) and tricyclohexylphosphine (0.03 eq., 0.228 mmol, 66.0 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via flash chromatography eluting with a CH$_2$Cl$_2$/MeOH gradient to obtain 68 (6.8 mmol, 1.326 g). Yield: 89%, light brown solid. $^1$H NMR (400 MHz, DMSO-d6) δ 9.15 (s, 1H), 8.66 (dd, J=4.5, 1.6 Hz, 2H), 7.99 (s, 1H), 7.74 (dd, J=4.5, 1.6 Hz, 2H), 7.73-7.68 (m, 3H). $^{13}$C NMR (100 MHz, DMSO-d6) δ 150.31, 144.11, 143.92, 134.14, 125.60, 123.38, 122.01, 120.81, 117.19, 113.98; [M+H]$^+$=196.0.

Intermediate: 3-iodo-6-(4-pyridinyl)imidazo[1,2-a]pyridine

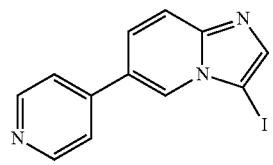 [SMILES: Ic1cnc2ccc(-c3ccncc3)cn12]

A solution of 6-(4-pyridinyl)imidazo[1,2-a]pyridine (68, 5.63 mmol, 1.10 g) in DMF (13 mL) was prepared and N-iodosuccinamide (1.05 eq., 5.92 mmol, 1.372 g) was added. The reaction was allowed to stir at rt overnight then was evaporated in vacuo and azeotroped with toluene to remove the DMF. The crude residue was purified by flash chromatography eluting with a CH$_2$Cl$_2$/MeOH gradient followed by recrystallization from EtOH to obtain 3-iodo-6-(4-pyridinyl)imidazo[1,2-a]pyridine (5.40 mmol, 1.729 g). Yield: 96%, pale yellow solid. $^1$H NMR (400 MHz, DMSO-d6) δ 8.69 (s, 1H), 8.59 (s, 1H), 7.83 (d, J=5.8 Hz, 1H), 7.79 (d, J=11.9 Hz, 1H), 7.76-7.70 (m, 2H). $^{13}$C NMR (100 MHz, DMSO-d6) δ 150.32, 143.63, 140.90, 124.51, 124.32, 123.79, 121.41, 117.59; [M+H]$^+$=322.0.

Intermediate: 3-iodo-6-(1H-pyrazol-4-yl)imidazo[1,2-a]pyridine

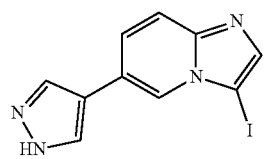 [SMILES: Ic1cnc2ccc(-c3cn[nH]c3)cn12]

A solution of 6-(1H-pyrazol-4-yl)imidazo[1,2-a]pyridine (2.71 mmol, 500 mg) in DMF (11 mL) was prepared and N-iodosuccinamide (1.05 eq., 2.85 mmol, 661 mg) was added. The reaction was allowed to stir at rt overnight then was evaporated in vacuo and azeotroped with toluene to remove the DMF. The crude residue was purified by flash chromatography eluting with a CH$_2$Cl$_2$/MeOH gradient to obtain 3-iodo-6-(1H-pyrazol-4-yl)imidazo[1,2-a]pyridine (1.56 mmol, 484.2 mg). Yield: 58%, yellow solid. ¹H NMR (400 MHz, DMSO-d6) δ 13.08 (br. s, 1H), 8.39 (t, J=1.3 Hz, 1H), 8.20 (br. s, 2H), 7.71-7.65 (m, 1H), 7.65-7.58 (m, 2H). ¹³C NMR (100 MHz, DMSO-d6) δ 145.92, 140.02, 124.87, 120.65, 119.72, 117.31, 117.19, 64.66; [M+H]⁺=311.0.

3-(3,4-methylenedioxyphenyl)-6-(4-pyridinyl)imidazo[1,2-a]pyridine, 69

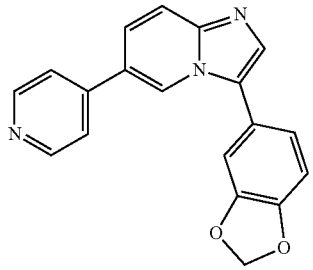

69

3-iodo-6-(4-pyridinyl)imidazo[1,2-a]pyridine (0.235 mmol, 75 mg), 3,4-methylenedioxyphenyl boronic acid (1.0 eq., 0.235 mmol, 39 mg), Na₂CO₃ (4.0 eq., 0.940 mmol, 100 mg), and a mixture of 4:1 DMF/water (2.5 mL) were added to a microwave vial. The vial was purged with Ar(g) then tris(dibenzylideneacetone)dipalladium (0) (Pd₂(dba)₃, 0.01 eq., 2.4 μmol, 2.3 mg) and tricyclohexylphosphine (0.03 eq., 7.1 μmol, 2.1 mg) was added. The reaction was microwave irradiated under Ar (g) at 130° C. for 30 min. then filtered through celite washing down with CH₂Cl₂ and MeOH. The filtrate was evaporated in vacuo and DMF was removed by azeotroping with toluene. The crude material was purified via flash chromatography eluting with a CH₂Cl₂/MeOH gradient to obtain 69 (0.121 mmol, 38 mg). Yield: 51%, yellow oil, ¹H NMR (400 MHz, DMSO-d6) δ 8.74 (s, 1H), 8.65 (d, J=4.7 Hz, 2H), 7.81-7.73 (m, 4H), 7.70 (dd, J=9.4, 1.7 Hz, 1H), 7.36 (d, J=1.7 Hz, 1H), 7.22 (dd, J=8.0, 1.6 Hz, 1H), 7.10 (d, J=8.0 Hz, 1H), 6.12 (s, 2H). ¹³C NMR (100 MHz, DMSO-d6) δ 150.23, 148.06, 147.35, 144.74, 144.15, 133.15, 125.97, 123.62, 122.98, 122.34, 122.14, 122.01, 121.35, 117.80, 109.15, 108.51, 101.39; [M+H]⁺=316.0.

6-(1H-pyrazol-4-yl)imidazo[1,2-a]pyridine, 70

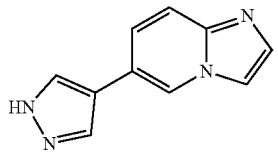

70

6-bromoimidazo[1,2-a]pyridine (4.06 mmol, 800 mg), 1H-pyrazol-4-yl boronic acid pinacol ester (1.0 eq., 4.06 mmol, 829 mg), Na₂CO₃ (4.0 eq., 16.2 mmol, 1.72 g), and a mixture of 4:1 DMF/water (40 mL) were added to a microwave vial. The vial was purged with Ar(g) then tris (dibenzylideneacetone)dipalladium (0) (Pd₂(dba)₃, 0.01 eq., 0.041 mmol, 38.3 mg) and tricyclohexylphosphine (0.03 eq., 0.122 mmol, 35.2 mg) was added. The reaction was microwave irradiated under Ar (g) at 130° C. for 30 min. then filtered through celite washing down with CH₂Cl₂ and MeOH. The filtrate was evaporated in vacuo and DMF was removed by azeotroping with toluene. The crude material was purified via flash chromatography eluting with a CH₂Cl₂/MeOH gradient to obtain 70 (3.61 mmol, 665 mg). Yield: 89%, light brown solid. ¹H NMR (400 MHz, DMSO-d6) δ 8.91 (t, J=1.3 Hz, 1H), 8.10 (br. s, 2H), 7.91 (s, 1H), 7.64-7.54 (m, 3H). 13C NMR (100 MHz, DMSO-d6) δ 143.14, 132.56, 124.77, 121.82, 118.42, 117.45, 116.59, 113.27; [M+H]⁺=185.0.

3-(4-methoxyphenyl)-6-(4-pyridinyl)imidazo[1,2-a]pyridine, 71

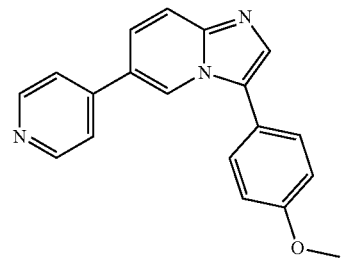 [SMILES: COc1ccc(-c2cnc3ccc(-c4ccncc4)cn23)cc1]

3-iodo-6-(4-pyridinyl)imidazo[1,2-a]pyridine (0.156 mmol, 50.0 mg), 4-methoxyphenyl boronic acid (1.0 eq., 0.156 mmol, 23.7 mg), Na₂CO₃ (4.0 eq., 0.623 mmol, 66.0 mg), and a mixture of 4:1 DMF/water (2 mL) were added to a microwave vial. The vial was purged with Ar(g) then tris(dibenzylideneacetone)dipalladium (0) (Pd₂(dba)₃, 0.01 eq., 1.6 μmol, 1.5 mg) and tricyclohexylphosphine (0.03 eq., 4.7 μmol, 1.4 mg) was added. The reaction was microwave irradiated under Ar (g) at 130° C. for 30 min. then filtered through celite washing down with CH₂Cl₂ and MeOH. The filtrate was evaporated in vacuo and DMF was removed by azeotroping with toluene. The crude material was purified via reverse phase preparative LCMS eluting with a water/acetonitrile gradient to obtain 71 (0.042 mmol, 12.6 mg). Yield: 27%, yellow solid. 1H NMR (400 MHz, DMSO-d6) δ 8.85-8.56 (m, 3H), 7.90-7.70 (m, 4H), 7.69 (d, J=8.8 Hz, 2H), 7.14 (d, J=8.8 Hz, 2H), 3.84 (s, 3H). 13C NMR (100 MHz, DMSO-d6) δ 159.26, 150.22, 144.11, 132.76, 129.47, 123.60, 123.06, 122.18, 121.41, 120.72, 117.84, 114.84, 55.29; [M+H]⁺=302.0.

3-(4-methylsulfonylphenyl)-6-(4-pyridinyl)imidazo[1,2-a]pyridine, 72

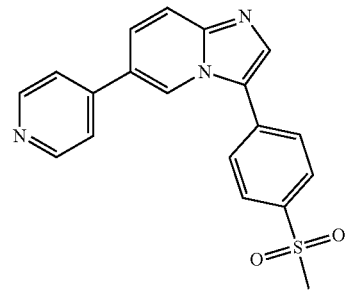

3-iodo-6-(4-pyridinyl)imidazo[1,2-a]pyridine (0.156 mmol, 50.0 mg), 4-(methylsufonyl)phenyl boronic acid (1.0 eq., 0.156 mmol, 32.1 mg), Na$_2$CO$_3$ (4.0 eq., 0.623 mmol, 66.0 mg), and a mixture of 4:1 DMF/water (2 mL) were added to a microwave vial. The vial was purged with Ar(g) then tris(dibenzylideneacetone)dipalladium (0) (Pd$_2$(dba)$_3$, 0.01 eq., 1.6 µmol, 1.5 mg) and tricyclohexylphosphine (0.03 eq., 4.7 µmol, 1.4 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via reverse phase preparative LCMS eluting with a water/acetonitrile gradient to obtain 72 (0.0.54 mmol, 19.0 mg). Yield: 35%, yellow oil. $^1$H NMR (400 MHz, DMSO-d6) δ 9.13 (s, 1H), 8.81 (d, J=4.2 Hz, 2H), 8.26 (s, 1H), 8.14-8.06 (m, 7H), 8.02 (d, J=9.5 Hz, 1H), 3.31 (s, 3H). $^{13}$C NMR (100 MHz, DMSO-d6) δ 147.45, 146.56, 143.88, 140.42, 132.38, 131.30, 128.71, 128.02, 127.41, 125.42, 124.71, 124.11, 122.64, 116.48, 43.48; [M+H]$^+$=350.0.

3-(4-cyanophenyl)-6-(4-pyridinyl)imidazo[1,2-a]pyridine, 73

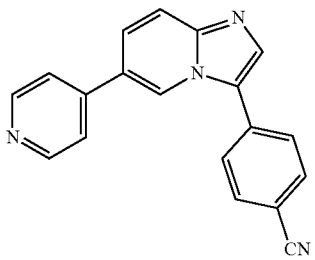

73

3-iodo-6-(4-pyridinyl)imidazo[1,2-a]pyridine (0.156 mmol, 50.0 mg), 4-cyanophenyl boronic acid (1.0 eq., 0.156 mmol, 23.4 mg), Na$_2$CO$_3$ (4.0 eq., 0.623 mmol, 66.0 mg), and a mixture of 4:1 DMF/water (2 mL) were added to a microwave vial. The vial was purged with Ar(g) then tris (dibenzylideneacetone)dipalladium (0) (Pd$_2$(dba)$_3$, 0.01 eq., 1.6 µmol, 1.5 mg) and tricyclohexylphosphine (0.03 eq., 4.7 mol, 1.4 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via reverse phase preparative LCMS eluting with a water/ acetonitrile gradient to obtain 73 (0.045 mmol, 13.4 mg). Yield: 29%, yellow solid. $^1$H NMR (400 MHz, DMSO-d6) δ 8.94 (dd, J=1.7, 0.8 Hz, 1H), 8.67 (dd, J=4.6, 1.6 Hz, 2H), 8.05-7.98 (m, 5H), 7.86 (dd, J=9.4, 0.8 Hz, 1H), 7.82 (dd, J=4.6, 1.6 Hz, 2H), 7.79 (dd, J=9.4, 1.7 Hz, 1H). $^{13}$C NMR (100 MHz, DMSO-d6) δ 150.24, 146.01, 143.93, 135.37, 133.38, 133.21, 127.86, 124.81, 124.70, 123.62, 122.92, 121.49, 118.83, 117.99, 109.91; [M+H]$^+$=297.0.

4-(6-(4-pyridinyl)imidazo[1,2-a]pyridin-3-yl)benzoic acid, 74

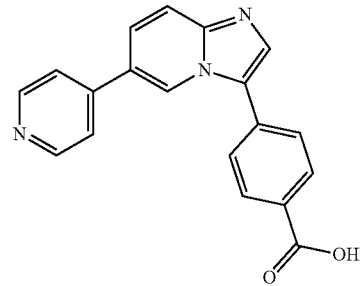

74

3-iodo-6-(4-pyridinyl)imidazo[1,2-a]pyridine (0.156 mmol, 50.0 mg), 4-boronobenzoic acid (1.0 eq., 0.156 mmol, 25.8 mg), Na$_2$CO$_3$ (4.0 eq., 0.623 mmol, 66.0 mg), and a mixture of 4:1 DMF/water (2 mL) were added to a microwave vial. The vial was purged with Ar(g) then tris (dibenzylideneacetone)dipalladium (0) (Pd$_2$(dba)$_3$, 0.01 eq., 1.6 µmol, 1.5 mg) and tricyclohexylphosphine (0.03 eq., 4.7 µmol, 1.4 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via reverse phase preparative LCMS eluting with a water/ acetonitrile gradient to obtain 74 (0.031 mmol, 9.9 mg). Yield: 20%, yellow solid. $^1$H NMR (400 MHz, DMSO-d6) δ 13.19 (br. s, 1H), 9.13 (dd, J=1.7, 0.7 Hz, 1H), 8.84 (d, J=5.9 Hz, 2H), 8.33 (s, 1H), 8.19 (dd, J=9.4, 1.7 Hz, 1H), 8.17-8.11 (m, 4H), 8.08 (dd, J=9.4, 0.7 Hz, 1H), 7.97 (d, J=8.6 Hz, 2H). $^{13}$C NMR (100 MHz, DMSO-d6) δ 166.84, 147.08, 146.73, 142.66, 130.99, 130.89, 130.29, 128.67, 128.44, 126.31, 125.06, 124.67, 122.88, 115.66; [M+H]$^+$=316.0.

4-(6-(pyridin-4-yl)imidazo[1,2-a]pyridin-3-yl)benzamide, 75

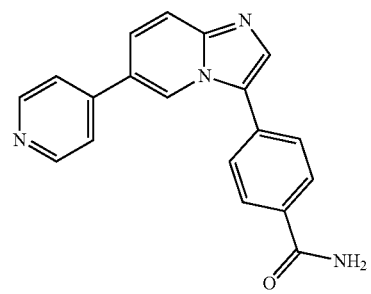

75

3-iodo-6-(4-pyridinyl)imidazo[1,2-a]pyridine (0.156 mmol, 50.0 mg), 4-carbamoylphenyl boronic acid (1.0 eq., 0.156 mmol, 26.5 mg), Na$_2$CO$_3$ (4.0 eq., 0.623 mmol, 66.0 mg), and a mixture of 4:1 DMF/water (2 mL) were added to a microwave vial. The vial was purged with Ar(g) then tris(dibenzylideneacetone)dipalladium (0) (Pd$_2$(dba)$_3$, 0.01 eq., 1.6 μmol, 1.5 mg) and tricyclohexylphosphine (0.03 eq., 4.7 μmol, 1.4 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via reverse phase preparative LCMS eluting with a water/acetonitrile gradient to obtain 75 (0.016 mmol, 5.1 mg). Yield: 10%, light orange solid. $^1$H NMR (400 MHz, DMSO-d6) δ 8.99 (br. s, 1H), 8.68 (br. s, 1H), 8.09 (s, 1H), 8.06 (d, J=8.1 Hz, 2H), 7.98-7.72 (m, 8H), 7.45 (s, 1H). $^{13}$C NMR (100 MHz, DMSO-d6) δ 168.05, 167.29, 150.17, 135.42, 133.81, 133.39, 128.52, 127.18, 126.29, 124.14, 123.46, 109.55; [M+H]$^+$=315.0.

3-(4-methylbenzoate)-6-(4-pyridinyl)imidazo[1,2-a]pyridine, 76

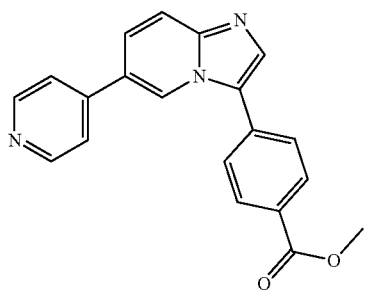

76

3-iodo-6-(4-pyridinyl)imidazo[1,2-a]pyridine (0.156 mmol, 50.0 mg), (4-methoxycarbonyl)phenyl boronic acid (1.0 eq., 0.156 mmol, 28.0 mg), Na$_2$CO$_3$ (4.0 eq., 0.623 mmol, 66.0 mg), and a mixture of 4:1 DMF/water (2 mL) were added to a microwave vial. The vial was purged with Ar(g) then tris(dibenzylideneacetone)dipalladium (0) (Pd$_2$(dba)$_3$, 0.01 eq., 1.6 μmol, 1.5 mg) and tricyclohexylphosphine (0.03 eq., 4.7 μmol, 1.4 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via reverse phase preparative LCMS eluting with a water/acetonitrile gradient to obtain 76 (0.024 mmol, 7.8 mg).

Yield: 15%, pale yellow solid. $^1$H NMR (400 MHz, DMSO-d6) δ 8.94 (s, 1H), 8.66 (br. s, 2H), 8.12 (d, J=8.6 Hz, 2H), 8.00 (s, 1H), 7.96 (d, J=8.6 Hz, 2H), 7.85 (d, J=9.4 Hz, 1H), 7.82 (d, J=5.9 Hz, 2H), 7.78 (dd, J=9.4, 1.7 Hz, 1H), 3.90 (s, 3H). $^{13}$C NMR (100 MHz, DMSO-d6) δ165.89, 150.25, 143.94, 134.87, 133.32, 130.17, 128.49, 127.38, 125.17, 124.54, 123.54, 122.71, 121.45, 118.03, 52.28; [M+H]$^+$=330.0.

3-(2,3-dihydrobenzofuran-5-yl)-6-(pyridin-4-yl)imidazo[1,2-a]pyridine, 77

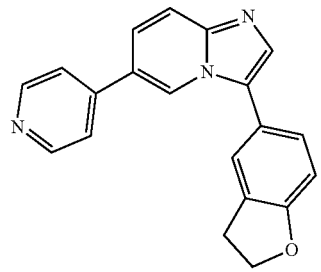

77

3-Iodo-6-(4-pyridinyl)imidazo[1,2-a]pyridine (0.156 mmol, 50.0 mg), (2,3-dihydrobenzofuran-5-yl) boronic acid (1.0 eq., 0.156 mmol, 25.5 mg), Na$_2$CO$_3$ (4.0 eq., 0.623 mmol, 66.0 mg), and a mixture of 4:1 DMF/water (2 mL) were added to a microwave vial. The vial was purged with Ar(g) then tris(dibenzylideneacetone)dipalladium (0) (Pd$_2$(dba)$_3$, 0.01 eq., 1.6 μmol, 1.5 mg) and tricyclohexylphosphine (0.03 eq., 4.7 μmol, 1.4 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via reverse phase preparative LCMS eluting with a water/acetonitrile gradient to obtain 77 (0.050 mmol, 15.8 mg). Yield: 32%, pale yellow solid. $^1$H NMR (400 MHz, DMSO-d6) δ 8.72 (s, 1H), 8.64 (s, 2H), 7.81-7.74 (m, 3H), 7.71 (s, 1H), 7.69 (dd, J=9.4, 1.7 Hz, 1H), 7.59 (s, 1H), 7.46 (dd, J=8.2, 1.9 Hz, 1H), 6.95 (d, J=8.2 Hz, 1H), 4.61 (t, J=8.7 Hz, 2H), 3.28 (t, J=8.7 Hz, 2H). $^{13}$C NMR (100 MHz, DMSO-d6) δ 159.91, 150.24, 144.17, 132.75, 128.71, 128.16, 125.18, 123.37, 122.94, 122.08, 121.35, 120.47, 117.87, 109.68, 71.33, 29.09; [M+H]$^+$=314.0.

3-(3,4-methylenedioxyphenyl)-6-(1H-pyrazol-4-yl)imidazo[1,2-a]pyridine, 78

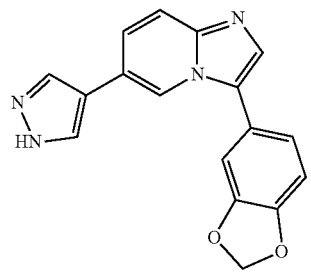

78

3-iodo-6-(1H-pyrazol-4-yl)imidazo[1,2-a]pyridine (0.156 mmol, 50.0 mg), 3,4-methylenedioxyphenyl boronic acid (1.0 eq., 0.156 mmol, 26.8 mg), Na$_2$CO$_3$ (4.0 eq., 0.623 mmol, 66.0 mg), and a mixture of 4:1 DMF/water (2 mL) were added to a microwave vial. The vial was purged with Ar(g) then tris(dibenzylideneacetone)dipalladium (0) (Pd$_2$(dba)$_3$, 0.01 eq., 1.6 μmol, 1.5 mg) and tricyclohexylphosphine (0.03 eq., 4.7 μmol, 1.4 mg) was added. The reaction was microwave irradiated under Ar (g) at 130° C. for 30 min.

then filtered through celite washing down with CH$_2$Cl$_2$ and MeOH. The filtrate was evaporated in vacuo and DMF was removed by azeotroping with toluene. The crude material was purified via reverse phase preparative LCMS eluting with a water/acetonitrile gradient to obtain 78 (0.048 mmol, 14.5 mg).

Yield: 30%, white solid. $^1$H NMR (400 MHz, DMSO-d6) δ 8.55 (s, 1H), 8.37 (br. s, 1H), 8.12 (br. s, 2H), 7.69-7.62 (m, 2H), 7.56 (dd, J=9.3, 1.6 Hz, 1H), 7.27 (d, J=1.6 Hz, 1H), 7.17 (dd, J=8.0, 1.7 Hz, 1H), 7.10 (d, J=8.0 Hz, 1H), 6.12 (s, 2H). $^{13}$C NMR (100 MHz, DMSO-d6) δ 148.02, 147.15, 144.19, 132.49, 125.17, 124.26, 122.54, 121.73, 118.90, 118.37, 117.58, 109.12, 108.44, 101.33; [M+H]$^+$=305.0.

4-(6-(1H-pyrazol-4-yl)imidazo[1,2-a]pyridin-3-yl)benzoic acid, 79

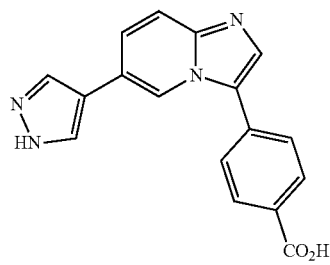

3-iodo-6-(1H-pyrazol-4-yl)imidazo[1,2-a]pyridine (0.156 mmol, 50.0 mg), 4-boronobenzoic acid (1.0 eq., 0.156 mmol, 26.8 mg), Na$_2$CO$_3$ (4.0 eq., 0.623 mmol, 66.0 mg), and a mixture of 4:1 DMF/water (2 mL) were added to a microwave vial. The vial was purged with Ar(g) then tris (dibenzylideneacetone)dipalladium (0) (Pd$_2$(dba)$_3$, 0.01 eq., 1.6 μmol, 1.5 mg) and tricyclohexylphosphine (0.03 eq., 4.7 μmol, 1.4 mg) was added. The reaction was microwave irradiated under Ar (g) at 130° C. for 30 min. then filtered through celite washing down with CH$_2$Cl$_2$ and MeOH. The filtrate was evaporated in vacuo and DMF was removed by azeotroping with toluene. The crude material was purified via reverse phase preparative LCMS eluting with a water/acetonitrile gradient to obtain 79 (0.001 mmol, 1.7 mg). Yield: 4%, pale yellow solid. $^1$H NMR (400 MHz, DMSO-d6) δ 8.74 (s, 1H), 8.17 (br. s, 1H), 8.10 (d, J=8.4 Hz, 2H), 7.91-7.82 (m, 4H), 7.72 (d, J=9.3 Hz, 1H), 7.64 (dd, J=9.3, 1.6 Hz, 1H). $^{13}$C NMR (100 MHz, DMSO-d6) δ 145.55, 134.45, 134.34, 130.71, 128.49, 127.34, 125.38, 125.12, 119.90, 119.04, 118.21, 117.88; [M+H]$^+$=305.0.

Example III

This example shows DYRK1A inhibitory activity of the compounds of the present invention. [Key (+=1-40% inhibition @10 uM, ++=40-60% inhibition @10 uM, +++=60%-100% inhibition @10 uM)]$^a$.

| Generic Structure (I) | R$_1$ | R$_2$ | R$_3$ | % Inhibition$^a$ |
|---|---|---|---|---|
| 1 | 4-MeO-phenyl | 4-pyridyl | —H | +++ |
| 2 | 4-MeO-phenyl | 5-pyrimidinyl | —H | + |
| 3 | 4-MeO-phenyl | 2-Cl-3-pyridyl | —H | ++ |
| 4 | 4-MeO-phenyl | 6-NH$_2$-3-pyridyl | —H | ++ |

-continued

| # | | | | |
|---|---|---|---|---|
| 5 | 4-MeO-C6H4- | C6H5- | —H | ++ |
| 6 | —H | 4-pyridyl | —H | +++ |
| 7 | C6H5- | 4-pyridyl | —H | + |
| 8 | 4-MeO-C6H4- | —H | —H | +++ |
| 9 | 4-MeO-C6H4- | 4-pyridyl N-oxide | —H | + |
| 10 | benzo[1,3]dioxol-5-yl | 4-pyridyl | —H | +++ |
| 11 | 2,3-dihydrobenzofuran-5-yl | 4-pyridyl | —H | +++ |
| 12 | 4-(1H-tetrazol-5-yl)phenyl | 4-pyridyl | —H | +++ |
| 13 | 1H-benzimidazol-5-yl | 4-pyridyl | —H | +++ |
| 14 | 4-(MeSO2)-C6H4- | 3-MeO-C6H4- | —H | + |

-continued

| | | | | |
|---|---|---|---|---|
| 15 | 4-SO2Me-phenyl | 3,4-difluorophenyl | —H | + |
| 16 | 4-SO2Me-phenyl | pyridin-4-yl | —H | +++ |
| 17 | 4-SO2Me-phenyl | pyridin-3-yl | —H | ++ |
| 18 | 4-SO2Me-phenyl | 4-OCF3-phenyl | —H | + |
| 19 | 4-SO2Me-phenyl | benzo[1,3]dioxol-5-yl | —H | +++ |
| 20 | 4-SO2Me-phenyl | 6-morpholinopyridin-3-yl | —H | +++ |
| 21 | 4-SO2Me-phenyl | 3-chloro-4-methoxyphenyl | —H | + |
| 22 | 4-SO2Me-phenyl | furan-3-yl | —H | +++ |
| 23 | 4-CN-phenyl | pyridin-4-yl | —H | +++ |
| 24 | 4-CN-phenyl | furan-3-yl | —H | +++ |

-continued
| | | | | |
|---|---|---|---|---|
| 25 | 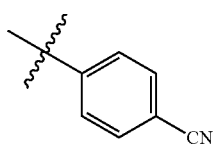 [SMILES: *c1ccc(C#N)cc1] | 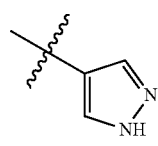 | —H | +++ |
| 26 | 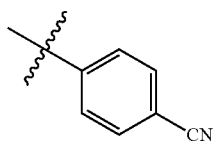 [SMILES: *c1ccc(C#N)cc1] | 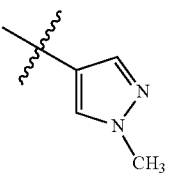 | —H | +++ |
| 27 | 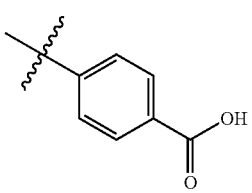 [SMILES: *c1ccc(C(=O)O)cc1] | 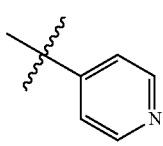 [SMILES: *c1ccncc1] | —H | +++ |
| 28 | 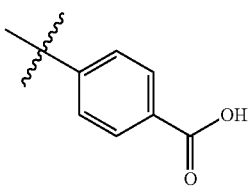 [SMILES: *c1ccc(C(=O)O)cc1] | 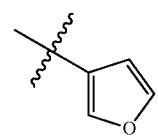 [SMILES: *c1ccoc1] | —H | +++ |
| 29 | 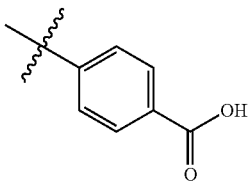 [SMILES: *c1ccc(C(=O)O)cc1] | 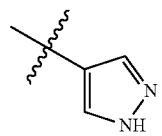 | —H | +++ |
| 30 | 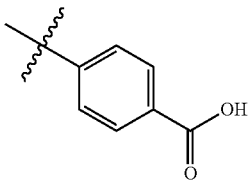 [SMILES: *c1ccc(C(=O)O)cc1] | 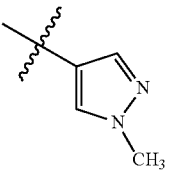 [SMILES: *c1cnn(C)c1] | —H | +++ |
| 31 | 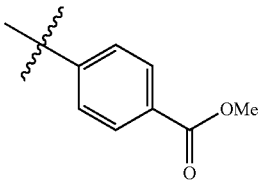 [SMILES: *c1ccc(C(=O)OC)cc1] | 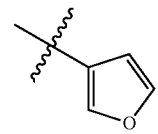 [SMILES: *c1ccoc1] | —H | +++ |
| 32 | 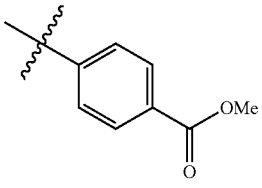 [SMILES: *c1ccc(C(=O)OC)cc1] | 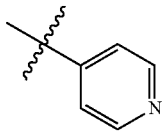 [SMILES: *c1ccncc1] | —H | +++ |

| | | | | |
|---|---|---|---|---|
| 33 | 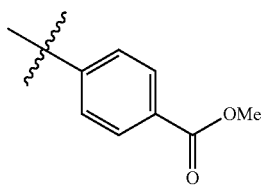 [SMILES: *c1ccc(C(=O)OC)cc1] | 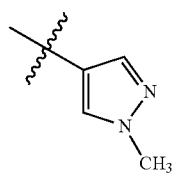 [SMILES: *c1cnn(C)c1] | —H | +++ |
| 34 | 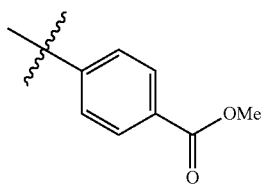 [SMILES: *c1ccc(C(=O)OC)cc1] | 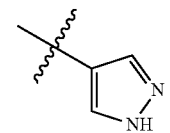 | —H | +++ |
| 35 | 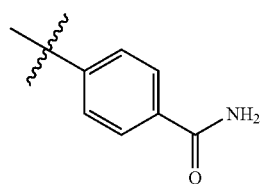 [SMILES: *c1ccc(C(N)=O)cc1] | 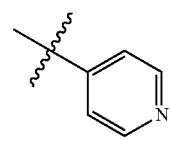 [SMILES: *c1ccncc1] | —H | +++ |
| 36 | 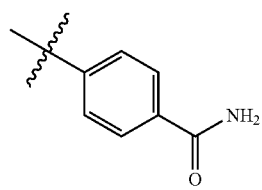 [SMILES: *c1ccc(C(N)=O)cc1] | 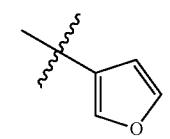 [SMILES: *c1ccoc1] | —H | +++ |
| 37 | 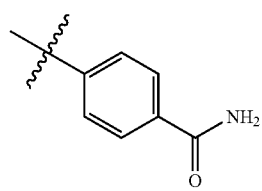 [SMILES: *c1ccc(C(N)=O)cc1] | 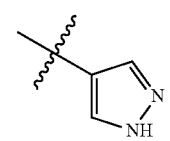 | —H | +++ |
| 38 | 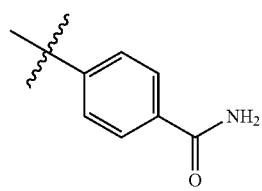 [SMILES: *c1ccc(C(N)=O)cc1] | 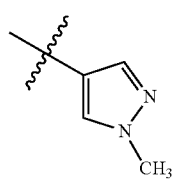 [SMILES: *c1cnn(C)c1] | —H | +++ |
| 39 | 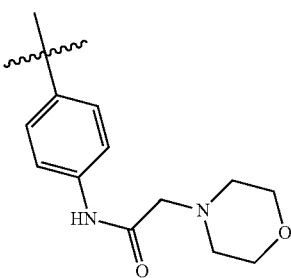 [SMILES: *c1ccc(NC(=O)CN2CCOCC2)cc1] | 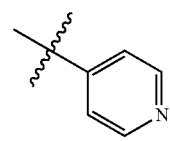 [SMILES: *c1ccncc1] | —H | +++ |

-continued
| | | | | |
|---|---|---|---|---|
| 40 | 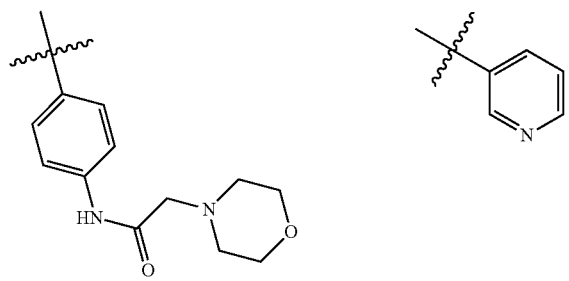 | 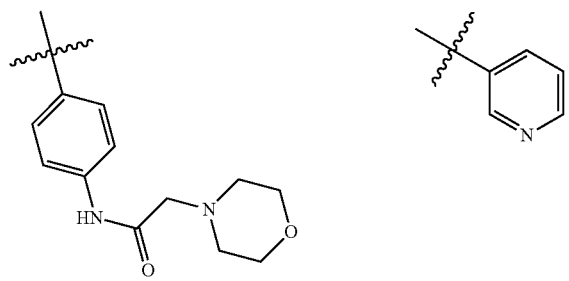 | —H | +++ |
| 41 | 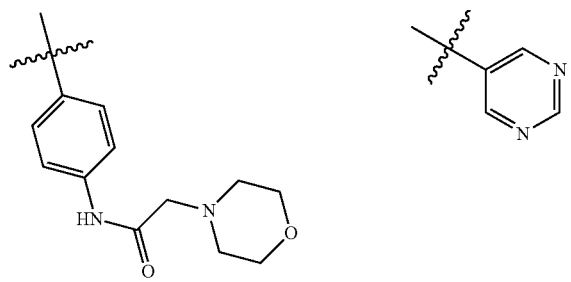 | 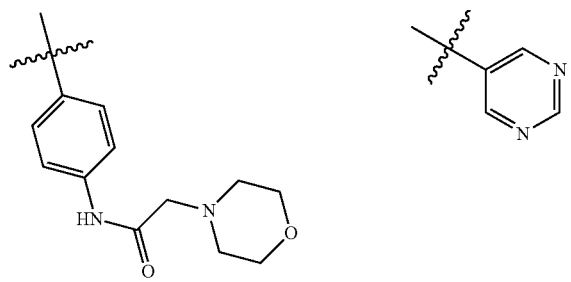 | —H | +++ |
| 42 | 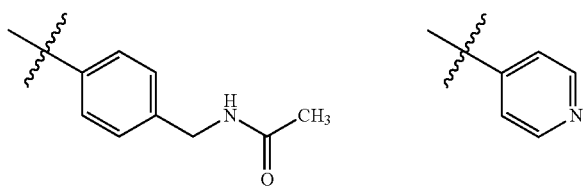 | 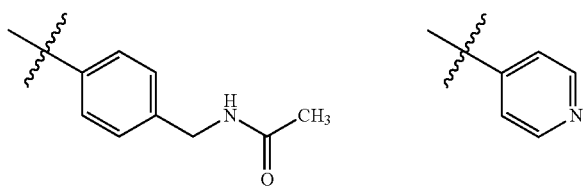 | —H | +++ |
| 43 | 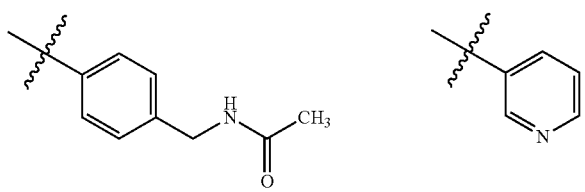 | 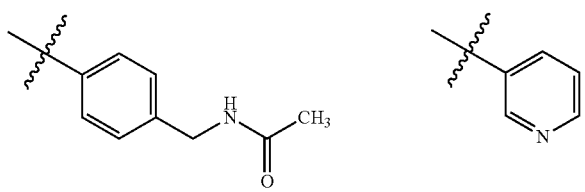 | —H | +++ |
| 44 | 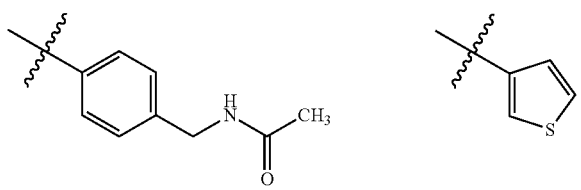 | 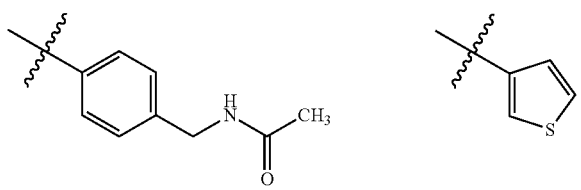 | —H | +++ |
| 45 | 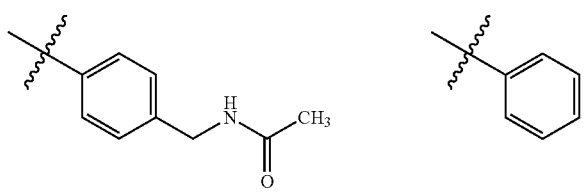 | 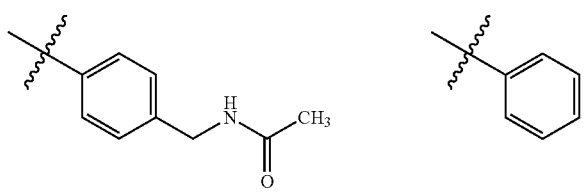 | —H | ++ |
| 46 | 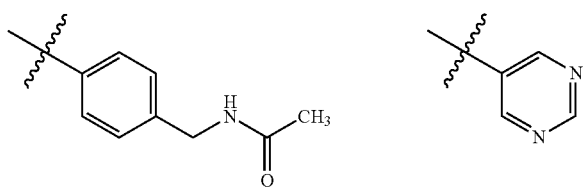 | 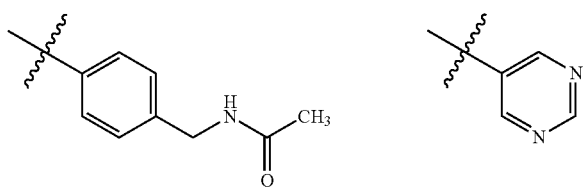 | —H | + |

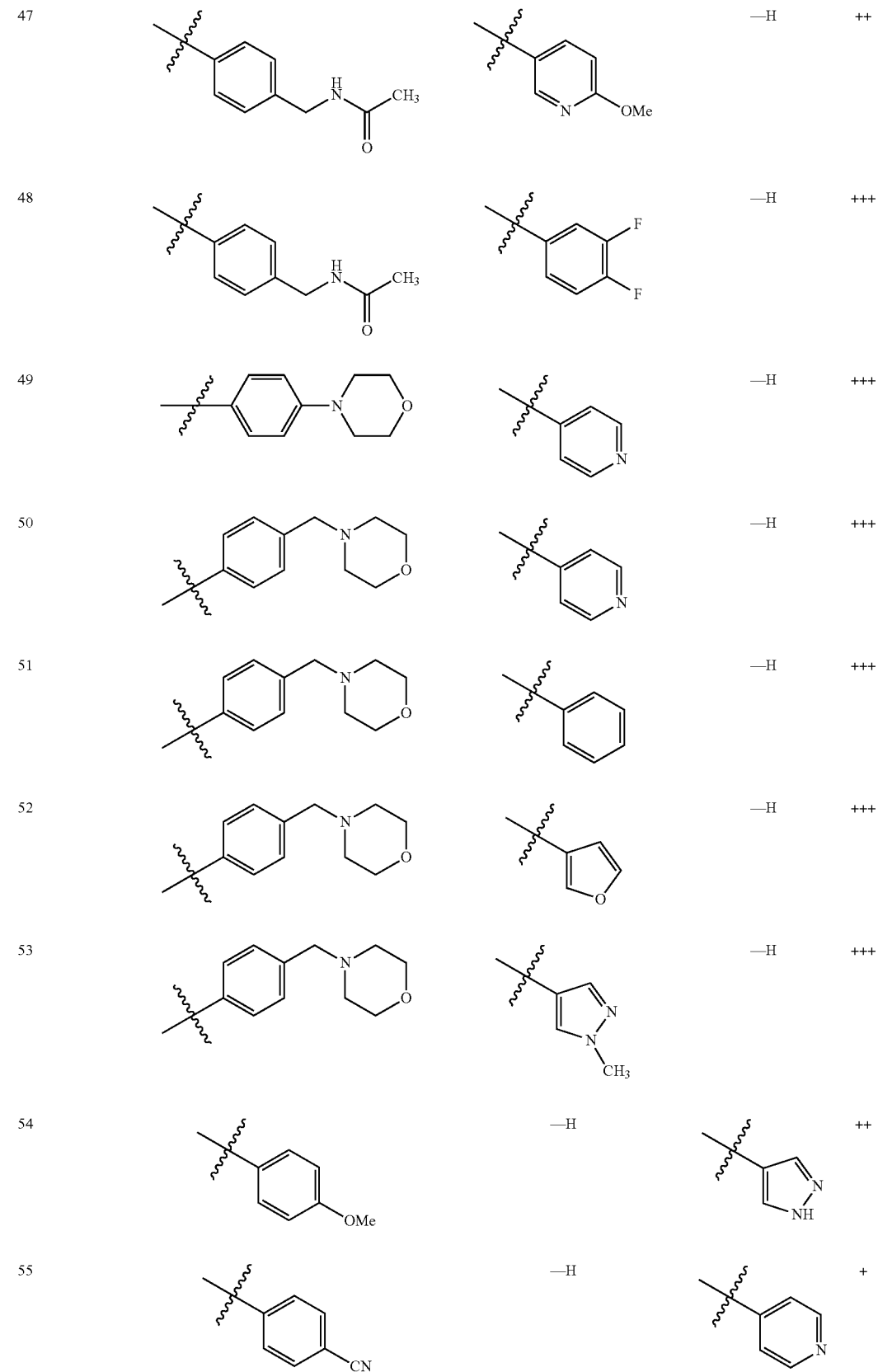

-continued

| | | | | |
|---|---|---|---|---|
| 56 | 4-carbamoylphenyl | —H | 4-pyridyl | +++ |
| 57 | 4-carboxyphenyl | —H | 4-pyridyl | +++ |
| 58 | 3,4-dimethoxyphenyl | 4-pyridyl | —H | +++ |
| 59 | 2,3-dihydrobenzo[1,4]dioxin-6-yl | 4-pyridyl | —H | +++ |
| 60 | benzo[1,3]dioxol-5-yl | 2-fluoropyridin-4-yl | —H | +++ |
| 61 | benzo[1,3]dioxol-5-yl | 2-methylpyridin-4-yl | —H | +++ |
| 62 | benzo[1,3]dioxol-5-yl | 1H-pyrazol-4-yl | —H | +++ |

Generic Structure (II): benzimidazole core with 2-NHR₁, N1-aryl(R₂,R₃), 6-(4-pyridyl)

| | R₁ | R₂ | R₃ | % Inhibition |
|---|---|---|---|---|
| 63 | —H | —OCH₃ | —H | +++ |
| 64 | —C(O)CH₃ | —OCH₃ | —H | +++ |

-continued
| | | | | |
|---|---|---|---|---|
| 65 | 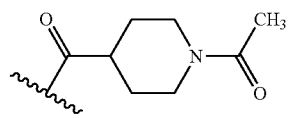 [SMILES: *C(=O)C1CCN(C(C)=O)CC1] | —OCH$_3$ | —H | +++ |
| 66 | 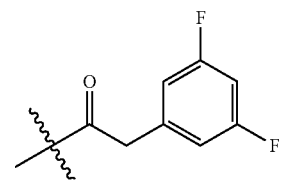 [SMILES: *C(=O)Cc1cc(F)cc(F)c1] | —OCH$_3$ | —H | + |
| 67 | 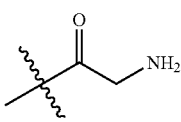 [SMILES: *C(=O)CN] | —OCH$_3$ | —H | +++ |
| | Structure | % Inhibition$^a$ |
|---|---|---|
| 68 | 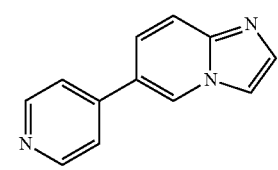 [SMILES: c1cc(-c2ccc3nccn3c2)ccn1] | +++ |
| 69 | 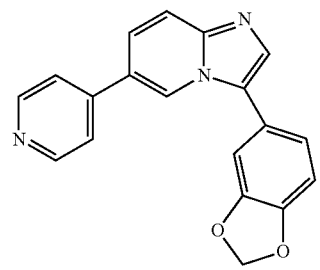 [SMILES: c1cc(-c2ccc3ncc(-c4ccc5c(c4)OCO5)n3c2)ccn1] | +++ |
| 70 | 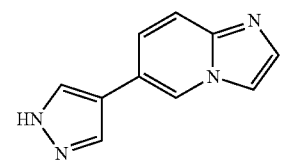 [SMILES: c1cn2cc(-c3cn[nH]c3)ccc2n1] | +++ |
| 71 | 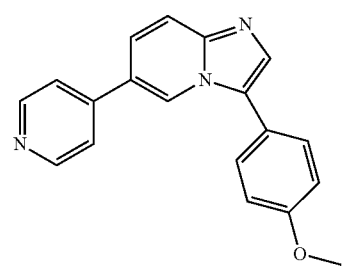 [SMILES: COc1ccc(-c2cnc3ccc(-c4ccncc4)cn23)cc1] | +++ |

-continued
| | | |
|---|---|---|
| 72 | 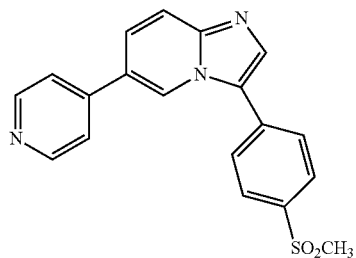 | +++ |
| 73 | 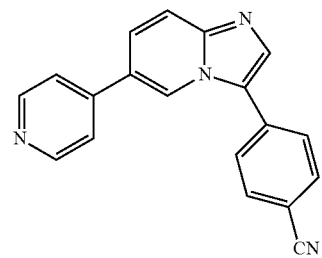 [SMILES: N#Cc1ccc(-c2cnc3ccc(-c4ccncc4)cn23)cc1] | +++ |
| 74 | 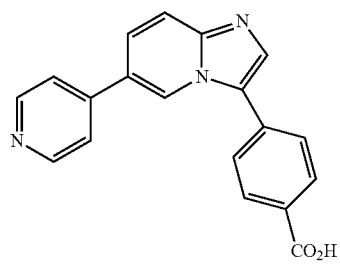 [SMILES: O=C(O)c1ccc(-c2cnc3ccc(-c4ccncc4)cn23)cc1] | +++ |
| 75 | 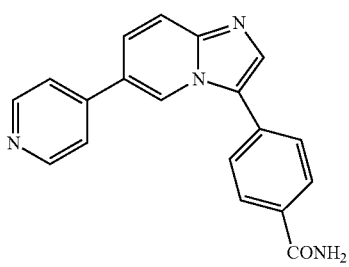 [SMILES: NC(=O)c1ccc(-c2cnc3ccc(-c4ccncc4)cn23)cc1] | +++ |
| 76 | 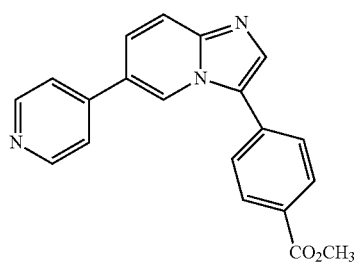 [SMILES: COC(=O)c1ccc(-c2cnc3ccc(-c4ccncc4)cn23)cc1] | +++ |
| 77 | 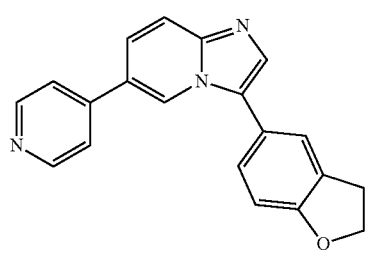 [SMILES: c1cc(-c2ccc3ncc(-c4ccc5c(c4)CCO5)n3c2)ccn1] | +++ |

| 78 | 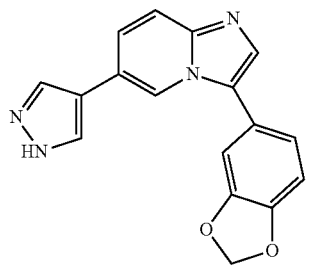 [SMILES: c1cc2ncc(-c3ccc4c(c3)OCO4)n2cc1-c1cn[nH]c1] | +++ |
|---|---|---|
| 79 | 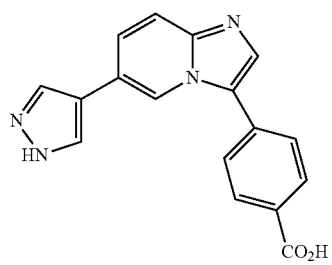 [SMILES: O=C(O)c1ccc(-c2cnc3ccc(-c4cn[nH]c4)cn23)cc1] | +++ |
Example IV
This example provides general procedures (Schemes 1, 2, and 3 (note the numbering scheme for Schemes 1, 2, and 3 is applicable only within Example IV)) for the synthesis of compounds of the present invention.
Scheme 1
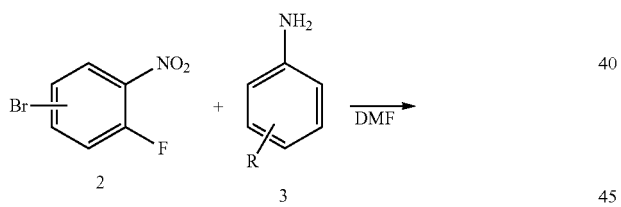
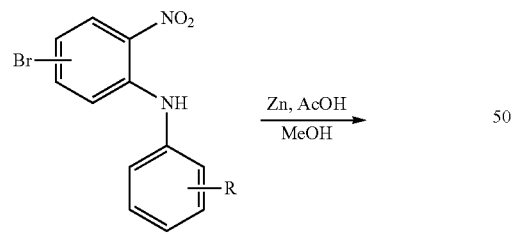
-continued
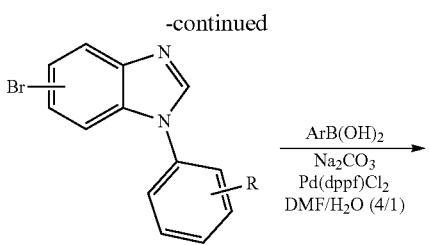
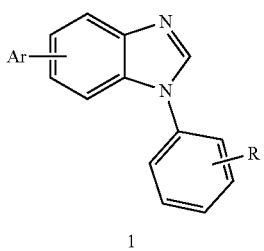
Scheme 2
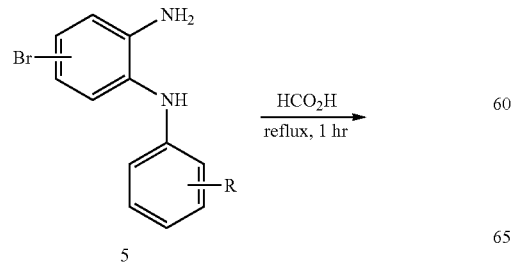
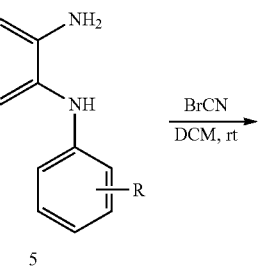

-continued

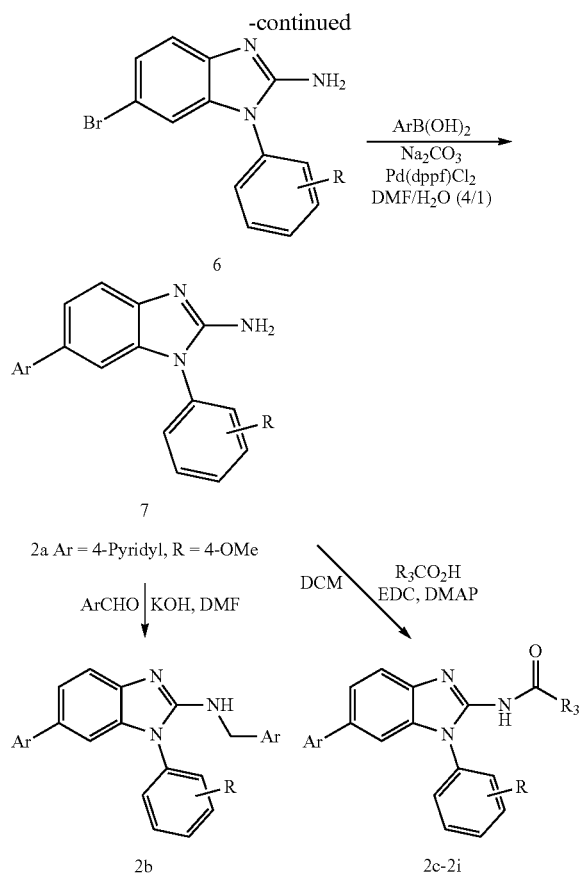

2a Ar = 4-Pyridyl, R = 4-OMe

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound having

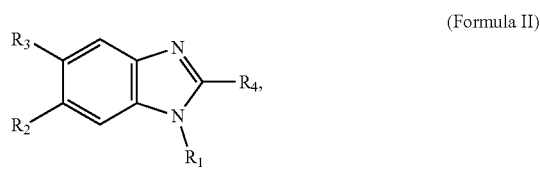
(Formula II)

pharmaceutically acceptable salts thereof, and/or solvates thereof;

wherein R1 is selected from hydrogen,

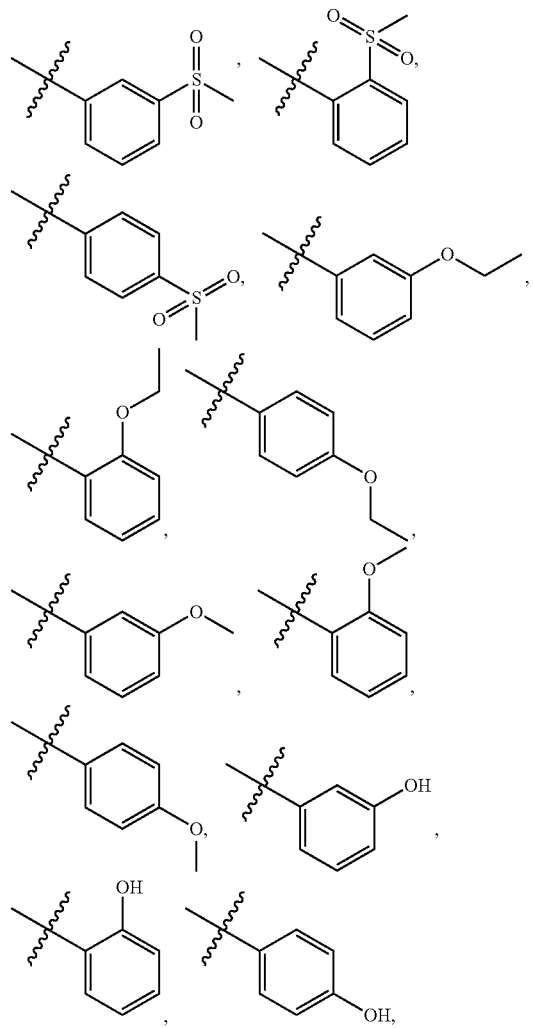

INCORPORATION BY REFERENCE

The entire disclosure of each of the patent documents and scientific articles referred to herein is incorporated by reference for all purposes. The following references are herein incorporated by reference in their entireties:

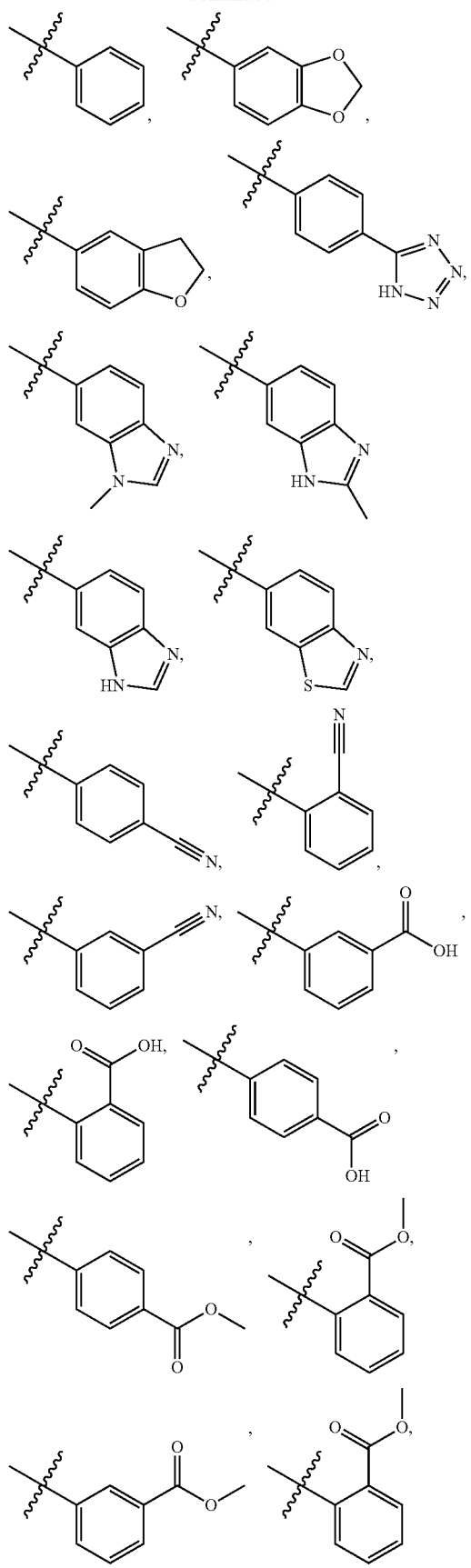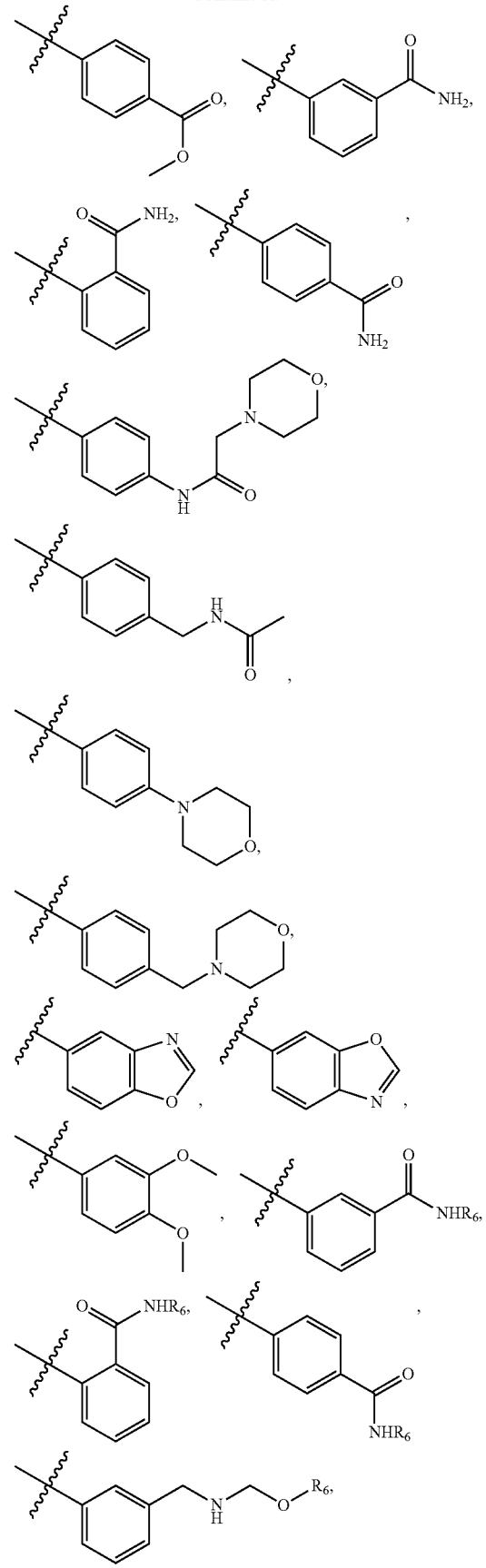

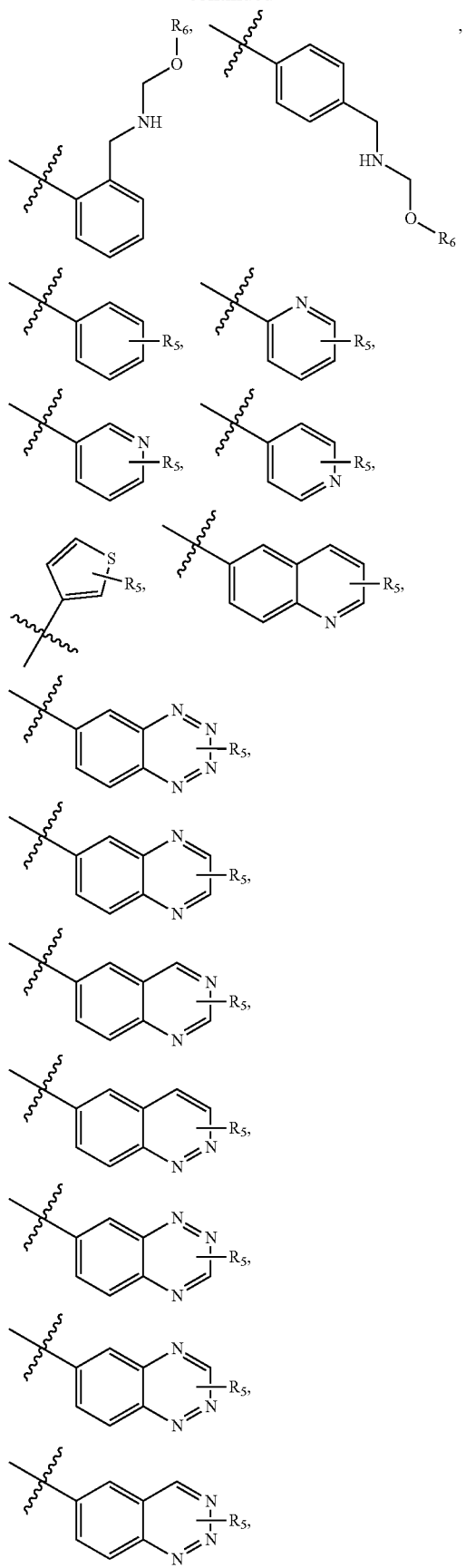
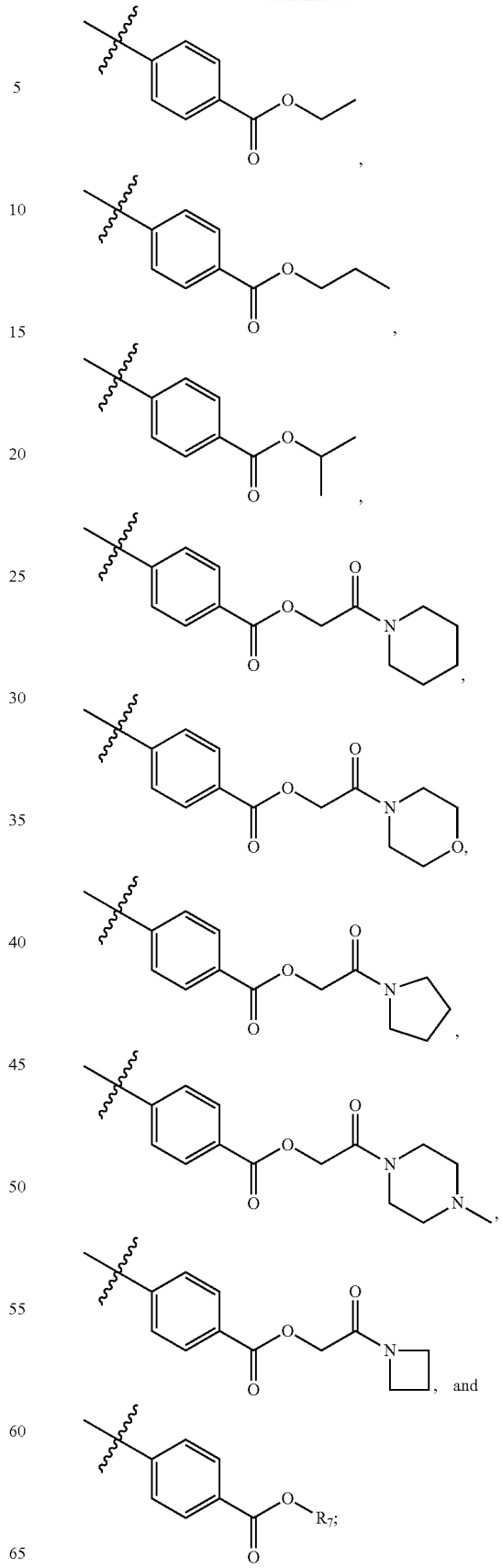

wherein each of R2 and R3 is independently selected from hydrogen,
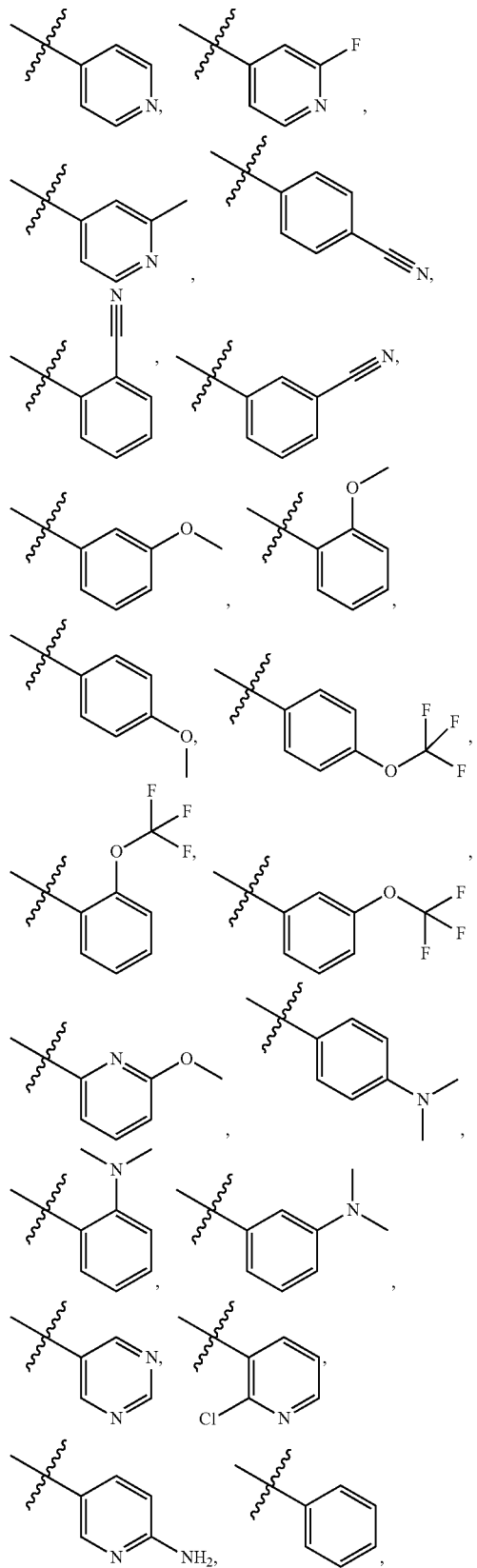
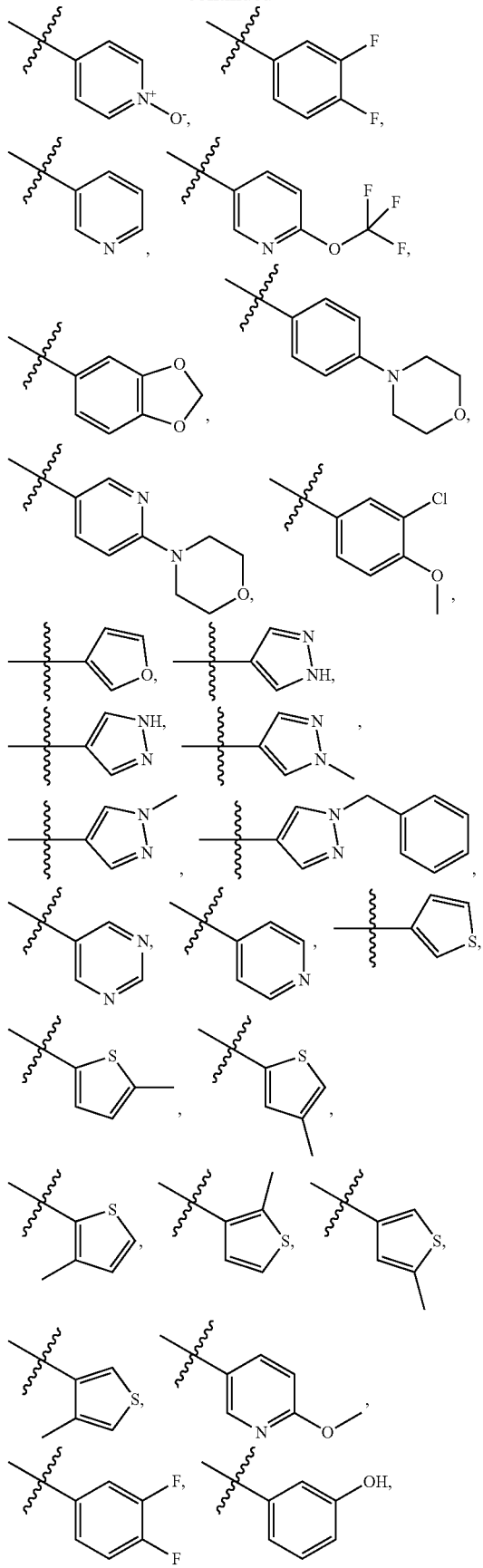

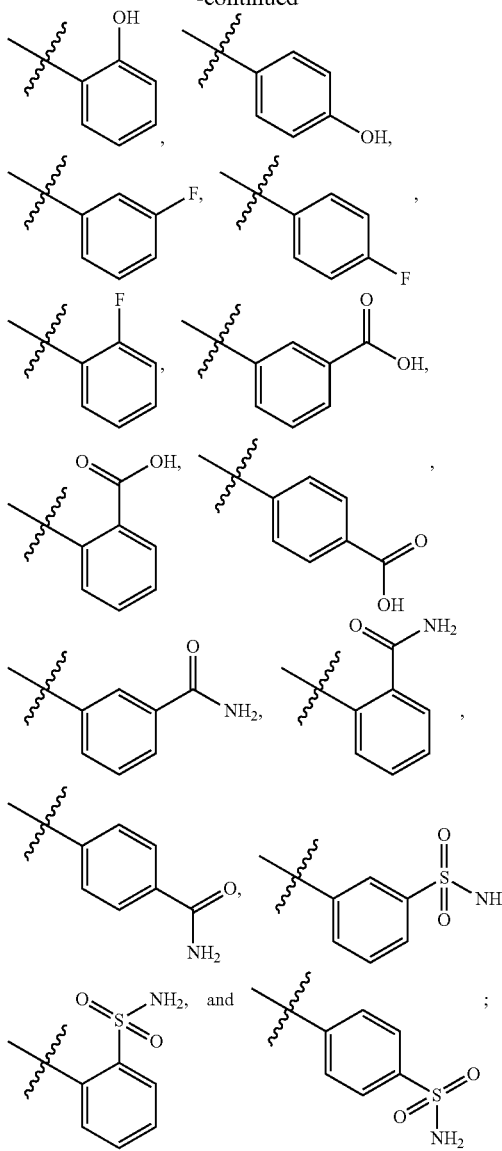
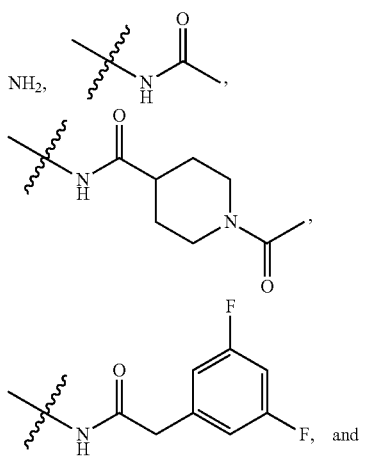
wherein R4 is selected from hydrogen,
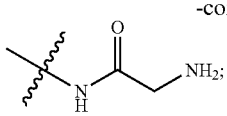
wherein R5 is selected from hydrogen, alkoxy, alkylsulfonyl, cyano, carboxy, ester, amido, substituted amido, sulfonamide, substituted sulfonamide, methylenedioxy, heterocyclyl alkyl, heterocyclyl, and heterocyclyl alkyl amido, a lipophilic moiety comprising ether functionality, methyl, ethyl, $(CH_2)_3$,
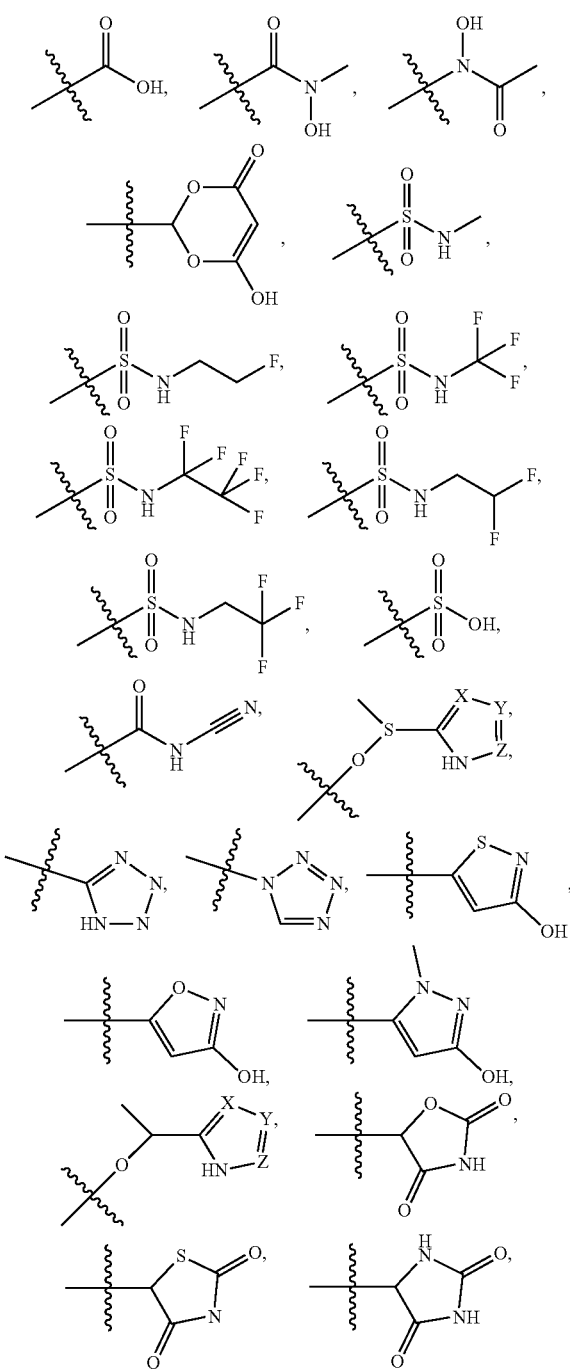

-continued wherein R6 is selected from hydrogen, C1-C4 alkyl, heterocyclyl alkyl, heteroaryl alkyl, aryl alkyl, aryl, heterocyclyl, and heteroaryl;
wherein R7 is selected from hydrogen, alkoxy, alkylsulfonyl, cyano, carboxy, ester, amido, substituted amido, sulfonamide, substituted sulfonamide, methylenedioxy, heterocyclyl alkyl, heterocyclyl, and heterocyclyl alkyl amido, a lipophilic moiety comprising ether functionality, methyl, ethyl, $(CH_2)_3$, and
wherein X, Y, Z are independently N, C or CO,
wherein R1, R2, R3, and R4 cannot each be hydrogen.

2. The compound of claim 1, wherein said compound is selected from the following compounds:

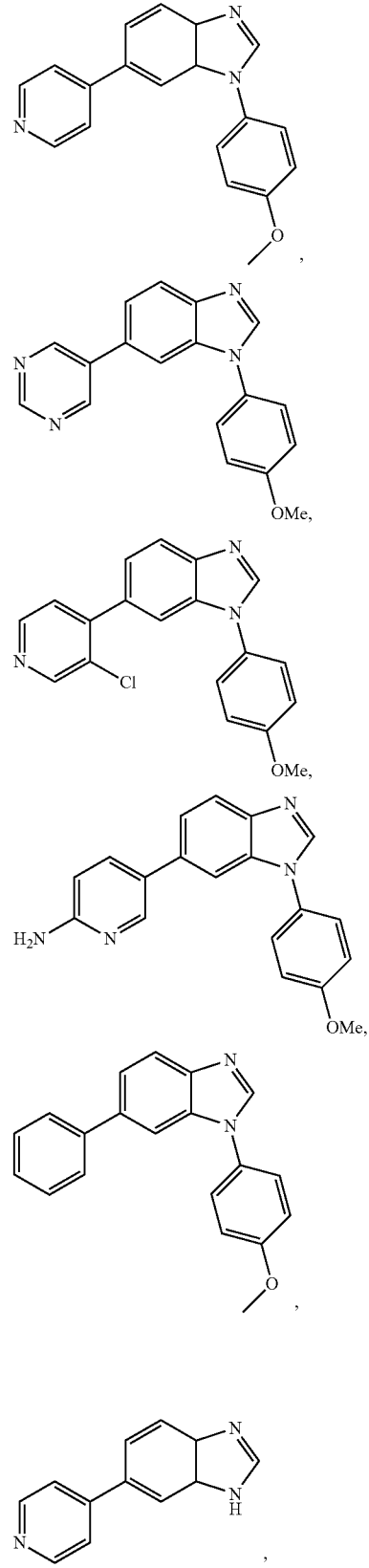

117
-continued
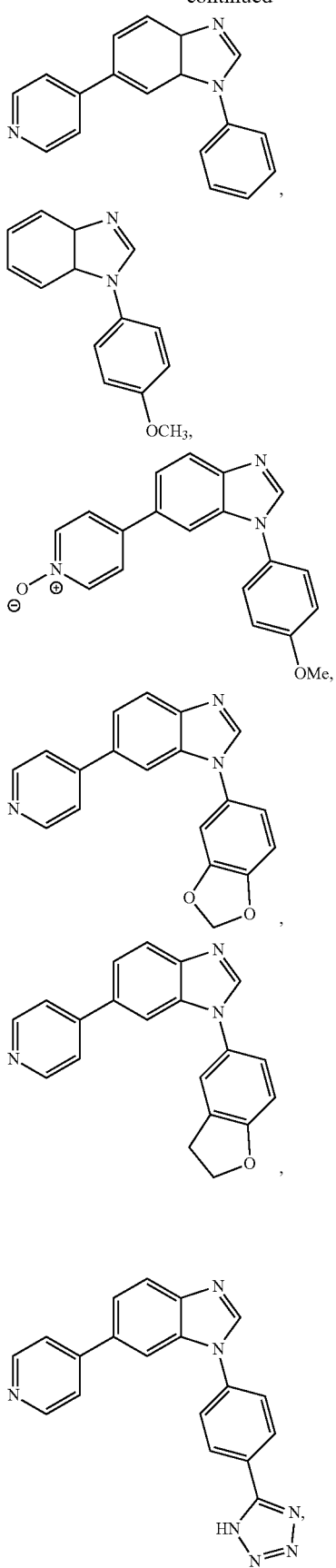
118
-continued
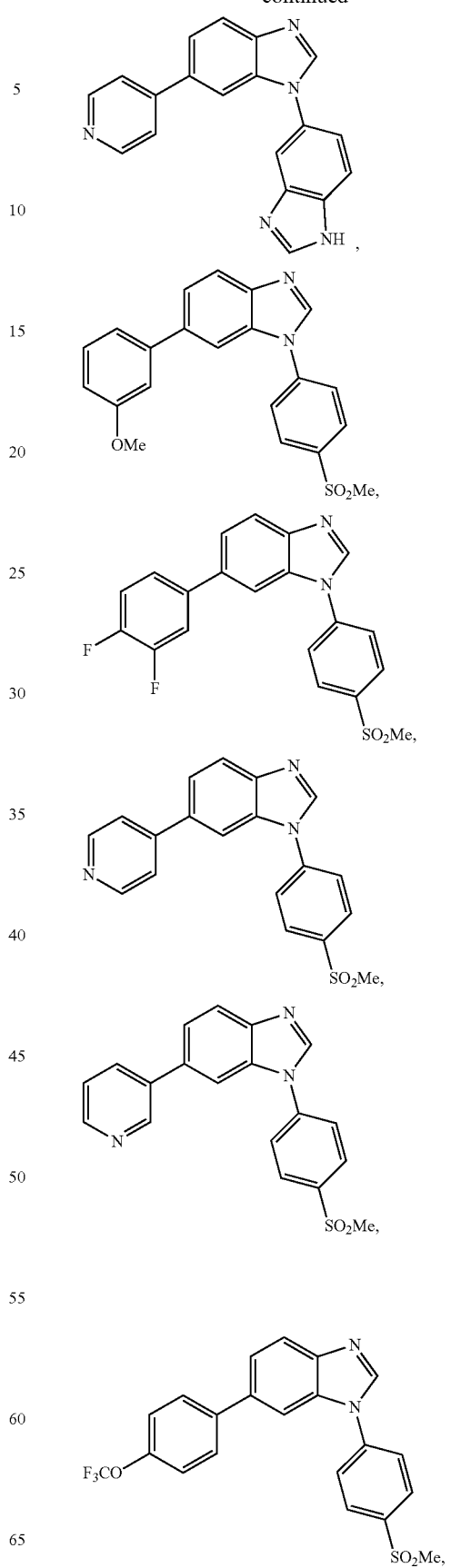

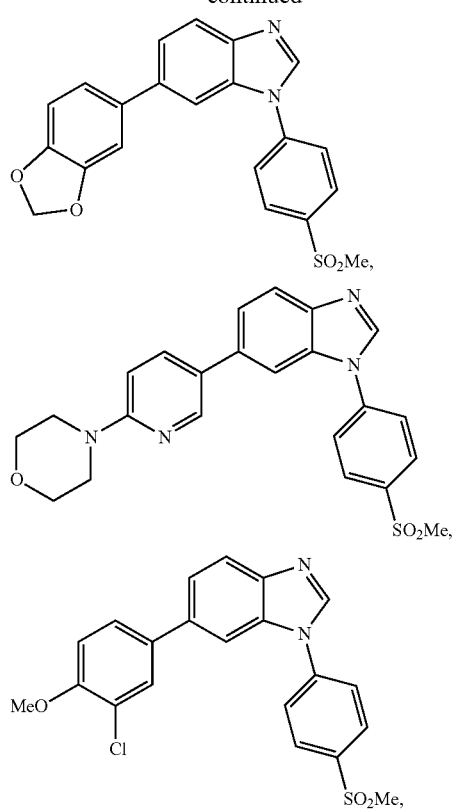
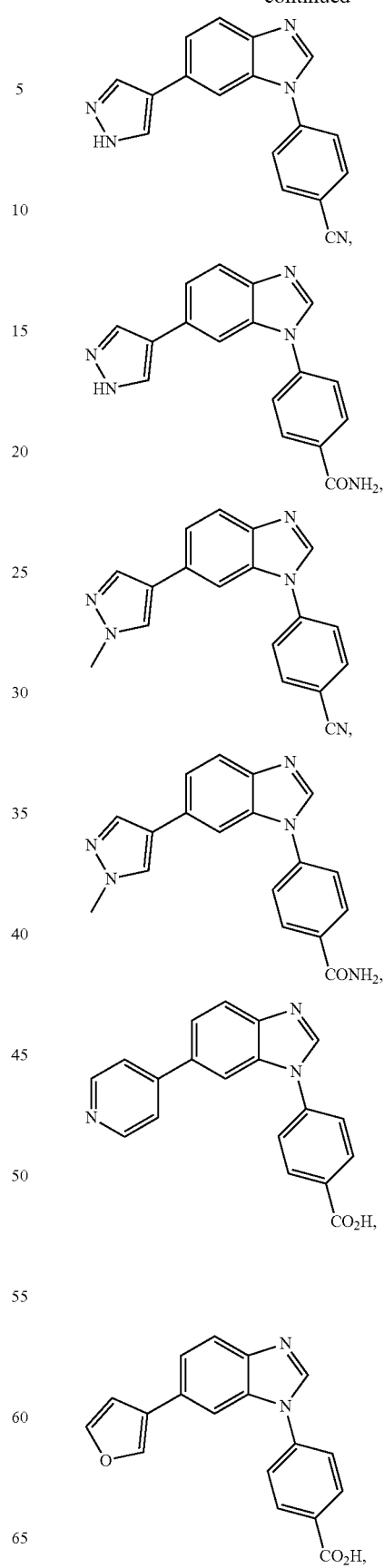

121
-continued
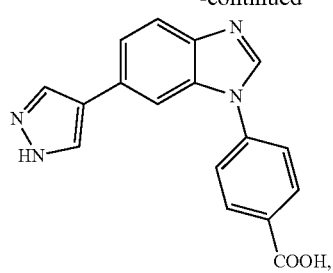
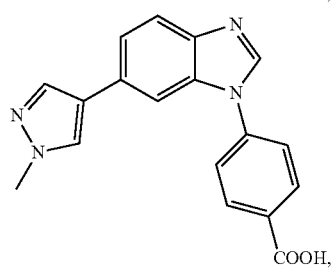
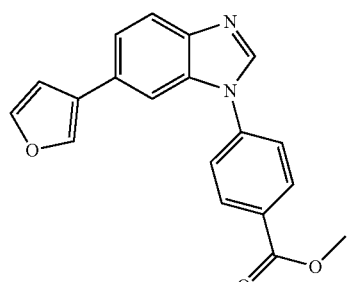
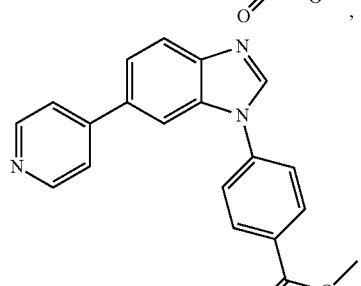
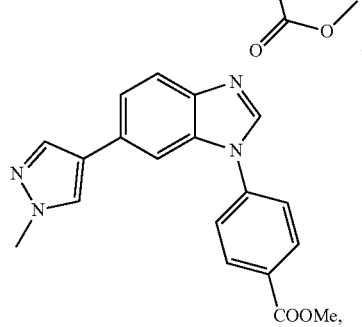
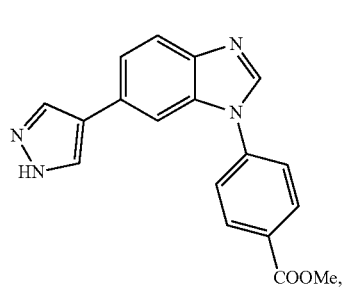
122
-continued
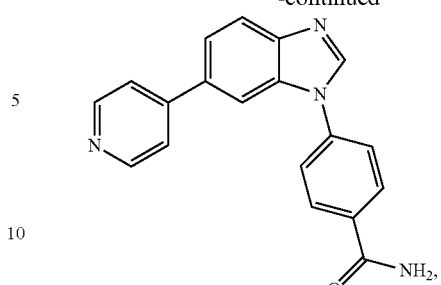
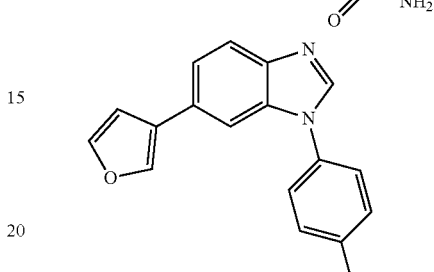
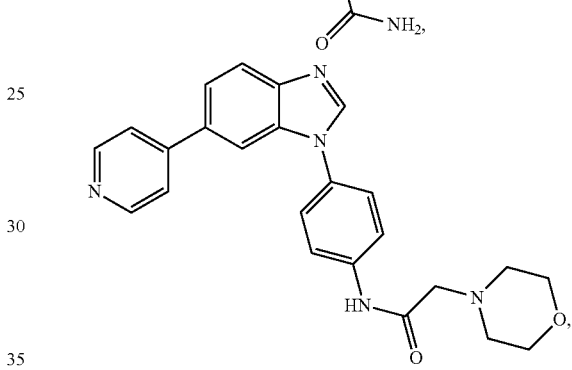
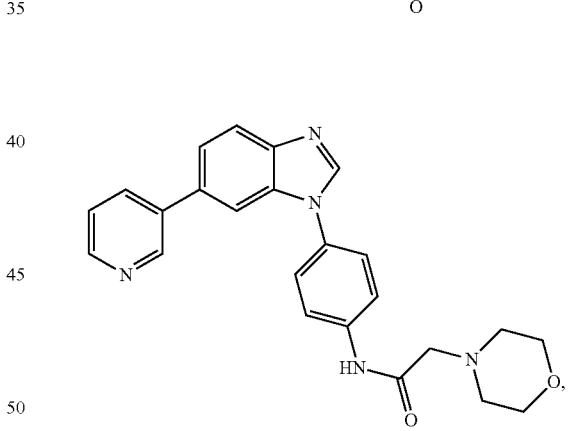
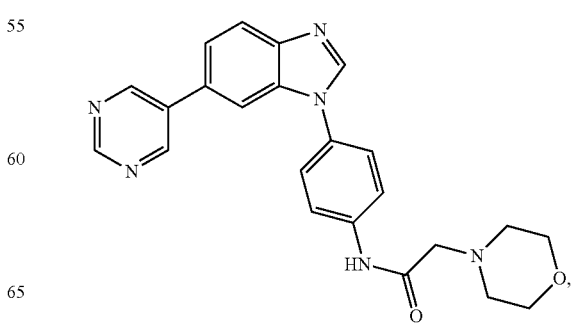

-continued
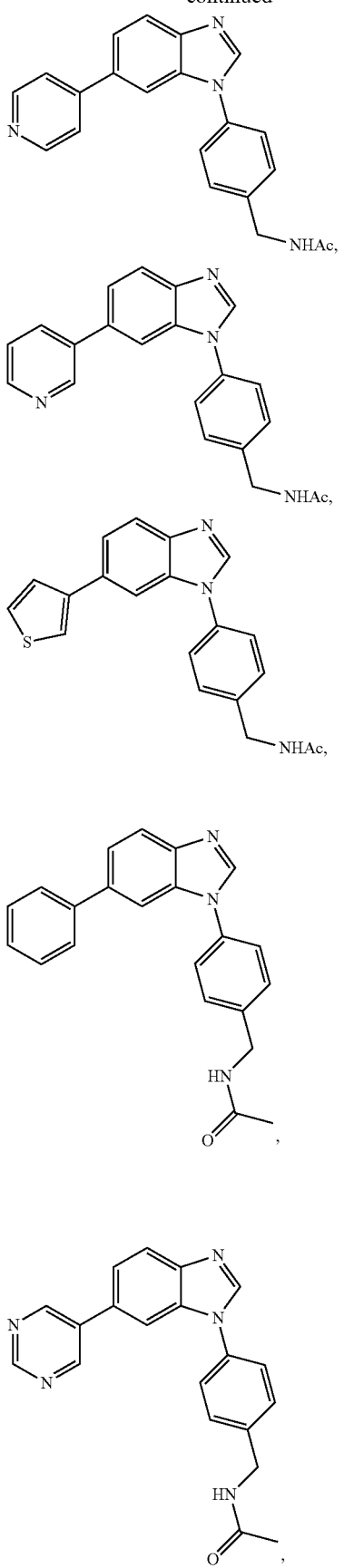
-continued
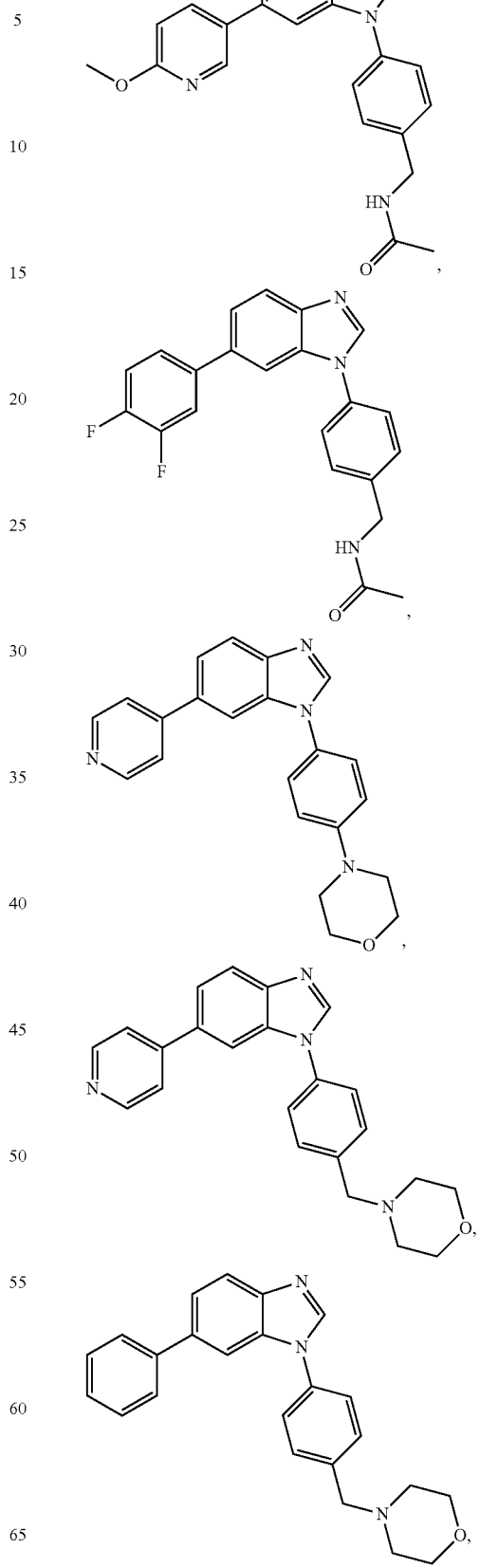

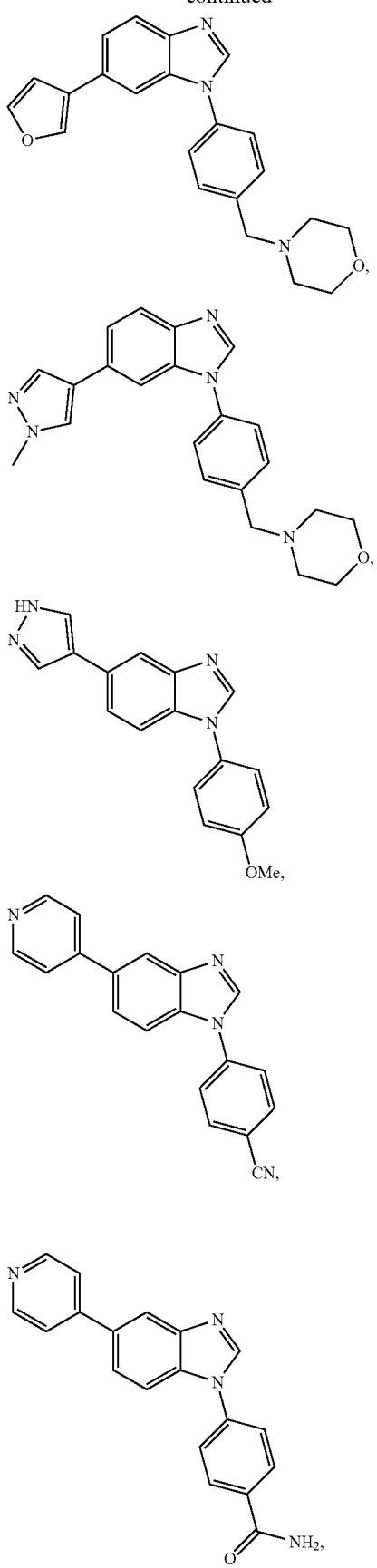
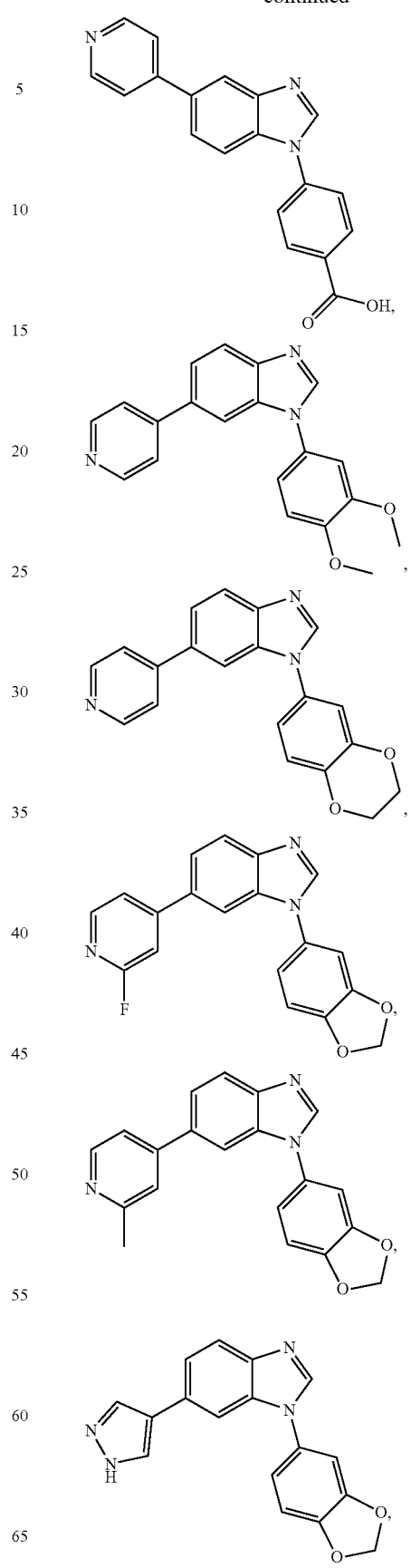

127
-continued
128
-continued
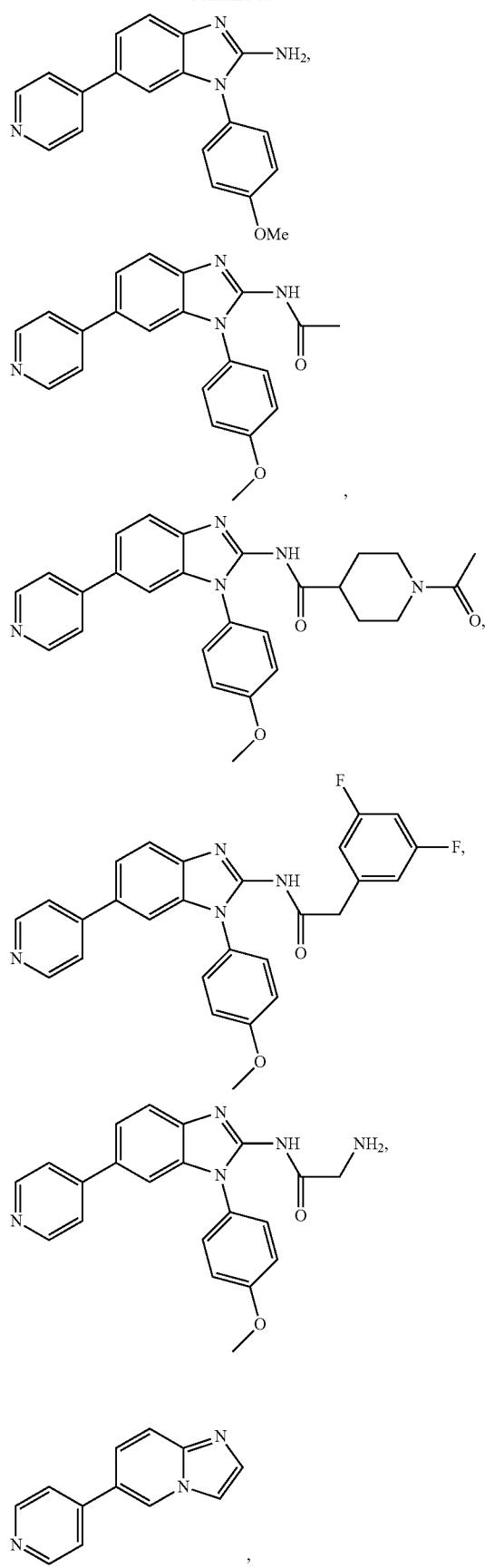
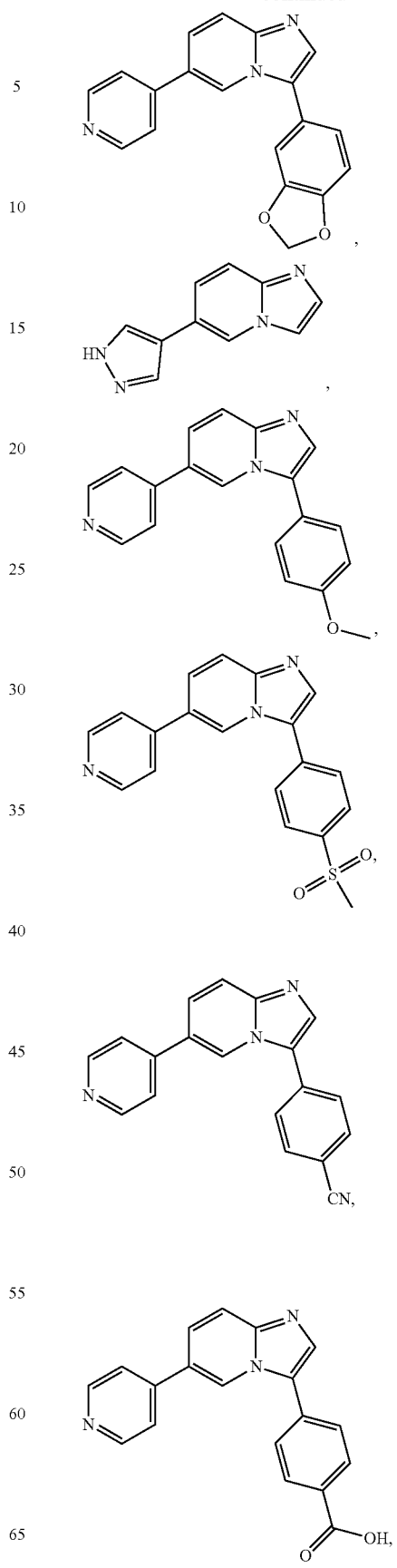

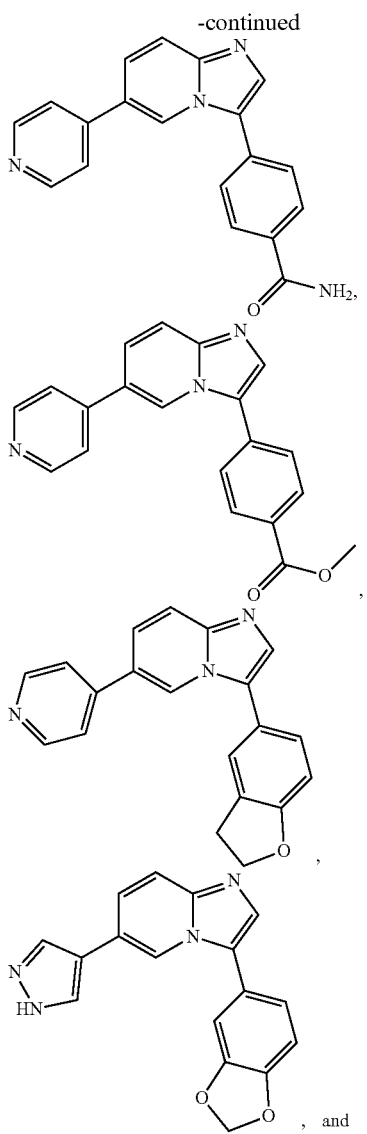

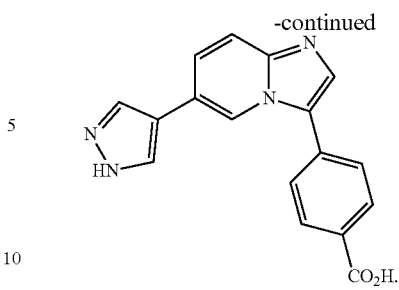

3. The compound of claim 1, wherein the compound is within a pharmaceutical composition.

4. A method of treating, ameliorating, or preventing a disorder related to DYRK1A activity in a patient comprising administering to said patient a therapeutically effective amount of the pharmaceutical composition of claim 3.

5. The method of claim 4, wherein said disorder related to DYRK1A activity is Alzheimer's disease, Down syndrome, Huntington's disease, Parkinson's disease, an autoimmune disease, an inflammatory disorder, or cancer.

6. The method of claim 5, wherein said patient is a human patient.

7. The method of claim 5, further comprising administering to said patient one or more agents for treating Alzheimer's disease, Down syndrome, Huntington's disease, Parkinson's disease, an autoimmune disease, an inflammatory disorder, or cancer.

8. A kit comprising a compound of claim 1 and instructions for administering said compound to a patient having a disorder related to DYRK1 activity.

9. The kit of claim 8, wherein the disorder related to DYRK1 activity is Alzheimer's disease, Down syndrome, Huntington's disease, Parkinson's disease, autoimmune disease, an inflammatory disorder, or cancer.

10. The kit of claim 8, further comprising one or more agents for treating Alzheimer's disease, Down syndrome, Huntington's disease, Parkinson's disease, autoimmune disease, an inflammatory disorder, or cancer.

* * * * *

UNITED STATES PATENT AND TRADEMARK OFFICE
CERTIFICATE OF CORRECTION

PATENT NO. : 10,730,842 B2
APPLICATION NO. : 15/756917
DATED : August 4, 2020
INVENTOR(S) : Christopher Hulme, Travis Dunckley and Yeng-Jeng Shaw It is certified that error appears in the above-identified patent and that said Letters Patent is hereby corrected as shown below:

In the Claims

Column 114, Claim 1, Lines 46-49 should read:

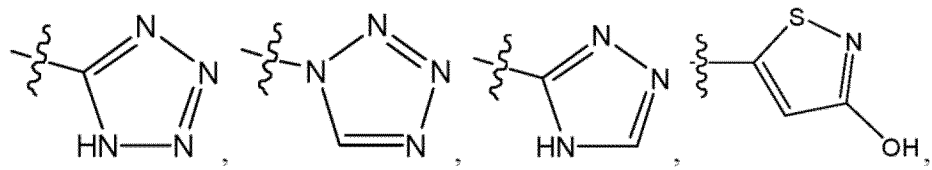

Column 114, Claim 1, Lines 61-65 should read:

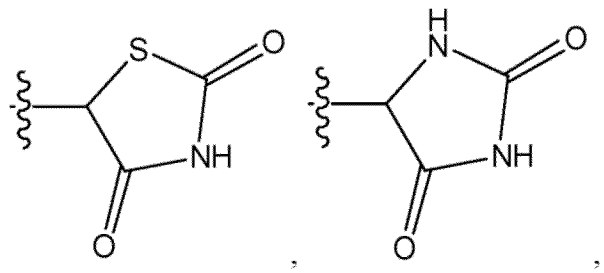

Signed and Sealed this
Fifteenth Day of December, 2020

Andrei Iancu
*Director of the United States Patent and Trademark Office*

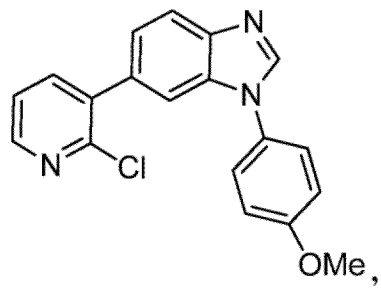

Column 116, Claim 2, Lines 25-35 should read: